US009540450B2

(12) United States Patent
Van De Winkel et al.

(10) Patent No.: US 9,540,450 B2
(45) Date of Patent: Jan. 10, 2017

(54) METHODS AND ANTIBODIES FOR TREATING CANCER

(71) Applicant: GENMAB A/S, Copenhagen (DK)

(72) Inventors: Jan Van De Winkel, Zeist (NL); Paul Parren, Odijk (NL); Willem Karel Bleeker, Amsterdam (NL); Klaus Edvardsen, Klampenborg (DK); Jeroen Lammerts Van Bueren, Harderwijk (NL); Thomas Valerius, Neuwittenbek (DE); Michael Dechant, Bordesholm (DE); Wencke Weisner, Bremen (DE); Sven Berger, Haute-Savoie (FR)

(73) Assignee: GENMAB A/S, Copenhagen (DK)

( * ) Notice: Subject to any disclaimer, the term of this patent is extended or adjusted under 35 U.S.C. 154(b) by 95 days.

(21) Appl. No.: 14/199,391

(22) Filed: Mar. 6, 2014

(65) Prior Publication Data
US 2014/0348833 A1 Nov. 27, 2014

Related U.S. Application Data

(63) Continuation of application No. 12/676,798, filed as application No. PCT/DK2008/050220 on Sep. 5, 2008, now abandoned.

(30) Foreign Application Priority Data

Sep. 6, 2007 (DK) .................................. 2007 01278
Jun. 30, 2008 (DK) .................................. 2008 00912

(51) Int. Cl.
*C07K 16/28* (2006.01)
*C07K 16/40* (2006.01)
(Continued)

(52) U.S. Cl.
CPC ........... *C07K 16/40* (2013.01); *C07K 16/2863* (2013.01); *C07K 16/44* (2013.01); *C07K 16/468* (2013.01);
(Continued)

(58) Field of Classification Search
None
See application file for complete search history.

(56) References Cited

U.S. PATENT DOCUMENTS 7,498,142 B2  3/2009  Yarden et al.
7,589,180 B2  9/2009  Old et al.
(Continued)

FOREIGN PATENT DOCUMENTS

WO  02/092771 A2  11/2002
WO  02/100348 A2  12/2002
(Continued)

OTHER PUBLICATIONS

MacCallum et al., Antibody-antigen interactions: contact analysis and binding site topography, J. Mol. Biol. 262:732-745, 1996.*
(Continued)

*Primary Examiner* — Claire Kaufman
(74) *Attorney, Agent, or Firm* — Nelson Mullins Riley & Scarborough LLP; Jane E. Remillard, Esq.; Christopher L. Frank

(57) ABSTRACT

The invention relates to novel methods for the treatment of tumors, comprising administration of a bispecific antibody or a combination of two or more non-cross-blocking antibodies that recognize the same target antigen or antigenic complex. In particular, the invention relates to a method for inducing complement-mediated cell killing in the treatment of a tumor, said method comprising combined administration, to a human being in need thereof, of a first antibody and a second antibody, wherein
(Continued)

said first antibody binds EGFR,
said second antibody binds EGFR,
said first and second antibody are non-cross-blocking, and the dosage regimen is such that CDC is obtained at the tumor site.

14 Claims, 29 Drawing Sheets

(51) Int. Cl.
  C07K 16/44    (2006.01)
  C07K 16/46    (2006.01)
  G01N 33/573   (2006.01)
  A61K 39/00    (2006.01)

(52) U.S. Cl.
  CPC ....... *G01N 33/573* (2013.01); *A61K 2039/505* (2013.01); *A61K 2039/507* (2013.01); *C07K 2317/21* (2013.01); *C07K 2317/24* (2013.01); *C07K 2317/31* (2013.01); *C07K 2317/54* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/92* (2013.01)

(56) References Cited

U.S. PATENT DOCUMENTS

| | | | |
|---|---|---|---|
| 7,595,378 B2 | 9/2009 | van de Winkel et al. | |
| 7,829,678 B2* | 11/2010 | Bristol | C07K 16/303 |
| 7,887,805 B2 | 2/2011 | Pedersen et al. | |
| 8,715,669 B2* | 5/2014 | Masternak | C07K 16/244 |
| 2011/0256142 A1 | 10/2011 | Van De Winkel et al. | |

FOREIGN PATENT DOCUMENTS

| | | |
|---|---|---|
| WO | 2004/032960 A1 | 4/2004 |
| WO | 2004/032961 A1 | 4/2004 |
| WO | 2008/104183 A2 | 9/2008 |

OTHER PUBLICATIONS

Lamminmaki et al., Chrystal structure of a recombinant anti-estradiol Fab fragment in complex with the 17beta-estradiol, J. Blol. Chem. 276:36687-94, 2001.*
Graeven et al., Phase I study of the humanised anti-EGFR monoclonal antibody matuzumab (EMD 72000) combined with gemcitabine in advanced pancreatic cancer, Br. J. Cancer, 94:1293-1299, May 2006.*
Office Action, U.S. Appl. No. 12/676,798, Jul. 9, 2015.
Office Action, U.S. Appl. No. 12/676,798, Jan. 15, 2015.
Office Action, U.S. Appl. No. 12/676,798, Mar. 22, 2013.
Office Action, U.S. Appl. No. 12/676,798, Jul. 27, 2012.
Office Action, U.S. Appl. No. 12/676,798, Mar. 09, 2012.
Baselga, Jose et al., "Critical Update and Emerging Trends in Epidermal Growth Factor Receptor Targeting in Cancer," Journal of Clinical Oncology, vol. 23(11):2445-2459 (2005).
Bleeker et al, "Dual mode of action of a human anti-epidermal growth facto receptor monoclonal antibody for cancer therapy," J.Immunol., vol. 173:4699-4707 (2004).
Carroll, Michael C., "The Role of Complement and Complement Receptors in Induction and Regulation of Immunity," Annu. Rev. Immunol., vol. 16:545-568 (1998).
Dechant, Michael et al., "Complement-Dependent Tumor Cell Lysis Triggered by Combinations of Epidermal Growth Factor Receptor Antibodies," Cancer Research, vol. 68(13):4998-5003 (2008).
Fearon, Douglas T., "The complement system and adaptive immunity," Seminars in Immunology, vol. 10:355-361 (1998).

Frank, Michael M., "Medical Intelligence, Current Concepts, Complement in the Pathophysiology of Human Disease," The New England Journal of Medicine, vol. 316(24):15251530 (1987).
Friedman, Lilach M. et al., "Synergistic down-regulation of receptor tyrosine kinases by combinations of mAbs: Implications for cancer immunotherapy," PNAS, vol. 102(6):1915-1920 (2005).
Gelderman, Kyra A. et al., "Complement function in mAb-mediated cancer immunotherapy," Trends in Immunology, vol. 25(3):158-164 (2004).
Haurum, John, "Synergy of anti-EGFR antibody combination leading to superior anti-cancer efficacy," Symphogen, IBC Antibody Engineering Conference (2008).
International Search Report and Written Opinion for Application No. PCT/DK2008/050220, dated Feb. 3, 2009.
Keane, P., Nimotuzumab. Research & Development Day, Apr. 5, 2006, Harvard Club, New York City [online], New York, New U York [retrieved Jan. 8, 2015]. Retrieved from the internet<URL:http://library.corporateirnetllibrary/14/143/143866/items/190821 /Number5NimotuzumabDrKEAN.pdf>.
Li et al, "Therapeutic anti-EGFR antibody 806 generates responses in murine de novo EGFR mutant-dependent lung carcinomas," J. Clin. Invest., vol. 117(2):346-352 (2007).
Logtenberg, Ton et al., "Antibody cocktails: next-generation biopharmaceuticals with improved potency," Trends in Biotechnology, vol. 25(9):390-394 (2007).
Macor, Paolo et al., "Complement Activated by Chimeric Anti-Folate Receptor Antibodies Is an Efficient Effector System to Control Ovarian Carcinoma," Cancer Research, vol. 66(7):3876-3883 (2006).
Macor, Paolo et al., "Complement as effector system in cancer immunotherapy," Immunology Letters, vol. 111:6-13 (2007).
Mendelsohn, John, "Targeting the Epidermal Growth Factor Receptor for Cancer Therapy," Journal of Clinical Oncology, vol. 20(18s):1s-13s (2002).
Pedersen, Mikkel Wandahl et al., "Sym004: A Novel Synergistic Anti-Epidermal Growth Factor Receptor Antibody Mixture with Superior Anticancer Efficacy," Cancer Res., vol. 70(2):588-597 (2010).
Perera, Rushika M. et al., "Treatment of Human Tumor Xenografts with Monoclonal Antibody 806 in Combination with a Prototypical Epidermal Growth Factor Receptor—Specific Antibody Generates Enhanced Antitumor Activity," Clinical Cancer Research, vol. 11(17):6390-6399 (2005).
Reuter, CWM et al., "Targeting EGF-receptor-signalling in squamous cell carcinomas of the head and neck," Br. J. Cancer, vol. 96(3):408-416 (2007).
Scott, Andrew M. et al., "A phase I clinical trial with monoclonal antibody ch806 targeting transitional state and mutant epidermal growth factor receptors," PNAS, vol. 104(10):4071-4076 (2007).
Sivasubramanian. A. et al., "Structural model of the mAb 806-EGFr complex using computational docking followed by computational and experimental mutagenesis," Structure, vol. 14(3):401-414 (2006).
Spangler, Jamie B. et al., "Combination antibody treatment downregulates epidermal growth factor receptor by inhibiting endosomal recycling," PNAS, vol. 107:13252-13257 (2010).
Spiridon, Camelia I. et al., "A Comparison of the in Vitro and in Vivo Activities of IgG and F(ab')2 Fragments of a Mixture of Three Monoclonal Anti-Her-2 Antibodies," Clinical Cancer Research, vol. 10:3542-3551 (2004).
Spiridon, Camelia I. et al., "Targeting Multiple Her-2 Epitopes with Monoclonal Antibodies Results in Improved Antigrowth Activity of a Human Breast Cancer Cell Line in Vitro and In Vivo," Clinical Cancer Research, vol. 8:1720-1730 (2002).
Taylor, Ronald P., "CD20 Trek: the next generation," Blood, vol. 104(6):1592 (2004).
Ullrich, Axel, et al., "Signal Transduction by Receptors with Tyrosine Kinase Activity," Cell, vol. 61:203-212 (1990).
Walport, Mark J., "Complement, First of Two Parts," The New England Journal of Medicine, vol. 344(14):1058-1066 (2001).

* cited by examiner

```
VH_1006-003m    1  EVQLVESGGGLVQPGGSLRLSCAASGFTFSSSYMTWVRQAPGKGLEWVANIQQDGSEKNY
VH_1006-008m    1  ...........................R...D.......S.............K.E..
VH_1006-005m    1  ....................................................H.K..Y..
VH_1006-011m    1  ...........................D...S.......R.............H.N..Y..
VH_1006-018m    1  ...............................N.....................KK...Y..

VH_1006-003m   61  LDSVKGRFTISRDNAKNSLSLQMNSLRAEDTAVYYCAR----TYSGFEDFWGQGTLVTVS
VH_1006-008m   61  ..V..........Y......................----.........Y.......
VH_1006-005m   61  ..V..................................----GELIYF.Y.........
VH_1006-011m   61  ..V...L..T.........Y.................----GELIYF.Y.........
VH_1006-018m   61  ..V...................................DLGWGWGWYF.L..R.....

```
VL_1006-003m    1  EIVLTQSPATLSLSPGERATLSCRASQSVSSYLAWYQQKPGQAPRLLIFDASNRATGIPA
VL_1006-008m    1  ............................................................
VL_1006-005a6m  1  ...........................................Y................
VL_1006-011d1m  1  ...........................................Y................
VL_1006-005b6m  1  ...........................................Y................
VL_1006-011a1m  1  ...........................................Y................
VL_1006-018m    1  ............................................................

VL_1006-003m   61  RFSGSGSGTDFTLTISSLEPEDFAVYYCQQRSNWPPWTFGQGTKVEIK
VL_1006-008m   61  ...............................................
VL_1006-005a6m 61  ............................-..................
VL_1006-011d1m 61  ............................-..................
VL_1006-005b6m 61  ............................-..................
VL_1006-011a1m 61  ............................-..................
VL_1006-018m   61  ............................-..................
```

Fig. 17B

METHODS AND ANTIBODIES FOR TREATING CANCER

This application is a continuation of U.S. patent application Ser. No. 12/676,798, filed on Dec. 21, 2010, which is a 35 U.S.C. 371 national stage filing of International Application No. PCT/DK2008/050220, filed on Sep. 5, 2008, which claims the benefit of Denmark Patent Application Nos. PA 2008 00912, filed Jun. 30, 2008, and PA 2007 01278, filed Sep. 6, 2007, the entire contents of which are incorporated herein by this reference.

FIELD OF THE INVENTION

Field of the Invention

The present invention relates to novel methods for the treatment of tumors, comprising administration of a bispecific antibody or a combination of two or more non-cross-blocking antibodies that recognize the same target antigen or antigenic complex. Furthermore, the invention relates to novel anti-EGFR antibodies.

Background of the Invention

The erbB family of four receptor tyrosine kinases, EGFR/HER1/erbB1, HER2/NEU/erbB2, HER3/erbB3 and HER4/erbB4 occupies a central role in a wide variety of biological processes from neuronal development to breast cancer. EGFR, the epidermal growth factor receptor, is a tyrosine kinase receptor with critical functions in the regulation of cell proliferation, differentiation and survival (Ullrich and Schlessinger (1990) Cell 61:203-212). Dysregulated function or expression of the EGFR is observed in common cancers such as lung, colon, head and neck, and also in non-epithelial malignancies such as glioblastomas—often correlating with a poor prognosis for the patients. Due to its documented involvement in tumorigenesis, EGFR constitutes a promising molecule for targeted therapy (Mendelsohn (2002) J. Clin. Oncol. 20:1 S-13S).

So far, two EGFR-directed approaches have been successfully introduced into clinical practice: small molecule tyrosine kinase inhibitors, and EGFR-directed monoclonal antibodies (Baselga et al. (2005) J. Clin. Oncol. 23:2445-2459). Anti-EGFR antibodies that have been tested in clinical trials include cetuximab (C225), panitumumab (E7.6.3), nimotuzumab (hR3), matuzumab (425), zalutumumab (2F8) and ch806. While most antibodies recognize both wild-type and mutant forms of EGFR (e.g. the EGFR-vIII mutant), antibody ch806 preferentially recognizes an epitope only exposed on overexpressed, mutant or ligand-activated forms of EGFR (Scott et al. (2007) PNAS 104:4071.4076; WO 02/092771). With the exception of panitumumab, all these EGFR antibodies are of the human IgG1 isotype.

WO 2004/032960 describes that combination of two anti-EGFR antibodies that bind to different epitopes on EGFR gives a minor increase in inhibition of ligand binding and an increase in EGFR down-modulation as compared to each of the antibodies alone. Pharmaceutical compositions or kits comprising such antibody combinations and their use in the treatment of tumors have been proposed in WO 2004/032960.

WO 02/100348 discloses a composition comprising a combination of two or more human anti-EGFR antibodies, wherein each of said antibodies or antigen-binding portions thereof binds to a distinct epitope of EGFR. WO 02/092771 discloses that a composition comprising ch806 may be administered with, or may include combinations along with other anti-EGFR antibodies.

Perera et al. (2005) Clin. Cancer Res. 11:6390-6399 describe that treatment of human tumor xenografts with antibody ch806 in combination with the non-tumor-specific monoclonal antibody 528 generates enhanced antitumor activity. A down-modulation of the receptor was observed.

Antibodies can have activity on target cells via several different mechanisms of action. Conceptually, these effector mechanisms can be divided into direct mechanisms, mediated by the antibodies' variable regions, and indirect mechanisms, which are triggered by their constant regions. Direct mechanisms include blockade of ligand binding and signalling, receptor down-modulation, induction of apoptosis and inhibition of growth and survival. Indirect mechanisms include complement-dependent tumor cell lysis or complement-dependent cytotoxicity (CDC) and effector-cell-mediated tumor killing or antibody-dependent cell-mediated cytotoxicity (ADCC), tumor cell phagocytosis, and potentially antibody-mediated antigen presentation.

The complement system is a phylogenetically old cascade of proteases, which is tightly controlled by regulatory proteins in the plasma and on cellular surfaces (Walport (2001) N. Engl. J. Med. 344:1058-1066). Complement constitutes an integral link between the innate and the adaptive immune systems (Carroll (1998) Annu. Rev. Immunol. 16:545.568), and lack of critical components predisposes to immunodeficiency and autoimmunity (Frank (1987) N. Engl. J. Med. 316-1525-1530). Today, three pathways of complement activation have been identified—with the "classical" pathway triggered by C1q binding to complexed IgG. Complement activation may lead to the formation of the "membrane attack complex" (MAC)— triggering lytic killing of bacteria and eukaryotic cells. Furthermore, complement components like C5a and C3a are potent chemoattractants for immune effector cells, and other complement proteins like C3b and C3d effectively enhance antigen presentation (Fearon et al. (1998) Semin. Immunol. 10:355-361).

The contribution of complement for the in vivo efficacy of therapeutic antibodies has been investigated most extensively for CD20 antibodies like e.g. rituximab (Taylor (2004) Blood 104:1592). Here, data suggest that complement dependent killing mechanisms may at least contribute to antibody efficacy under certain conditions.

Complement-dependent tumor cell killing has so far not been described for EGFR antibodies either in vivo or in vitro.

While the above-described antibody therapies have proved to be of significant benefit for cancer therapy, a need for further improvement of cancer therapy remains, in particular for aggressive EGFR-associated cancers, e.g. lung and head and neck cancers, which still have a poor prognosis.

SUMMARY OF THE INVENTION

It has now surprisingly been found that combinations of non-cross-blocking anti-EGFR antibodies very potently deposit complement components C1q and C4c on tumor cells, leading to highly effective complement-mediated cell killing (CDC). This observation has provided the basis for new and more efficient methods of treatment of cancer.

Accordingly, in a first main aspect, the invention relates to a method for inducing complement-mediated cell killing (CDC) in the treatment of a tumor comprising combined administration, to a human being in need thereof, of a first antibody and a second antibody, wherein
  said first antibody binds EGFR,
  said second antibody binds EGFR,
  said first and second antibody are non-cross-blocking, and
  the dosage regimen is such that CDC is obtained at the tumor site.

In a particularly interesting embodiment of the method of the invention,
a) the first antibody is an antibody which binds an EGFR epitope which is found in all wild-type-EGFR-expressing cells,
b) the second antibody is an antibody, such as ch806, which binds an EGFR epitope which is found in tumor cells, but is not detectable in normal cells, and
c) the dosage regimen is such that substantial CDC is obtained at tumor sites, but substantially no CDC is obtained at non-tumor sites.

For example, the dosage regimen defined in c) may be obtained by dosing the first antibody in a dosage regimen which is at least equal to what is usual for anti-EGFR antibody therapy and dosing the second antibody in a dosage regimen which is significantly lower than what is usual for anti-EGFR antibody therapy. Without being bound by any specific theory, it is believed that in such a dosage regimen:

the full dosage of the first antibody ensures efficient anti-tumor activity on cells that overexpress wild-type EGFR, inter alia through efficient inhibition of ligand binding and/or ADCC, and an additional therapeutic effect is obtained from CDC due to the combination of two non-cross-blocking antibodies, wherein the lower dosage of the second antibody, together with the preferential binding to tumor cells, ensures CDC activation at tumor sites, while avoiding substantial CDC at non-tumor sites.

In a further main aspect, the invention relates to a bispecific antibody comprising a first binding specificity which binds an EGFR epitope which is found on all wild-type-EGFR-expressing cells and a second binding specificity which binds an EGFR epitope which is found in tumor cells, but is not detectable in normal cells, preferably an EGFR epitope which is located within the region comprising residues 273-501 of EGFR, more preferably the same EGFR epitope as bound by ch806, wherein said first and second binding specificity are non-cross-blocking.

In an even further aspect, the invention relates to an isolated monoclonal antibody which binds to human EGFR, wherein the antibody binds to the same epitope on EGFR as an antibody selected from the group consisting of:

an antibody having a heavy chain variable region having the amino acid sequence shown in SEQ ID NO: 7 and a light chain variable region having the amino acid sequence shown in SEQ ID NO: 8;

an antibody having a heavy chain variable region having the amino acid sequence shown in SEQ ID NO: 9 and a light chain variable region having the amino acid sequence shown in SEQ ID NO: 10;

an antibody having a heavy chain variable region having the amino acid sequence shown in SEQ ID NO: 9 and a light chain variable region having the amino acid sequence shown in SEQ ID NO: 11;

an antibody having a heavy chain variable region having the amino acid sequence shown in SEQ ID NO: 12 and a light chain variable region having the amino acid sequence shown in SEQ ID NO: 13;

an antibody having a heavy chain variable region having the amino acid sequence shown in SEQ ID NO: 14 and a light chain variable region having the amino acid sequence shown in SEQ ID NO: 15;

an antibody having a heavy chain variable region having the amino acid sequence shown in SEQ ID NO: 14 and a light chain variable region having the amino acid sequence shown in SEQ ID NO: 16; and an antibody having a heavy chain variable region having the amino acid sequence shown in SEQ ID NO: 17 and a light chain variable region having the amino acid sequence shown in SEQ ID NO: 18.

DESCRIPTION OF THE FIGURES

FIG. 7B: matuzumab-FITC; FIG. 7C: panitumumab-FITC; FIG. 7D: zalutumumab-FITC; FIG. 7E: 003-FITC; FIG. 7F: 005-FITC; FIG. 7G: 008-FITC; FIG. 7H: 011-FITC; FIG. 7I: 018-FITC) were incubated with 200-fold excess of unlabeled antibodies. Immunofluoresence in the presence of KLH antibody determined the maximum fluorescence. "% of maximal MFI" was calculated. Data are presented as mean±SEM of at least three independent experiments, * indicates significant changes in binding ($p<0.05$).

(FIGS. 10A and 10B) While individual EGFR antibodies did not trigger C1q deposition, all examined non cross-blocking combinations led to C1q deposition (significance ($p<0.05$) indicated by *). Data are presented as mean±SEM of at least three independent experiments. As shown in FIG. 11, the combination of three non-blocking antibodies is superior to individual combinations in C1q deposition (n=3; significant binding ($p<0.05$) is indicated by *, significant difference between triple and double combinations ($p<0.05$) by #).

FIGS. 17A and 17B: Alignment of VH (FIG. 17A) and VL (FIG. 17B) sequences of LC1006-003 (SEQ ID NO: 7 for VH and SEQ ID NO: 8 for VL), LC1006-005 (SEQ ID NO: 9 for VH, and SEQ ID NO: 10 (005b6m) and SEQ ID NO: 11 (005a6m for VL), LC1006-008 (SEQ ID NO: 12 for VH and SEQ ID NO: 13 for VL), LC1006-0011 (SEQ ID NO: 14 for VH, and SEQ ID NO: 15 (011d1m) and SEQ ID NO: 16 (011a1m) for VL) and LC1006-018 (SEQ ID NO: 17 for VH and SEQ ID NO: 18 for VL). Dots indicate identity to the reference sequence.

DETAILED DESCRIPTION OF THE INVENTION

Definitions

Figure 1:
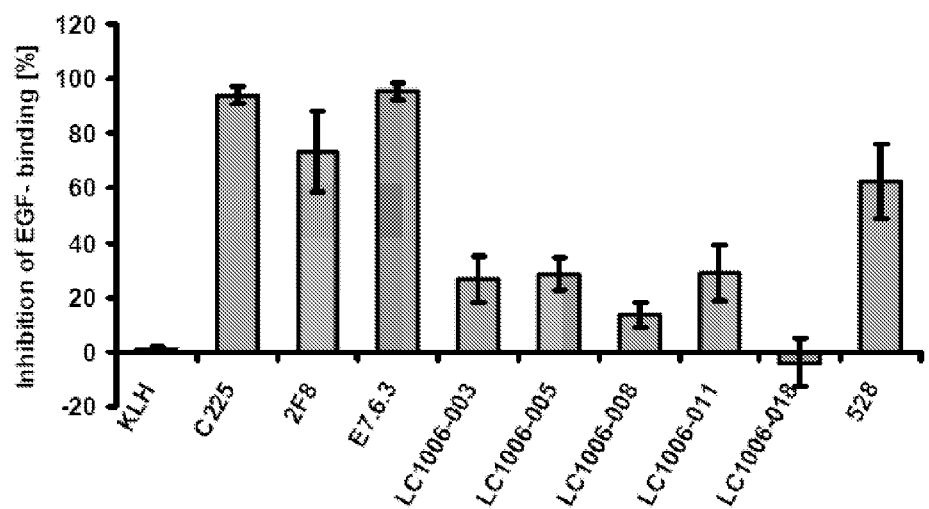
FIG. 1: Inhibition of ligand binding to EGFR by EGFR-antibodies. A431 cells were co-incubated with 2.5 µg/ml FITC-conjugated EGF and 200 µg/ml antibodies. Ligand binding was analyzed by flow cytometry. Blockade of ligand binding was calculated by the formula: % inhibition of EGF-binding=(RFI without−RFI with antibody)/(RFI without antibody)×100. Data are presented as mean±SEM of three independent experiments.

The term "erbB protein", when used herein, refers to a protein of the erbB protein family. This family is composed of four members: EGFR/HER1/erbB1, HER2/NEU/erbB2, HER3/erbB3 and HER4/erbB4. Unless specified otherwise, the term "EGFR" includes both wild-type EGFR and mutant or variant forms of EGFR, such as EGFRvIII.

When used herein, the terms "cross-blocking" or "non-cross-blocking" in the context of two antibodies, refer to two antibodies which, respectively, do and do not significantly compete for binding to an antigen, such as EGFR, in the assay described in Example 5, with a threshold for significance of 50%. Thus, two cross-blocking antibodies cannot be bound to the target antigen at the same time. Two non-cross-blocking antibodies on the other hand can be bound to the target antigen at the same time.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Methods for epitope mapping are well-known in the art.

When used herein, the term "same epitope", e.g. in the context of two antibodies that bind the same epitope, refers to antibodies that bind the same amino acid residues on the target antigen. Thus, "same epitope" is a more narrow concept than "cross-blocking", since two antibodies can e.g. bind different epitopes, i.e. different amino acid residues on the target antigen, but still be cross-blocking due to steric hindrance. Typically, two antibodies that cross-block with each other, but differ with respect to cross-blocking with a third antibody, do not bind the same epitope.

When used herein, the term "normal" cells in the context of EGFR-expressing cells refers to a cell, e.g. a keratinocyte, which expresses endogenous EGFR, but not the truncated de2-7 form of EGFR (EGFR-vIII). Furthermore, the term specifically excludes a cell that overexpresses the EGFR gene (see also WO 02/092771, incorporated herein by reference).

The term "all wild-type-EGFR-expressing cells", on the other hand, refers to all cells that express non-truncated wild-type EGFR, regardless of whether the cells is a tumor cell or not and regardless of whether EGFR is overexpressed or not.

When used herein, the term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$) and a heavy chain constant region. The heavy chain constant region typically is comprised of three domains, $C_H1$, $C_H2$, and $C_H3$. Each light chain typically is comprised of a light chain variable region (abbreviated herein as $V_L$) and a light chain constant region. The light chain constant region typically is comprised of one domain, $C_L$. The $V_H$ and $V_L$ regions may be further subdivided into regions of hyper-variability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Typically, the numbering of amino acid residues in this region is performed by the method described in Kabat et al., Sequences of Proteins of Immunological Interest, 5th Ed. Public Health Service, National Institutes of Health, Bethesda, Md. (1991) (phrases such as variable domain residue numbering as in Kabat or according to Kabat herein refer to this numbering system for heavy chain variable domains or light chain variable domains). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions for significant periods of time such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to modulate a physiological response associated with antibody binding to the antigen and/or time sufficient for the antibody to recruit an Fc-mediated effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation.

As indicated above, the term antibody herein, unless otherwise stated or clearly contradicted by context, includes fragments of an antibody that retain the ability to specifically bind to an antigen. It has been shown that the antigen-binding function of an antibody may be performed by fragments of a full-length antibody. Examples of binding fragments encompassed within the term "antibody" include, but are not limited to: (i) a Fab fragment, a monovalent fragment consisting of the $V_L$, $V_H$, $C_L$ and $C_H 1$ domains; (ii) F(ab)$_2$ and F(ab')$_2$ fragments, bivalent fragments comprising two Fab fragments linked by a disulfide bridge at the hinge region; (iii) a Fd fragment consisting essentially of the $V_H$ and $C_H 1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol 2003 November; 21(11):484-90); (vi) camelid or nanobodies (Revets et al; Expert Opin Biol Ther. 2005 January; 5(1):111-24), and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context.

Antibodies interact with target antigens primarily through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted into framework sequences from a different antibody with different properties (see for instance Riechmann, L. et al., Nature 332, 323-327 (1998), Jones, P. et al., Nature 321, 522-525 (1986) and Queen, C. et al., PNAS USA 86, 10029-10033 (1989)).

It also should be understood that the term antibody also generally includes polyclonal antibodies, monoclonal antibodies (mAbs), antibody-like polypeptides, such as chimeric antibodies and humanized antibodies, anti-idiotypic (anti-Id) antibodies to antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "bispecific molecule" is intended to include any agent, such as a protein, peptide, or protein or peptide complex, which has two different binding specificities. For example, the molecule may bind to, or interact with, (a) a cell surface antigen and (b) an Fc receptor on the surface of an effector cell.

The term "bispecific antibodies" is intended to include any EGFR antibody, which is a bispecific molecule. The term "bispecific antibodies" also includes diabodies and SMIP™s (Trubion). Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see for instance Holliger, P. et al., PNAS USA 90, 6444-6448 (1993), Poljak, R. J. et al., Structure 2, 1121-1123 (1994)). Methods for construction of bispecific antibodies have e.g. been discussed in Marcin and Zhu (2005) Acta Pharmacol Sin. 26:649.

In one embodiment, the two different binding specificities of the bispecific antibody are each contained within a half-molecule. A half-molecule typically consists of one heavy chain molecule and one light chain molecule.

As used herein, the terms "inhibits binding" and "blocks binding" (for instance when referring to inhibition/blocking of binding of a ligand to EGFR) are used interchangeably herein and encompass both partial and complete inhibition/blocking. The inhibition/blocking of binding of a ligand to a receptor normally reduces or alters the normal level or type of cell signaling that occurs when a ligand binds to the receptor. Inhibition and blocking are also intended to include any measurable decrease in the binding affinity of a ligand to its receptor due to a binding protein, e.g. an antibody.

Binding of a ligand to a receptor may e.g. be inhibited by at least about 10%, 20%, 30%, 40%, 50%, 60%, 70%, 80%, 90%, 99%, or 100%.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, neutrophils, polymorphonuclear cells, granulocytes, mast cells, and basophiles. Some effector cells express specific Fc receptors and carry out specific immune functions. In some embodiments, an effector cell is capable of inducing antibody-dependent cellular cytotoxicity (ADCC), such as a neutrophil capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen, target cell, or microorganism. The expression of a particular FcR on an effector cell may be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

The term "human antibody", as used herein, is intended to include antibodies having variable and constant regions derived from human germline immunoglobulin sequences. The human antibodies of the present invention may include amino acid residues not encoded by human germ line immunoglobulin sequences (for instance mutations introduced by random or site-specific mutagenesis in vitro or by somatic mutation in vivo). However, the term "human antibody", as used herein, is not intended to include antibodies in which CDR sequences derived from the germ line of another mammalian species, such as a mouse, have been grafted into human framework sequences. As used herein, a human antibody is "derived from" a particular germ line sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germ line immunoglobulin gene. Typically, outside the heavy chain CDR3, a human antibody derived from a particular human germ line sequence will display no more than 10 amino acid differences, such as no more than 5, for instance no more than 4, 3, 2, or 1 amino acid difference from the amino acid sequence encoded by the germ line immunoglobulin gene.

The term "chimeric antibody" refers to an antibody that contains one or more regions from one antibody and one or more regions from one or more other antibodies. The term "chimeric antibody" includes monovalent, divalent, or polyvalent antibodies. Chimeric antibodies are produced by recombinant processes well known in the art (see for instance Cabilly et al., PNAS USA 81, 3273-3277 (1984), Morrison et al., PNAS USA 81, 6851-6855 (1984), Boulianne et al., Nature 312, 643-646 (1984), EP125023, Neuberger et al., Nature 314, 268-270 (1985), EP171496, EP173494, WO86/01533, EP184187, Sahagan et al., J. Immunol. 137, 1066-1074 (1986), WO87/02671, Liu et al., PNAS USA 84, 3439-3443 (1987), Sun et al., PNAS USA 84, 214-218 (1987), Better et al., Science 240, 1041-1043 (1988) and Harlow et al., Antibodies: A Laboratory Manual, Cold Spring Harbor Laboratory Press, Cold Spring Harbor, N.Y., (1988)).

A "humanized antibody" is an antibody that is derived from a non-human species, in which certain amino acids in the framework and constant domains of the heavy and light chains have been mutated so as to avoid or abrogate an immune response in humans. Humanized forms of non-human (for instance murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, a humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. A humanized antibody typically also will comprise at least a portion of an immunoglobulin constant region (Fc), typically that of a human immunoglobulin. For further details, see Jones et al., Nature 321, 522-525 (1986), Riechmann et al., Nature 332, 323-329 (1988) and Presta, Curr. Op. Struct. Biol. 2, 593-596 (1992).

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germ line immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

The term "recombinant human antibody", as used herein, includes all human antibodies that are prepared, expressed, created or isolated by recombinant means, such as (a) antibodies isolated from an animal (such as a mouse) that is transgenic or transchromosomal for human immunoglobulin genes or a hybridoma prepared there from (described further elsewhere herein), (b) antibodies isolated from a host cell transformed to express the antibody, such as from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germ line immunoglobulin sequences. In certain embodiments, however, such recombinant human antibodies may be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germ line $V_H$ and $V_L$ sequences, may not naturally exist within the human antibody germ line repertoire in vivo.

As used herein, "antibody which binds X" refers to the binding of an antibody to a predetermined antigen X. Typically, the antibody binds with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low, then the amount with which the affinity for the antigen is lower than the affinity for a non-specific antigen may be at least 10,000 fold. Binding affinity also may be determined by equilibrium methods (for instance enzyme-linked immunoabsorbent assay (ELISA) or radioimmuno-assay (RIA)).

The term "$K_D$" (M), as used herein, refers to the dissociation equilibrium constant of a particular antibody-antigen interaction.

Antigen binding is preferably specific. The term "specific" herein refers to the ability of an antibody, e.g. an anti-EGFR antibody, to recognize an epitope within an antigen, e.g. EGFR, while only having little or no detectable reactivity with other portions of the antigen or with another, unrelated, antigen. Specificity may be relatively determined by competition assays as described herein. Specificity can more particularly be determined by any of the epitope identification/characterization techniques described herein or their equivalents known in the art. An antibody specific for a particular antigenic determinant may nonetheless cross-react with other biomolecules. For instance, an anti-EGFR antibody that binds human EGFR may cross-react with EGFR homologues from other species.

As used herein, "isotype" refers to the immunoglobulin class (for instance IgG1, IgG2, IgG3, IgG4, IgD, IgA1, IgA2, IgE, or IgM) that is encoded by heavy chain constant region genes.

The terms "transgenic, non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-EGFR antibodies when immunized with human EGFR antigen and/or cells expressing EGFR. The human heavy chain transgene may be integrated into the chromosomal DNA of the mouse, as is the case for transgenic mice, for instance HuMAb mice, such as HCo7 or HCo12 mice, or the human heavy chain transgene may be maintained extrachromosomally, as is the case for transchromosomal KM mice as described in WO02/43478. Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

The antibodies used in the present invention are typically used in and provided in an at least substantially isolated form. An "isolated" molecule refers to a molecule that is not associated with significant levels (such as more than about 1%, more than about 2%, more than about 3%, or more than about 5%) of any extraneous and undesirable physiological factors, such as non-EGFR biomolecules contained within a cell or animal in which the antibody is produced. An isolated molecule also refers to any molecule that has passed through such a stage of purity due to human intervention (whether automatic, manual, or both).

"Treatment" means the administration of an effective amount of a therapeutically active compound of the present invention with the purpose of easing, ameliorating or eradicating (curing) symptoms or disease states.

Further Aspects and Embodiments of the Invention

As explained above, in a first main aspect, the invention relates to a method for the treatment of a tumor comprising combined administration, to a human being in need thereof, of a first antibody and a second antibody, wherein
said first antibody binds EGFR,
said second antibody binds EGFR,
said first and second antibody are non-cross-blocking, and
the dosage regimen is such that CDC is obtained at the tumor site.
In the present context, the term "comprising" means "consisting at least of". Thus, the treatment may include further steps, including the administration of a third, fourth, fifth, etc, anti-EGFR antibody.
Similarly, the invention relates to a first antibody for use in the treatment of a tumor in combination with a second antibody, wherein
said first antibody binds EGFR,
said second antibody binds EGFR, and
said first and second antibody are non-cross-blocking, and
the dosage regimen is such that CDC is obtained at the tumor site.
Furthermore, the invention relates to a second antibody for use in the treatment of a tumor in combination with a first antibody, wherein
said first antibody binds EGFR,
said second antibody binds EGFR,
said first and second antibody are non-cross-blocking, and
the dosage regimen is such that CDC is obtained at the tumor site.
Moreover, the invention relates to the use of a first antibody and a second antibody for the preparation of a medicament for the treatment of a tumor, wherein
said first antibody binds EGFR,
said second antibody binds EGFR,
said first and second antibody are non-cross-blocking, and
the dosage regimen is such that CDC is obtained at the tumor site.

Antibodies Suitable for Use in the Invention

In one embodiment of the method of the invention, the first and/or second antibody used is a monoclonal antibody. In a further embodiment, the first and/or second antibody used is a human antibody. In another embodiment, the first and/or second antibody used is a chimeric or humanized antibody. In a further preferred embodiment, the first and/or second antibody used is an intact antibody, i.e. a full-length antibody rather than a fragment.

In one embodiment of the method of the invention, the first and/or second antibody used binds to human EGFR with an equilibrium dissociation constant ($K_D$) of $10^{-8}$ M or less, more preferably $10^{-10}$ M or less.

Further preferred anti-EGFR antibodies for use in the invention comprise antibodies that have one or more of the following properties:

a) the ability to opsonize a cell expressing EGFR;
b) the ability to inhibit growth and/or mediate phagocytosis and killing of cells expressing EGFR (e.g., a tumor cell) in the presence of human effector cells at a concentration of about 10 µg/ml or less (e.g., in vitro).

Antibodies used in the present invention may be in any suitable form with respect to multimerization. Also, if desired, the class of antibody used in the present invention may be switched by known methods. Thus, the effector function of the antibodies of the present invention may be changed by isotype switching to, e.g., an IgG1, IgG2, IgG3, IgG4, IgD, IgA, IgE, or IgM antibody for various therapeutic uses.

In one embodiment, the anti-EGFR antibody used in the present invention is an IgG1 antibody, for instance an IgG1,κ or IgG1,λ isotype. In another embodiment, the anti-EGFR antibody used in the present invention is an IgG3 antibody, for instance an IgG3,κ or IgG3,λ isotype. In yet another embodiment, the antibody used is an IgG4 antibody, for instance an IgG4,κ or IgG4,λ isotype. In a further embodiment, the anti-EGFR antibody used in the present invention is an IgA1 or IgA2 antibody. In an even further embodiment, the anti-EGFR antibody used in the present invention is an IgM antibody.

In a further embodiment, the first or second anti-EGFR antibody used is an antibody as described in WO02/100348, WO04/056847, WO200556606, WO05/012479, WO05/10151, U.S. Pat. No. 6,794,494, EP1454917, WO0314159, WO02092771, WO0312072, WO02066058, WO0188138, WO98/50433, WO98/36074, WO96/40210, WO 96/27010, US2002065398, WO95/20045, EP586002, U.S. Pat. No. 5,459,061 or U.S. Pat. No. 4,943,533.

In one embodiment of the method of the invention, said first antibody is an antibody which is capable of binding an EGFR epitope which is found on all wild-type-EGFR-expressing cells. Typically, such an epitope is also detectable on all wild-type-EGFR-expressing cells, either tumor cells or non-tumor cells expressing EGFR, such as cells in the skin, e.g. keratinocytes. Furthermore, such antibodies typically bind to wild-type EGFR regardless of whether or not it is in a ligand-activated form.

Preferably, said first antibody binds to human EGFR with an equilibrium dissociation constant ($K_D$) of at most $10^{-8}$ M, preferably at most $10^{-10}$ M and/or said first antibody is an antibody which is capable of inducing ADCC at the tumor site in the absence of said second antibody.

In one embodiment of the method of the invention, said first antibody is an antibody selected from the group consisting of: zalutumumab (2F8, described in WO02/100348 and WO04/056847), cetuximab (see e.g. Wong 2005 Clin Ther 27:684 and references therein), panitumumab (see e.g. Cohernuram and Saif (2007) Anticancer Drugs 18:7 and references therein), nimotuzumab (h-R3, see e.g. Spicer (2005) Curr Opin Mol Ther 7:182 and references therein), matuzumab (EMD72000, see e.g. Kim (2004) Curr Opin Mol Ther 6:96 and references therein), 528 (see e.g. Reilly J (2000) Nucl Med 41:903), LC1006-003 (described herein), LC1006-005 (described herein), LC1006-008 (described herein), LC1006-011 (described herein), LC1006-018 (described herein), and a variant antibody of any of these, such as a variant as described herein below.

Antibodies that bind to the same epitope of EGFR as the above mentioned antibodies are also suitable for use in the method of the invention.

Protein electron tomography analyses of zalutumumab in complex with EGFR showed that zalutumumab binds an epitope located in EGFR domain III (amino acid 313-482), which is one of the two ligand binding domains of EGFR. Cetuximab also binds an epitope located in EGFR domain III.

In one embodiment, the first antibody used in the method of the invention is an antibody which binds to an epitope within domain III of EGFR, i.e. within the region of amino acid 313-482.

In a further embodiment, first antibody is selected from the group consisting of:
an antibody which binds the same EGFR epitope as zalutumumab,
an antibody which binds the same EGFR epitope as cetuximab,
an antibody which binds the same EGFR epitope as panitumumab,
an antibody which binds the same EGFR epitope as nimotuzumab,
an antibody which binds the same EGFR epitope as matuzumab,
an antibody which binds the same EGFR epitope as 528,
an antibody which binds the same EGFR epitope as LC1006-003,
an antibody which binds the same EGFR epitope as LC1006-005,
an antibody which binds the same EGFR epitope as LC1006-008,
an antibody which binds the same EGFR epitope as LC1006-011, and
an antibody which binds the same EGFR epitope as LC1006-018.

Li et al, Cancer Cell, April 2005 vol. 7:301-311 showed in the crystal structure of sEGFR in complex with the cetuximab Fab fragment that cetuximab specifically interacts with EGFR amino acids R353, Q384, Q408, H409, F412, S418, S440, K443, K465, I467, S468, and N473.

Cross blocking studies using EGFR expressing cells showed that cetuximab cross blocks with zalutumumab and mAb 528. Zalutumumab, however, does not cross block with mAb 528, which shows that cetuximab and zalutumumab bind different epitopes. Fine-epitope mapping performed in binding studies using transiently-transfected, human-to-murine EGFR point-mutants showed that zalutumumab specifically interacts with amino acids K465, I467, K443 and S468.

Accordingly, in one embodiment, the first antibody is an antibody which interacts with one, more or all of amino acids R353, Q384, Q408, H409, F412, S418, S440, K443, K465, I467, S468 and N473 of EGFR, such as one, more or all of amino acids K465, I467, K443 and S468 of EGFR. Amino acids N473 and G471 are involved in binding of cetuximab, but are not important for binding of zalutumumab. In a further embodiment, the first antibody is an antibody which interacts with one, more or all of amino acids K465, I467, K443 and S468, but not with N473 and G471.

Similarly, in another embodiment, said first antibody is selected from the group consisting of:
an antibody which comprises the same heavy chain CDR3 sequence as zalutumumab and binds the same EGFR epitope as zalutumumab,
an antibody which comprises the same heavy chain CDR3 sequence as cetuximab and binds the same EGFR epitope as cetuximab,
an antibody which comprises the same heavy chain CDR3 sequence as panitumumab and binds the same EGFR epitope as panitumumab,
an antibody which comprises the same heavy chain CDR3 sequence as nimotuzumab and binds the same EGFR epitope as nimotuzumab,
an antibody which comprises the same heavy chain CDR3 sequence as matuzumab and binds the same EGFR epitope as matuzumab,
an antibody which comprises the same heavy chain CDR3 sequence as 528 and binds the same EGFR epitope as 528,
an antibody which comprises the same heavy chain CDR3 sequence as LC1006-003 and binds the same EGFR epitope as LC1006-003,
an antibody which comprises the same heavy chain CDR3 sequence as LC1006-005 and binds the same EGFR epitope as LC1006-005,
an antibody which comprises the same heavy chain CDR3 sequence as LC1006-008 and binds the same EGFR epitope as LC1006-008,
an antibody which comprises the same heavy chain CDR3 sequence as LC1006-011 and binds the same EGFR epitope as LC1006-011, and
an antibody which comprises the same heavy chain CDR3 sequence as LC1006-018 and binds the same EGFR epitope as LC1006-018.

In an even further embodiment, said first antibody is selected from the group consisting of:
an antibody which comprises the same 6 CDR sequences as zalutumumab,
an antibody which comprises the same 6 CDR sequences as cetuximab,
an antibody which comprises the same 6 CDR sequences as panitumumab,
an antibody which comprises the same 6 CDR sequences as nimotuzumab,
an antibody which comprises the same 6 CDR sequences as matuzumab,
an antibody which comprises the same 6 CDR sequences as 528,
an antibody which comprises the same 6 CDR sequences as LC1006-003,
an antibody which comprises the same 6 CDR sequences as LC1006-005,
an antibody which comprises the same 6 CDR sequences as LC1006-008,
an antibody which comprises the same 6 CDR sequences as LC1006-011, and
an antibody which comprises the same 6 CDR sequences as LC1006-018.

In a preferred embodiment of the method of the invention, said first antibody is an antibody which binds the same EGFR epitope as zalutumumab and said second antibody is selected from the group consisting of:
an antibody which binds the same EGFR epitope as nimotuzumab,
an antibody which binds the same EGFR epitope as matuzumab,
an antibody which binds the same EGFR epitope as LC1006-003,
an antibody which binds the same EGFR epitope as LC1006-005,
an antibody which binds the same EGFR epitope as LC1006-008,
an antibody which binds the same EGFR epitope as LC1006-011, and
an antibody which binds the same EGFR epitope as LC1006-018.

In another preferred embodiment of the method of the invention, said first antibody is an antibody which binds the same EGFR epitope as cetuximab and said second antibody is selected from the group consisting of:
an antibody which binds the same EGFR epitope as matuzumab,
an antibody which binds the same EGFR epitope as LC1006-003,
an antibody which binds the same EGFR epitope as LC1006-005,
an antibody which binds the same EGFR epitope as LC1006-008,
an antibody which binds the same EGFR epitope as LC1006-011, and
an antibody which binds the same EGFR epitope as LC1006-018.

In a further preferred embodiment of the method of the invention, said first antibody is an antibody which binds the same EGFR epitope as panitumumab and said second antibody is selected from the group consisting of:
an antibody which binds the same EGFR epitope as matuzumab,
an antibody which binds the same EGFR epitope as LC1006-003,
an antibody which binds the same EGFR epitope as LC1006-005,
an antibody which binds the same EGFR epitope as LC1006-008,
an antibody which binds the same EGFR epitope as LC1006-011, and
an antibody which binds the same EGFR epitope as LC1006-018.

In an even further preferred embodiment of the method of the invention, said first antibody is an antibody which binds the same EGFR epitope as nimotuzumab and said second antibody is selected from the group consisting of:
an antibody which binds the same EGFR epitope as LC1006-003,
an antibody which binds the same EGFR epitope as LC1006-005,
an antibody which binds the same EGFR epitope as LC1006-008,
an antibody which binds the same EGFR epitope as LC1006-011, and
an antibody which binds the same EGFR epitope as LC1006-018.

In another preferred embodiment of the method of the invention, said first antibody is an antibody which binds the same EGFR epitope as matuzumab and said second antibody is selected from the group consisting of:
an antibody which binds the same EGFR epitope as LC1006-003, an antibody which binds the same EGFR epitope as LC1006-005,
an antibody which binds the same EGFR epitope as LC1006-008, and
an antibody which binds the same EGFR epitope as LC1006-011.

In a further preferred embodiment of the method of the invention, said first antibody is an antibody which binds the same EGFR epitope as 528 and said second antibody is selected from the group consisting of:
an antibody which binds the same EGFR epitope as LC1006-003,
an antibody which binds the same EGFR epitope as LC1006-005,
an antibody which binds the same EGFR epitope as LC1006-008,
an antibody which binds the same EGFR epitope as LC1006-011, and
an antibody which binds the same EGFR epitope as LC1006-018.

In a yet even further preferred embodiment of the method of the invention, said first antibody is an antibody which binds the same EGFR epitope as LC1006-018 and said second antibody is selected from the group consisting of:
an antibody which binds the same EGFR epitope as nimotuzumab,
an antibody which binds the same EGFR epitope as LC1006-003,
an antibody which binds the same EGFR epitope as LC1006-005,
an antibody which binds the same EGFR epitope as LC1006-008, and
an antibody which binds the same EGFR epitope as LC1006-011.

Further embodiments of the antibodies used in the present invention are given below in the section "Production of antibodies".

Combinations of Antibodies Wherein One Antibody Preferentially Binds Tumor Cells In a particularly interesting embodiment of the method of the invention, treatment with one of the antibodies mentioned above is combined with an anti-EGFR antibody which preferentially binds tumor cells. In this embodiment of the method of the invention, the CDC induced by the combination therapy is more specifically directed to tumor cells, and strong CDC at healthy tissues, which may be undesirable for safety reasons, is avoided or at least reduced.

Thus, in one embodiment, the first antibody is one of the antibodies mentioned herein above, preferably one of the anti-EGFR antibodies mentioned herein above, and the second antibody is an antibody which is capable of binding to an EGFR epitope which is found in tumor cells, but is not detectable in normal cells.

In one embodiment, such a tumor-cell-specific anti-EGFR antibody is an antibody which is specific for an EGFR variant which is only expressed on tumor cells, e.g. EGFRvIII. Such an anti-EGFRvIII antibody may either recognize the neo-epitope in EGFRvIII, formed by the junction of sequences due to the deletion of exons 2-7 (see e.g. WO2005012479), or the anti-EGFRvIII antibody may recognize an epitope which does not demonstrate any amino acid sequence alterations or substitutions as compared to wild-type EGFR, but is only exposed on EGFRvIII.

In another embodiment, such a tumor-cell-specific anti-EGFR antibody binds preferentially to EGFRvIII, but also exhibits residual binding to wild-type EGFR, wherein the binding is detectable when EGFR is overexpressed, e.g. on tumor cells. Such antibodies typically recognize an EGFR epitope which does not demonstrate any amino acid sequence alterations or substitutions as compared to wild-type EGFR. In a preferred embodiment, such a tumor-cell-specific anti-EGFR antibody binds an EGFR epitope which is located within the region comprising residues 273-501 of EGFR, more preferably an EGFR epitope which is located within the region comprising residues 287-302 of EGFR. In a further embodiment, said second antibody is cross-blocking with ch806, such as a second antibody which binds the same EGFR epitope as ch806, e.g. a second antibody which comprises SEQ ID NO:3 and optionally one or more or all of SEQ ID NO:1, 2, 4, 5 and 6.

In an even further embodiment, said second antibody is ch806.

In another embodiment, said second, tumor-cell-specific, anti-EGFR antibody is MR1-1.

In another embodiment, the second antibody is an antibody which is specific for EGFR-vIII (i.e. does not bind wild-type EGFR). Such antibodies have e.g. been described by Hills et al. (1995) Int. J. Cancer 63:537-543, Humphrey et al. 1990 PNAS 87:4207-4211, and Wikstrand et al. 1995 Cancer Res. 55:3140-3148).

In a further embodiment, the second antibody binds to EGFR-vIII with a $K_D$ which is at least 10 fold lower, such as at least 50 fold lower, e.g. at least 100 fold lower than the $K_D$ for binding to wild-type EGFR.

Production of Antibodies

A monoclonal antibody refers to a composition comprising a homogeneous antibody population having a uniform structure and specificity. That an antibody is monoclonal is not to be construed as requiring production of the antibody by any particular method. For example, the monoclonal antibodies used in the present invention may be produced by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991).

Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc. In one embodiment, human monoclonal antibodies may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (µ and γ) and κ light chain immunoglobulin sequences, together with targeted mutations that inactivate the endogenous µ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N.

Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci. 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. No. 5,545,806, U.S. Pat. No. 5,569,825, U.S. Pat. No. 5,625,126, U.S. Pat. No. 5,633,425, U.S. Pat. No. 5,789,650, U.S. Pat. No. 5,877,397, U.S. Pat. No. 5,661,016, U.S. Pat. No. 5,814,318, U.S. Pat. No. 5,874,299, U.S. Pat. No. 5,770,429, U.S. Pat. No. 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo7 human heavy chain transgene (as described in U.S. Pat. No. 5,770,429).

The HCo12 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), a KCo5 human kappa light chain transgene (as described in Fishwild et al., Nature Biotechnology 14, 845-851 (1996)), and a HCo12 human heavy chain transgene (as described in Example 2 of WO 01/14424). In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478.

The KM mouse contains a human heavy chain transchromosome and a human kappa light chain transgene. The endogenous mouse heavy and light chain genes also have been disrupted in the KM mice such that immunization of the mice leads to production of human immunoglobulins rather than mouse immunoglobulins. Construction of KM mice and their use to raise human immunoglobulins is described in detail in WO 02/43478. Splenocytes from these transgenic mice may be used to generate hybridomas that secrete human monoclonal antibodies according to well known techniques.

Human monoclonal or polyclonal antibodies for use in the present invention, or antibodies for use in the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. No. 5,827,690, U.S. Pat. No. 5,756,687, U.S. Pat. No. 5,750,172 and U.S. Pat. No. 5,741,957.

Further, human antibodies for use in the present invention or antibodies for use in the present invention from other species may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized, for instance as described elsewhere herein.

Antibodies may also be recovered from recombinant combinatorial antibody libraries, such as a scFv phage display library, which may be made with human $V_L$ and $V_H$ cDNAs prepared from mRNA derived from human lymphocytes. Methods for preparing and screening such libraries are known in the art.

A "variant" antibody is an antibody that differs from a parent antibody (typically generated by immunization) by one or more suitable amino acid residue alterations, that is substitutions, deletions, insertions, or terminal sequence additions, in the CDRs or other $V_H$ and/or $V_L$ sequences (provided that at least a substantial amount of the epitope binding characteristics of the parent antibody are retained, if not improved upon, by such changes). Variations in an antibody variant may be made in each of the framework regions, the constant domain, and/or the variable regions (or any one or more CDRs thereof) in a single variant antibody. Alternatively, variations may be made in only one of the framework regions, the variable regions (or single CDR thereof), or the constant domain in an antibody.

A suitable amino acid residue substitution in the context of a CDR variant is any amino acid residue that permits the CDR to interact with the epitope to which the parent CDR is selective/specific and to cooperatively associate with other parent CDRs and/or variant CDRs similarly specific/selective for that epitope. Factors influencing the selection of a suitable amino acid sequence substitution may include the impact of the residue on the conformation of the CDR (e.g., retention of CDR loop structure and flexibility) and the ability to engage in noncovalent interactions (e.g., Van der Waals interactions, hydrogen bonding interactions, ionic interactions, and/or other interactions characteristic of epitope-variable region binding) with the epitope and/or other similar CDRs in a manner similar to or advantageous over the replaced residue in the parent CDR.

The percent identity between two sequences, e.g. variable domain sequences or CDR3 sequences, is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences may be accomplished using a mathematical algorithm, as described in the non-limiting examples below.

The percent identity between two nucleotide sequences may be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences may also be determined using the algorithm of E. Meyers and W. Miller, Comput. Appl. Biosci 4, 11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The sequence of CDR variants may differ from the sequence of the CDR of the parent antibody sequences through mostly conservative substitutions; for instance at least about 35%, about 50% or more, about 60% or more, about 70% or more, about 75% or more, about 80% or more, about 85% or more, about 90% or more, about 95% or more (e.g., about 65-99%) of the substitutions in the variant are conservative amino acid residue replacements. In the context of the present invention, conservative substitutions may be defined by substitutions within the classes of amino acids reflected in one or more of the following three tables:

Amino acid residue classes for conservative substitutions

| | |
|---|---|
| Acidic Residues | Asp and Glu |
| Basic Residues | Lys, Arg, and His |
| Hydrophilic Uncharged Residues | Ser, Thr, Asn, and Gln |
| Aliphatic Uncharged Residues | Gly, Ala, Val, Leu, and Ile |
| Non-polar Uncharged Residues | Cys, Met, and Pro |
| Aromatic Residues | Phe, Tyr, and Trp |

Variant antibodies used in the present invention may comprise framework (FR) alterations, that is outside the hypervariable region, for instance in the Fc region, which alterations may be associated with advantageous properties, such as changing the functional or pharmacokinetic properties of the antibodies. For example, a substitution or other modification (insertion, deletion, terminal sequence additions or combination of any thereof) in a framework region or constant domain may be associated with an increase in the half-life of the variant antibody with respect to the parent antibody, or may be made to alter the immunogenicity of the variant antibody with respect to the parent antibody, to provide a site for covalent or non-covalent binding to another molecule, or to alter such properties as complement fixation, for instance resulting in a decrease or increase of C1q binding and CDC or of FcγR binding and antibody-dependent cellular cytotoxicity (ADCC). Substitutions may for example be made in one or more of the amino acid residues 234, 235, 236, 237, 297, 318, 320, and 322 of the heavy chain constant region, thereby causing an alteration in an effector function while retaining binding to antigen as compared with the unmodified antibody, cf. U.S. Pat. No. 5,624,821 and U.S. Pat. No. 5,648,260. Further reference may be had to WO 00/42072 disclosing antibodies with altered Fc regions that increase ADCC, and WO 94/29351 disclosing antibodies having mutations in the N-terminal region of the $C_H2$ domain that alter the ability of the antibodies to bind to FcRI and thereby decreases the ability of the antibodies to bind to C1q which in turn decreases the ability of the antibodies to fix complement. Furthermore, Shields et al., J. Biol. Chem. 276, 6591-6604 (2001) teaches combination variants, which improve FcγRIII binding, for instance T256A/S298A, S298A/E333A, and S298A/E333A/K334A.

The in vivo half-life of the antibodies may also be improved by modifying the salvage receptor epitope of the Ig constant domain or an Ig-like constant domain such that the molecule does not comprise an intact $C_H2$ domain or an intact Ig Fc region, cf. U.S. Pat. No. 6,121,022 and U.S. Pat. No. 6,194,551. The in vivo half-life may furthermore be increased by making mutations in the Fc region, e.g. by substituting threonine for leucine at position 252, threonine for serine at position 254, or threonine for phenylalanine at position 256, cf. U.S. Pat. No. 6,277,375.

The present invention may also use fragments of antibodies (including variant antibodies). Examples of such antibody fragments include Fab, Fab', F(ab')$_2$, and Fv fragments. Thus, although the discussion herein may focus on antibodies, it should be understood that the embodiments and features of the antibodies may equally be applied to antibody fragments, such as Fab fragments, Fab' fragments, and scFv peptides, antibody-like peptides (peptides comprising a CDR), and bi- and multi-specific antibodies as appropriate, provided that the molecule retains at least a substantial proportion of the antigen-binding properties of the corresponding complete antibody. In some instances, antibody fragments may be associated with lower antigen-binding affinity, but may offer other advantageous features that may offset for any such loss in affinity.

Antibodies used in the present invention also include antibody derivatives. Such derivatives may be produced by chemically conjugating a radioisotope, protein, or other agent/moiety/compound to the N-terminal side or C-terminal side of the antibody or subunit thereof, an appropriate substituent group or side chain or to a sugar chain in the antibody (see, e.g., Antibody Engineering Handbook, edited by Osamu Kanemitsu, published by Chijin Shokan (1994)). Derivatives may also be generated by conjugation at internal residues or sugars, where appropriate.

In one embodiment, the present invention uses an antibody that is conjugated to a second molecule that is selected from a radionuclide, an enzyme, an enzyme substrate, a cofactor, a fluorescent marker, a chemiluminescent marker, a peptide tag, or a magnetic particle. In one embodiment, an antibody may be conjugated to one or more antibody fragments, nucleic acids (oligonucleotides), nucleases, hormones, immunomodulators, chelators, boron compounds, photoactive agents, dyes, and the like. These and other suitable agents may be coupled either directly or indirectly to an antibody. One example of indirect coupling of a second agent is coupling by a spacer moiety. These spacers, in turn, may be either insoluble or soluble (see for instance Diener et al., Science 231, 148 (1986)) and may be selected to enable drug release from the antibody at a target site and/or under particular conditions. Additional examples of therapeutic agents that may be coupled to an antibody include lectins and fluorescent peptides.

In one embodiment, antibody derivatives comprising one or more radiolabeled amino acids are used. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. No. 4,681,581, U.S. Pat. No. 4,735,210, U.S. Pat. No. 5,101,827, U.S. Pat. No. 5,102,990 (US RE35,500), U.S. Pat. No. 5,648,471 and U.S. Pat. No. 5,697,902. For example, a radioisotope may be conjugated by a chloramine T method.

In one embodiment, the present invention uses molecules comprising an antibody, such as an anti-EGFR antibody, conjugated to a therapeutic moiety, such as a cytotoxin, a chemotherapeutic drug, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. For a description of these classes of drugs which are well known in the art, and their mechanisms of action, see Goodman et al., Goodman and Gilman's The Pharmacological Basis Of Therapeutics, 8th Ed., Macmillan Publishing Co., 1990. Additional techniques relevant to the preparation of antibody immunotoxins are provided in for instance Vitetta, Immunol. Today 14, 252 (1993) and U.S. Pat. No. 5,194,594.

Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins (PAPI, PAPII, and PAP-S), *momordica charantia* inhibitor, curcin, crotin, saponaria officinalis inhibitor, gelonin, mitogellin, restrictocin, phenomycin, and enomycin toxins. Therapeutic agents, which may be administered in combination with antibody as described elsewhere herein, may also be candidates for therapeutic moieties useful for conjugation to an antibody.

Other examples of therapeutic cytotoxins that may be conjugated to an antibody used in the present invention include calicheamicins and duocarmycins. As indicated above, the drug moiety need not be construed as limited to classical chemical therapeutic agents. For example, the drug moiety may be a protein or polypeptide possessing a desired biological activity. Such proteins may include, for example, an agent active at the cell surface, such as phospholipase enzymes, e.g. phospholipase C.

The lysing portion of a toxin typically may be readily joined to the Fab fragment of an antibody or antibody fragment of the present invention. Other suitable conjugated molecules include ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Additional toxins suitable for use in the present invention are known to those of skill in the art (see for instance U.S. Pat. No. 6,077,499).

Techniques for conjugating such therapeutic moieties to antibodies, are well known, see for instance Amon et al., "Monoclonal Antibodies For Immunotargeting Of Drugs In Cancer Therapy", in Monoclonal Antibodies And Cancer Therapy, Reisfeld et al., (eds.), pp. 243-56 (Alan R. Liss, Inc. 1985), Hellstrom et al., "Antibodies For Drug Delivery", in Controlled Drug Delivery (2nd Ed.), Robinson et al., (eds.), pp. 623-53 (Marcel Dekker, Inc. 1987), Thorpe, "Antibody Carriers Of Cytotoxic Agents In Cancer Therapy: A Review", in Monoclonal Antibodies '84: Biological And Clinical Applications, Pinchera et al., (eds.), pp. 475-506 (1985), "Analysis, Results, And Future Prospective Of The Therapeutic Use Of Radiolabeled Antibody In Cancer Therapy", in Monoclonal Antibodies For Cancer Detection And Therapy, Baldwin et al., (eds.), pp. 303-16 (Academic Press 1985) and Thorpe et al., "The Preparation And Cytotoxic Properties Of Antibody-Toxin Conjugates", Immunol. Rev. 62, 119-58 (1982).

In one embodiment, the antibody used in the present invention is attached to a linker-chelator, e.g., tiuxetan, which allows for the antibody to be conjugated to a radioisotope.

Additionally useful conjugate substituents include anticancer retinoids. Taxane conjugates (see for instance Jaime et al., Anticancer Res. 21(2A), 1119-28 (2001), cisplatin conjugates, thapsigargin conjugates, linoleic acid conjugates, calicheamicin conjugates (see for instance Damle et al., Curr Opin Pharmacol. 3(4), 386-90 (2003), doxorubicin conjugates, geldanamycin conjugates, and the like, also may be useful in promoting the treatment of cancer (see, generally, Trail et al., Cancer Immunol Immunother. 52(5), 328-37 (2003)).

Antibodies used in the present invention may be prepared by recombinant expression in any suitable type of cells or animals. Recombinant antibodies, such as recombinant human antibodies also include antibodies isolated from a recombinant, combinatorial human antibody library, antibodies isolated from an animal, such as a transgenic animal, or antibodies prepared, expressed, created or isolated by any other means that involves splicing of human immunoglobulin-encoding nucleic acid sequences to other nucleic acid sequences exogenous to the human immunoglobulin-encoding nucleic acids and human immunoglobulin-encoding genes. Recombinant human antibodies typically have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and, thus, the amino acid sequences of the $V_H$ and $V_L$ regions of the recombinant antibodies may be sequences that, while derived from and related to human germ line $V_H$ and $V_L$ sequences, may not naturally exist within the human antibody germ line repertoire in vivo. Suitable methods for antibody production are known in the art and include those described in for instance Harlow et al., Antibodies: A Laboratory Manual, Cold Spring Harbor Laboratory Press, Cold Spring Harbor, N.Y., (1988), Harlow and Lane: Using Antibodies: A Laboratory Manual (Cold Spring Harbor Laboratory Press (1999)), U.S. Pat. No. 4,376,110 and Ausubel et al., eds., Current Protocols In Molecular Biology, Greene Publishing Assoc. and Wiley InterScience N.Y., (1987, 1992). Monoclonal antibodies may be made using the hybridoma method first described by Kohler et al., Nature 256, 495 (1975), or by other well-known, subsequently-developed methods (see, e.g., Goding, Monoclonal Antibodies: Principles and Practice, pp. 59-103 (Academic Press, 1986)). Transformed immortalized B cells may also be used to efficiently produce antibodies used in the present invention. Such cells may be produced by standard techniques, such as transformation with an Epstein Barr Virus, or a transforming gene. (See, e.g., "Continuously Proliferating Human Cell Lines Synthesizing Antibody of Predetermined Specificity," Zurawaki, V. R. et al., in Monoclonal Antibodies, ed. by Kennett R. H. et al., Plenum Press, N.Y. 1980, pp 19-33).

Recombinant cells comprising exogenous nucleic acids encoding antibodies used in the present invention may be prepared by any suitable technique (e.g., transfection/transformation with a naked DNA plasmid vector, viral vector, invasive bacterial cell vector or other whole cell vector, etc., comprising an antibody-encoding sequence (or sequences) delivered into the cell by calcium phosphate-precipitation facilitated transfection, receptor-mediated targeting and transfection, biolistic delivery, electroporation, dextran-mediated transfection, liposome-mediated transformation, protoplast fusion, direct microinjection, etc.). Methods of transforming/transfecting cells are well known in the art (see, e.g., Sambrook et al., Molecular Cloning: A Laboratory Manual, Cold Spring Harbor Laboratory Press (2d Edition, 1989 and 3rd Edition, 2001) and F. Ausubel et al., ed. Current Protocols in Molecular Biology, Greene Publishing and Wiley InterScience New York (1987). Such recombinant cells are a feature of the present invention.

Cell lines available as hosts for recombinant protein expression are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, and a number of other cell lines. Other cell lines that may be used are insect cell lines, such as Sf9 cells, or bacterial cells or eukaryotic unicellular microorganisms, such as yeast.

Human antibodies of the present invention may also be produced in a host cell transfectoma using, for example, a combination of recombinant DNA techniques and gene transfection methods as is well known in the art, see for instance Morrison, S., Science 229, 1202 (1985).

Dosage Regimens

In the method and use of the invention, the antibodies are given in an effective amount, i.e. in an amount effective, at dosages and for periods of time necessary, to achieve a desired result.

A therapeutically effective amount may vary according to factors such as the disease state, age, sex, and weight of the individual, and the ability of the agent to elicit a desired response in the individual.

An effective amount for tumor therapy may also be measured by its ability to stabilize the progression of disease. The ability of a compound to inhibit cancer may be evaluated in an animal model system predictive of efficacy in human tumors. Alternatively, this property of a composition may be evaluated by examining the ability of the compound to inhibit cell growth or to induce apoptosis by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

In a preferred embodiment of the method of the invention, the dosage regimen is such that substantial CDC is obtained at the tumor site. This may e.g. be tested using the methods described in Di Gaetano et al. (2003) J. Immunol. 171(3): 1581-7, Kennedy et al. (2004) J. Immunol. 2004 Mar. 1; 172(5):3280-8 and Gelderman et al. (2004) TRENDS in Immunology 25:158 and references mentioned therein, As non-limiting examples, treatment according to the present invention may be provided as a daily dosage of the first and/or second antibody in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In one embodiment of the method of the invention, the dosage regimen of said first antibody comprises administration, at least once per 14 days, of a dosage of antibody of at least 0.1 mg/kg, such as at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg. In a further embodiment, the dosage of the first antibody is at most 100 mg/kg, such as at most 50 mg/kg.

In another embodiment of the method of the invention, the dosage regimen of said second antibody comprises administration, at least once per 14 days, of a dosage of antibody of at least 0.1 mg/kg, such as at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg. In a further embodiment, the dosage of the second antibody is at most 100 mg/kg, such as at most 50 mg/kg.

In a further embodiment, the administration of said first and/or second antibody is at least once per week.

In another embodiment of the invention, the dosage regimen of the first and/or second antibody a comprises administration, at least once per 14 days, of a dose of antibody of at least 5 mg, such as at least 10 mg, e.g. at least 25 mg, such as at least 50 mg, e.g. at least 75 mg, such as at least 100 mg, e.g. at least 150 mg, such as at least 200 mg, e.g. at least 250 mg, such as at least 300 mg e.g. at least 350 mg, such as at least 400 mg, e.g. at least 500 mg, such as at least 750 mg, e.g. at least 1000 mg, such as at least 1250 mg, e.g. at least 1500 mg, such as at least 2000 mg. More preferably, the administration of the antibody or antibodies is at least once per week.

In one embodiment, the antibodies used in the present invention may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours.

As explained above, it has surprisingly been found that combinations of non-cross-blocking anti-EGFR antibodies very potently deposit complement components C1q and C4c on tumor cells, leading to highly effective complement-mediated cell killing (CDC). This induction of CDC leads to a very potent anti-tumor effect, allowing a reduction in the antibody dosage during treatment.

Thus, in preferred embodiments of the method of the invention, the dosage regimens of the first and/or second antibody each individually, or the total dosage for both together, comprise lower dosages than standard dosages for antibody therapy with the same antibody, e.g. lower dosages than standard monotherapy dosages for antibody therapy with the same antibody. Accordingly, in some embodiments, the dosage regimen for said first and/or second antibody is lower than a standard monotherapy dosage regimen for said first and/or second antibody.

When used herein, the term "standard dosage regimen" for a given antibody refers to the dosage regimen recommended for antibodies that have received marketing approval or to a dosage regimen used for phase III clinical studies for an antibody that is in clinical development. For example, a standard dosage regimen for zalutumumab is a dosage of between 4 and 16 mg/kg once weekly.

As explained in more detail below, anti-EGFR therapy is known to cause undesired side-effects, such as rash, due to expression of wild-type EGFR in healthy, non-tumor, tissues. Thus, in particular, when a combination of non-cross-blocking anti-EGFR antibodies is used wherein both antibodies bind an epitope of wild-type EGFR (such as an EGFR epitope which is found on all wild-type-EGFR-expressing cells), then it may be necessary to reduce the dosages of the antibodies as compared to standard therapy in order to avoid toxicity for healthy tissues, due to CDC.

Accordingly, in a preferred embodiment of the method of the invention:
the dosage regimen of said first antibody comprises administration of a total dosage per 14 days of between 0.01 mg/kg and 2 mg/kg, such as between 0.01 mg/kg and 1 mg/kg, e.g. between 0.01 mg/kg and 0.5 mg/kg, such as between 0.01 mg/kg and 0.25 mg/kg, e.g. between 0.01 mg/kg and 0.1 mg/kg, such as between 0.01 mg/kg and 0.05 mg/kg; and/or
the dosage regimen of said second antibody comprises administration of a total dosage per 14 days of between 0.01 mg/kg and 2 mg/kg, such as between 0.01 mg/kg and 1 mg/kg, e.g. between 0.01 mg/kg and 0.5 mg/kg, such as between 0.01 mg/kg and 0.25 mg/kg, e.g. between 0.01 mg/kg and 0.1 mg/kg, such as between 0.01 mg/kg and 0.05 mg/kg.

As explained above, in a particularly interesting embodiment of the method of the invention,
a) the first antibody is an antibody which binds an EGFR epitope which is found in all wild-type-EGFR-expressing cells, b) the second antibody is an antibody, such as ch806, which binds an EGFR epitope which is found in tumor cells, but is not detectable in normal cells, and
c) the dosage regimen is such that substantial CDC is obtained at tumor sites, but substantially no CDC is obtained at non-tumor sites.

In a further embodiment hereof, the first antibody in a) is selected from the group consisting of: zalutumumab, cetuximab, panitumumab, nimotuzumab, matuzumab, 528, LC1006-003, LC1006-005, LC1006-008, LC1006-011 and LC1006-018.

In an even further embodiment hereof, the dosage regimen in c) for said first antibody is a dosage regimen which comprises an equal or a higher dosage than a standard monotherapy dosage regimen for said first antibody, such as a dosage regimen which ensures efficient inhibition of ligand binding at tumor sites. This can e.g. be tested as described in Bleeker, et al (2004) J Immunol, 173, 4699-4707.

In one preferred embodiment, said first antibody is administered at an at least 2 times higher dose than said second antibody, such as an at least 4 times higher dose, e.g. an at least 10 times higher dose, such as an at least 25 times higher dose, e.g. an at least 50 times higher dose than said second antibody.

In another preferred embodiment, said first antibody is administered at a between 2 and 50 times higher dose than said second antibody, such as a between 5 and 20 times higher dose than said second antibody.

In an even further preferred embodiment:
the dosage regimen of the first antibody comprises administration, at least once per 14 days, of a dose of antibody of at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg, and
the dosage regimen of the second antibody comprises administration of a total dosage per 14 days of between 0.1 mg/kg and 1 mg/kg, such as a dose of antibody of between 0.2 mg/kg and 1 mg/kg, e.g. such as a dose of antibody of between 0.1 mg/kg and 0.5 mg/kg, such as a dose of antibody of between 0.2 mg/kg and 0.5 mg/kg.

In another even further preferred embodiment:
the dosage regimen of the first antibody comprises administration, at least once per 14 days, of a dose of antibody of at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg, and
the dosage regimen of the second antibody comprises administration of a total dosage per 14 days of between 0.1 mg/kg and 2 mg/kg, such as a dose of antibody of between 0.2 mg/kg and 1 mg/kg, e.g. such as a dose of antibody of between 0.1 mg/kg and 2 mg/kg, such as a dose of antibody of between 0.1 mg/kg and 0.5 mg/kg.

The first and second antibody may be given simultaneously or sequentially in any order. In one embodiment, both agents are administered on the same day. In a preferred embodiment, the second antibody, e.g. an antibody that binds the same epitope as ch806, is administered at least 15 minutes, such as at least one hour, e.g. at least two hours, such as at least eight hours before the first antibody, preferably between 15 minutes and 6 hours, such as between 1 hour and 4 hours before the first antibody.

In a further embodiment, the total duration of the treatment is at least one month, such as at least two months, e.g. at least four months, such as at least six months.

In some embodiments of the invention, the method of treatment is repeated after an interval of two months or more, such as three months or more, e.g. after six months or more.

In another particularly interesting embodiment of the method of the invention,
a) the first antibody is an antibody which binds an EGFR epitope which is found in all wild-type-EGFR-expressing cells,
b) the second antibody is an antibody which is specific for EGFR-vIII, e.g. binds to EGFR-vIII with a $K_D$ which is at least 10 fold lower, such as at least 50 fold lower, e.g. at least 100 fold lower than the $K_D$ for binding to wild-type EGFR.

Preferably, the dosage regimen is such that substantial CDC is obtained at tumor sites, but substantially no CDC is obtained at non-tumor sites.

Bispecific Antibodies

In a further main aspect, the invention relates to a bispecific antibody comprising a first binding specificity which binds an EGFR epitope which is found on all wild-type-EGFR-expressing cells and a second binding specificity which preferentially binds an EGFR epitope which is found in tumor cells.

In one embodiment, the second binding specificity binds an EGFR epitope which is located within the region comprising residues 273-501 of EGFR, preferably the same EGFR epitope as bound by ch806, wherein said first and second binding specificity are non-cross-blocking.

In another embodiment, the second binding specificity is specific for EGFR-vIII, i.e. does not bind wild-type EGFR.

In a further embodiment, the antibody comprises a first binding specificity which binds an epitope selected from the group consisting of:
the EGFR epitope bound by zalutumumab,
the EGFR epitope bound by cetuximab,
the EGFR epitope bound by panitumumab,
the EGFR epitope bound by nimotuzumab,
the EGFR epitope bound by matuzumab,
the EGFR epitope bound by 528,
the EGFR epitope bound by LC1006-003,
the EGFR epitope bound by LC1006-005,
the EGFR epitope bound by LC1006-008,
the EGFR epitope bound by LC1006-011, and
the EGFR epitope bound by LC1006-018.

In a further aspect, the invention relates to a bispecific antibody as defined above for use as a medicament.

In an even further aspect, the invention relates to a bispecific antibody as defined above for use as a medicament for the treatment of cancer.

In a yet even further aspect, the invention relates to the use of a bispecific antibody as defined above for the preparation of a medicament for the treatment of cancer.

In a similar aspect, the invention relates to a method for the treatment of cancer comprising administration of a bispecific antibody as defined above.

In one embodiment, said cancer is selected from the group consisting of: breast cancer, bladder cancer, uterine/cervical cancer, esophageal cancer, pancreatic cancer, colorectal cancer, kidney cancer, ovarian cancer, prostate cancer, head and neck cancer, non-small cell lung cancer and stomach cancer.

As non-limiting examples, treatment with the bispecific antibody according to the present invention may be provided as a daily dosage in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses of every 24, 12, 8, 6, 4, or 2 hours, or any combination thereof.

In a preferred embodiment of the method of the invention, the dosage regimen of the bispecific anti-EGFR antibody comprises administration, at least once per 14 days, of a dose of antibody of at least 0.1 mg/kg, such as at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg. More preferably, the administration of the bispecific anti-EGFR antibody is at least once per week.

In another embodiment of the invention, the dosage regimen of the bispecific anti-EGFR antibody comprises administration, at least once per 14 days, of a dose of antibody of at least 5 mg, such as at least 10 mg, e.g. at least 25 mg, such as at least 50 mg, e.g. at least 75 mg, such as at least 100 mg, e.g. at least 150 mg, such as at least 200 mg, e.g. at least 250 mg, such as at least 300 mg e.g. at least 350 mg, such as at least 400 mg, e.g. at least 500 mg, such as at least 750 mg, e.g. at least 1000 mg, such as at least 1250 mg, e.g. at least 1500 mg, such as at least 2000 mg. More preferably, the administration of the bispecific anti-EGFR antibody is at least once per week.

Novel Anti-EGFR Antibodies

In a further aspect, the invention relates to an isolated monoclonal antibody which binds to human EGFR, wherein the antibody binds to the same epitope on EGFR as an antibody selected from the group consisting of:
an antibody having a heavy chain variable region having the amino acid sequence shown in SEQ ID NO: 7 and a light chain variable region having the amino acid sequence shown in SEQ ID NO: 8;
an antibody having a heavy chain variable region having the amino acid sequence shown in SEQ ID NO: 9 and a light chain variable region having the amino acid sequence shown in SEQ ID NO: 10;
an antibody having a heavy chain variable region having the amino acid sequence shown in SEQ ID NO: 9 and a light chain variable region having the amino acid sequence shown in SEQ ID NO: 11;
an antibody having a heavy chain variable region having the amino acid sequence shown in SEQ ID NO: 12 and a light chain variable region having the amino acid sequence shown in SEQ ID NO: 13;
an antibody having a heavy chain variable region having the amino acid sequence shown in SEQ ID NO: 14 and a light chain variable region having the amino acid sequence shown in SEQ ID NO: 15;
an antibody having a heavy chain variable region having the amino acid sequence shown in SEQ ID NO: 14 and a light chain variable region having the amino acid sequence shown in SEQ ID NO: 16; and
an antibody having a heavy chain variable region having the amino acid sequence shown in SEQ ID NO: 17 and a light chain variable region having the amino acid sequence shown in SEQ ID NO: 18.

In one embodiment, the antibody is selected from the group consisting of:
- an antibody having a heavy chain CDR3 region identical to the CDR3 region of the heavy chain sequence shown in SEQ ID NO: 7;
- an antibody having a heavy chain CDR3 region identical to the CDR3 region of the heavy chain sequence shown in SEQ ID NO: 9;
- an antibody having a heavy chain CDR3 region identical to the CDR3 region of the heavy chain sequence shown in SEQ ID NO: 12;
- an antibody having a heavy chain CDR3 region identical to the CDR3 region of the heavy chain sequence shown in SEQ ID NO: 14; and
- an antibody having a heavy chain CDR3 region identical to the CDR3 region of the heavy chain sequence shown in SEQ ID NO: 17.

In a further embodiment, the antibody is selected from the group consisting of:
- an antibody comprising CDR sequences that are identical to the CDR sequences of an antibody comprising a heavy chain variable region having the amino acid sequence shown in SEQ ID NO: 7 and a light chain variable region having the amino acid sequence shown in SEQ ID NO: 8;
- an antibody comprising CDR sequences that are identical to the CDR sequences of an antibody comprising a heavy chain variable region having the amino acid sequence shown in SEQ ID NO: 9 and a light chain variable region having the amino acid sequence shown in SEQ ID NO: 10;
- an antibody comprising CDR sequences that are identical to the CDR sequences of an antibody comprising a heavy chain variable region having the amino acid sequence shown in SEQ ID NO: 9 and a light chain variable region having the amino acid sequence shown in SEQ ID NO: 11;
- an antibody comprising CDR sequences that are identical to the CDR sequences of an antibody comprising a heavy chain variable region having the amino acid sequence shown in SEQ ID NO: 12 and a light chain variable region having the amino acid sequence shown in SEQ ID NO: 13;
- an antibody comprising CDR sequences that are identical to the CDR sequences of an antibody comprising a heavy chain variable region having the amino acid sequence shown in SEQ ID NO: 14 and a light chain variable region having the amino acid sequence shown in SEQ ID NO: 15;
- an antibody comprising CDR sequences that are identical to the CDR sequences of an antibody comprising a heavy chain variable region having the amino acid sequence shown in SEQ ID NO: 14 and a light chain variable region having the amino acid sequence shown in SEQ ID NO: 16; and
- an antibody comprising CDR sequences that are identical to the CDR sequences of an antibody comprising a heavy chain variable region having the amino acid sequence shown in SEQ ID NO: 17 and a light chain variable region having the amino acid sequence shown in SEQ ID NO: 18.

In an even further embodiment, the antibody is selected from the group consisting of:
- an antibody having a heavy chain variable region having the amino acid sequence shown in SEQ ID NO: 7 and a light chain variable region having the amino acid sequence shown in SEQ ID NO: 8;
- an antibody having a heavy chain variable region having the amino acid sequence shown in SEQ ID NO: 9 and a light chain variable region having the amino acid sequence shown in SEQ ID NO: 10;
- an antibody having a heavy chain variable region having the amino acid sequence shown in SEQ ID NO: 9 and a light chain variable region having the amino acid sequence shown in SEQ ID NO: 11;
- an antibody having a heavy chain variable region having the amino acid sequence shown in SEQ ID NO: 12 and a light chain variable region having the amino acid sequence shown in SEQ ID NO: 13;
- an antibody having a heavy chain variable region having the amino acid sequence shown in SEQ ID NO: 14 and a light chain variable region having the amino acid sequence shown in SEQ ID NO: 15;
- an antibody having a heavy chain variable region having the amino acid sequence shown in SEQ ID NO: 14 and a light chain variable region having the amino acid sequence shown in SEQ ID NO: 16; and
- an antibody having a heavy chain variable region having the amino acid sequence shown in SEQ ID NO: 17 and a light chain variable region having the amino acid sequence shown in SEQ ID NO: 18.

In an even further embodiment, the antibody is an IgG1, IgA, IgE, IgM, IgG4 or IgD antibody. In an even further embodiment, the antibody is a human antibody. In an even further embodiment, the antibody inhibits EGFR ligand binding to human EGFR, preferably by at least about 50%. In an even further embodiment, the antibody binds to human EGFR with an equilibrium association constant ($K_A$) of at least about $10^8$ $M^{-1}$, preferably an equilibrium associated constant ($K_A$) of at least $10^9$ $M^{-1}$.

In a further aspect, the invention relates to a transfectoma comprising nucleic acids encoding a human heavy chain and a human light chain, wherein the transfectoma produces a detectable amount of the antibody described herein above.

In a further aspect, the invention relates to a composition comprising the antibody described herein above and a pharmaceutically acceptable carrier.

In an even further aspect, the invention relates to the antibody described herein above for use as a medicament, preferably for use a medicament for the treatment of cancer.

In an even further aspect, the invention relates to method of treating or preventing a disease mediated by expression of EGFR, comprising administration to a subject the antibody of the invention in an amount effective to treat or prevent the EGFR-mediated disease. In one embodiment, the disease is cancer. In another embodiment, the method further comprises the co-administration of a therapeutic agent.

Undesired Side-Effects

Undesired side-effects common to anti-EGFR agents include dermatological side-effects, such as papulopustolar rash, usually on the face, upper back and upper torso. Rash generally develops in a dose-dependent manner.

In some of the above described embodiments of the method of the invention, anti-EGFR antibodies are given at a lower dose than what is usual for anti-EGFR antibody therapy. In such embodiments, rash may be reduced.

Rash can be quantified using the grades defined in the Common Terminology Criteria for Adverse Events (CTCAE), e.g. version 3.0, under the term "Rash/desquamation". As desquamation is not a common side effect of treatment with EGFR inhibition therapy, the patient's skin rash may be scored based on rash only. The CTCAE criterion for rash/desquamation can therefore suitably be adjusted as follows:

| CTCAE Grade | Description Term Rash |
|---|---|
| 1 | Macular or papular eruption or erythema without associated symptoms |
| 2 | Macular or papular eruption or erythema with pruritus or other associated symptoms |
| 3 | Widespread and confluent erythroderma or macular, papular, or vesicular eruption |
| 4 | Generalized exfoliative, ulcerative, or bullos dermatitis |
| 5 | Death |

A reduction in rash, e.g. of 10%, when used herein indicates is a statistically significant reduction of 10% in the total CTCAE score of a representative population, as compared to standard therapy.

In a preferred embodiment of the method or use of the invention, the rash is reduced by at least 10%, such as at least 20%, e.g. at least 30%, such as at least 40%, e.g. at least 50%, such as at least 60%, e.g. at least 70%, such as at least 80%, e.g. at least 90%, such as least 95%, as compared to standard therapy with the first anti-EGFR antibody, e.g. zalutumumab, cetuximab or panitumumab, and/or compared to standard therapy for the second anti-EGFR antibody.

Compositions

Formulation, Additives and Mode-Of-Administration

The antibodies used in the present invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutically acceptable carriers or diluents as well as any other known adjuvants and excipients should be suitable for the chosen composition of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) on antigen binding.

A pharmaceutical composition of the present invention may also include diluents, fillers, salts, buffers, detergents (e.g., a nonionic detergent, such as Tween-80), stabilizers, stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a composition in vivo and in vitro are well known in the art and may be selected by those of ordinary skill in the art.

The antibodies may be administered via any suitable route, such as an oral, nasal, inhalable, topical (including buccal, transdermal and sublingual), rectal, vaginal and/or parenteral route.

In one embodiment of the method of the present invention, one or both antibodies are administered parenterally, preferably intravenously.

The phrases "parenteral administration" and "administered parenterally" as used herein means modes of administration other than enteral and topical administration, usually by injection, and include intratumoral, epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. In a preferred embodiment, the pharmaceutical composition is administered by intravenous or subcutaneous injection or infusion.

In another embodiment, the antibodies used in the present invention are administered in crystalline form by subcutaneous injection, cf. Yang et al., PNAS USA 100(12), 6934-6939 (2003).

The pharmaceutical compositions of the present invention may be administered with medical devices known in the art. For example, in one embodiment, a pharmaceutical composition of the present invention may be administered with a needleless hypodermic injection device, such as the devices disclosed in U.S. Pat. No. 5,399,163, U.S. Pat. No. 5,383,851, U.S. Pat. No. 5,312,335, U.S. Pat. No. 5,064,413, U.S. Pat. No. 4,941,880, U.S. Pat. No. 4,790,824, or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The pharmaceutical compositions containing the antibodies may conveniently be presented in unit dosage form and may be prepared by any methods known in the art of pharmacy. The amount of active ingredient which may be combined with a carrier material to produce a single dosage form will vary depending upon the subject being treated, and the particular mode of administration. The amount of active ingredient which may be combined with a carrier material to produce a single dosage form will generally be that amount of the composition which produces a therapeutic effect. Generally, out of one hundred percent, this amount will range from about 0.01% to about 99% of active ingredient, such as from about 0.1% to about 70%, for instance from about 1% to about 30%.

Regardless of the route of administration selected, the compositions used in the present invention, which may be used in the form of a pharmaceutically acceptable salt or in a suitable hydrated form are formulated into pharmaceutically acceptable dosage forms by conventional methods known to those of skill in the art. A "pharmaceutically acceptable salt" refers to a salt that retains the desired biological activity of the parent compound and does not impart any undesired toxicological effects (see for instance Berge, S. M. et al., J. Pharm. Sci. 66, 1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous acids and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound used in the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions used in the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions used in the present invention may also comprise isotonicity agents, such as sugars, polyalcohols such as mannitol, sorbitol, glycerol or sodium chloride in the compositions Pharmaceutically acceptable diluents include saline and aqueous buffer solutions. The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. Compounds used in the present invention may for instance be admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. Other examples of adjuvants are QS21, GM-CSF, SRL-172, histamine dihydrochloride, thymocartin, Tio-TEPA, monophosphoryl-lipid A/micobacteria compositions, alum, incomplete Freund's adjuvant, montanide ISA, ribi adjuvant system, TiterMax adjuvant, syntex adjuvant formulations, immune-stimulating complexes (ISCOMs), gerbu adjuvant, CpG oligodeoxynucleotides, lipopolysaccharide, and polyinosinic:polycytidylic acid.

Prevention of presence of microorganisms may be ensured both by sterilization procedures and by the inclusion of various antibacterial and antifungal agents, for example, paraben, chlorobutanol, phenol, sorbic acid, and the like. In addition, prolonged absorption of the injectable pharmaceutical form may be brought about by the inclusion of agents which delay absorption such as aluminum monostearate and gelatin.

Pharmaceutical compositions used in the present invention may also include a suitable salt therefore. Any suitable salt, such as an alkaline earth metal salt in any suitable form (e.g., a buffer salt), may be used in the stabilization of the compound used in the present invention. Suitable salts typically include sodium chloride, sodium succinate, sodium sulfate, potassium chloride, magnesium chloride, magnesium sulfate, and calcium chloride. In one embodiment, an aluminum salt is used to stabilize a compound used in the present invention in a pharmaceutical composition of the present invention, which aluminum salt also may serve as an adjuvant when such a composition is administered to a patient.

Pharmaceutical compositions used in the present invention may be in a variety of suitable forms. Such forms include, for example, liquid, semi-solid and solid dosage forms, such as liquid solutions (e.g., injectable and infusible solutions), dispersions or suspensions, emulsions, microemulsions, gels, creams, granules, powders, tablets, pills, powders, liposomes, dendrimers and other nanoparticles (see for instance Baek et al., Methods Enzymol. 362, 240-9 (2003), Nigavekar et al., Pharm Res. 21(3), 476-83 (2004), microparticles, and suppositories.

The compounds used in the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. For example, the blood-brain barrier (BBB) excludes many highly hydrophilic compounds. To ensure that the therapeutic compounds of the present invention cross the BBB (if desired), they may be formulated, for example, in liposomes. For methods of manufacturing liposomes, see for instance U.S. Pat. No. 4,522,811, U.S. Pat. No. 5,374,548 and U.S. Pat. No. 5,399,331. The liposomes may comprise one or more moieties which are selectively transported into specific cells or organs, thus enhance targeted drug delivery (see for instance V. V. Ranade J. Clin. Pharmacol. 29, 685 (1989)). Exemplary targeting moieties include folate or biotin (see for instance U.S. Pat. No. 5,416,016), mannosides (Umezawa et al., Biochem. Biophys. Res. Commun. 153, 1038 (1988)), antibodies (P. G. Bloeman et al., FEBS Lett. 357, 140 (1995), M. Owais et al., Antimicrob. Agents Chemother. 39, 180 (1995)), surfactant protein A receptor (Briscoe et al., Am. J. Physiol. 1233, 134 (1995)), different species of which may comprise the pharmaceutical compositions of the present inventions, as well as components of the invented molecules, p120 (Schreier et al., J. Biol. Chem. 269, 9090 (1994)), see also K. Keinanen, M. L. Laukkanen, FEBS Lett. 346, 123 (1994) and J. J. Killion, I. J. Fidler, Immunomethods 4, 273 (1994).

In one embodiment of the present invention, the compounds of the present invention are formulated in liposomes. In a further embodiment, the liposomes include a targeting moiety. In a further embodiment, the compounds in the liposomes are delivered by bolus injection to a site proximal to the desired area, e.g., the site of inflammation or infection, or the site of a tumor. The composition should be fluid to the extent that easy syringability exists. It should be stable under the conditions of manufacture and storage and should be preserved against the contaminating action of microorganisms such as bacteria and fungi.

In one embodiment, the compounds of the present invention may be formulated to prevent or reduce their transport across the placenta. This may be done by methods known in the art, e.g., by PEGylation of the compounds or by use of F(ab')$_2$ fragments. Further reference can be made to Cunningham-Rundles C et al., J Immunol Methods. 152, 177-190 (1992) and to Landor M., Ann Allergy Asthma Immunol 74, 279-283 (1995).

Tumors to be Treated

In one embodiment of the method or use of the invention, said tumor is selected from the group consisting of: breast cancer tumor, bladder cancer tumor, uterine/cervical cancer tumor, esophageal cancer tumor, pancreatic cancer tumor, colon cancer tumor, colorectal cancer tumor, kidney cancer tumor, ovarian cancer tumor, prostate cancer tumor, renal cancer, head and neck cancer (SCCHN) tumor, non-small cell lung cancer (NSCLC) tumor, stomach cancer tumor, glioblastoma, pons glioma, high grade astrocytoma and other EGFR-expressing tumors.

In a further embodiment of the method or use of the invention, said tumor is a resistant or relapsed high-grade glioma, such as a diffuse, intrinsic or pontine glioma.

In one embodiment of the method or use of the invention, the EGFR levels in the tumor cells to be treated are not below threshold for obtaining ADCC when treated with the first antibody without co-administration of the second antibody. For example, in one embodiment, the EGFR levels in the tumor or tumor cells may be sufficient for obtaining ADCC in vivo when treated with zalutumumab with a standard dosage of between 2 and 20 mg/kg once per week or per 14 days without co-administration of a second antibody.

In a further embodiment of the method or use of the invention, said tumor is an EGFRvIII-expressing tumor.

In a further embodiment of the method or use of the invention, the human being in need of the treatment is a human being who is likely to have tumors that exhibit EGFRvIII expression or has been diagnosed to have such tumors. This may be determined using standard diagnostic procedures well-known in the art, e.g. similar those described on pages 26-31 of WO 2007123661 (incorporated herein by reference).

Combination Therapy

In further embodiments, the present invention provides methods which comprise administration of anti-EGFR antibodies combined with one or more additional therapeutic agents as described below.

In one such embodiment, the method comprises administration of a third antibody, such as an anti-EGFR antibody, wherein said third antibody is not cross-blocking with either of said first and second antibody.

In a further embodiment hereof:
said first antibody is an antibody which binds the same EGFR epitope as LC1006-018, and
said second antibody is selected from the group consisting of:
an antibody which binds the same EGFR epitope as zalutumumab,
an antibody which binds the same EGFR epitope as cetuximab,
an antibody which binds the same EGFR epitope as panitumumab,
an antibody which binds the same EGFR epitope as 528, and
said third antibody is selected from the group consisting of:
an antibody which binds the same EGFR epitope as LC1006-003,
an antibody which binds the same EGFR epitope as LC1006-005,
an antibody which binds the same EGFR epitope as LC1006-008, and
an antibody which binds the same EGFR epitope as LC1006-011.

In a further embodiment:
said first antibody is an antibody which binds the same EGFR epitope as LC1006-018, and
said second antibody is selected from the group consisting of:
an antibody which binds the same EGFR epitope as zalutumumab,
an antibody which binds the same EGFR epitope as cetuximab,
an antibody which binds the same EGFR epitope as panitumumab,
an antibody which binds the same EGFR epitope as 528, and
said third antibody is an antibody which binds the same EGFR epitope as ch806.

In a further embodiment:
said first antibody is an antibody which binds the same EGFR epitope as LC1006-018, and
said second antibody is selected from the group consisting of:
an antibody which binds the same EGFR epitope as zalutumumab,
an antibody which binds the same EGFR epitope as cetuximab,
an antibody which binds the same EGFR epitope as panitumumab,
an antibody which binds the same EGFR epitope as 528, and
said third antibody is an antibody which binds the same EGFR epitope as MR1-1.

In a further embodiment, the method of the invention comprises administration of one or more further therapies selected from chemotherapeutic agents, immunosuppressive agents, anti-inflammatory agents, anti-psoriasis agents, radiation therapy, hyperthermia, transplantation, surgery, sunlight therapy and phototherapy.

In a further embodiment, the method comprises administration of one or more further therapies selected from the group consisting of nitrogen mustards, aziridines, alkyl sulfonates, nitrosoureas, platinum complexes, non-classical alkylating agents, folate analogs, purine analogs, adenosine analogs, pyrimidine analogs, substituted ureas, antitumor antibiotics, epipodophyllotoxins, microtubule agents, camptothecin analogs, enzymes, cytokines, monoclonal antibodies, recombinant toxins and immunotoxins, cancer gene therapies and cancer vaccines.

In an even further embodiment, the method comprises administration of one or more further therapies selected from the group consisting of immunosuppressive antibodies against MHC, CD2, CD3, CD4, CD7, CD28, B7, CD40, CD45, IFN-gamma, TNF-alpha, IL-4, IL-5, IL-6R, IL-7, Il-8, IL-10, CD11a, CD20, and CD58 or antibodies against their ligands, soluble IL-15R, and IL-10.

In a yet further embodiment, the method comprises administration of one or more further therapies selected from the group consisting of cyclosporine, azathioprine, mycophenolic acid, mycophenolate mofetil, corticosteroids, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, transplantation.

In an even further embodiment, the method comprises administration of one or more further therapies selected from the group consisting of aspirin, other salicylates, steroidal drugs, NSAIDs (nonsteroidal anti-inflammatory drugs), Cox-2 inhibitors, and DMARDs (disease modifying antirheumatic drugs).

In another embodiment, the method comprises administration of one or more further therapies selected from the group consisting of coal tar, A vitamin, anthralin, calcipotrien, tarazotene, corticosteroids, methotrexate, retinoids, cyclosporine, etanercept, alefacept, efaluzimab, 6-thioguanine, mycophenolate mofetil, tacrolimus (FK-506), hydroxyurea, sunlight therapy, and phototherapy.

In a preferred embodiment, the method comprises administration of one or more further therapies selected from: platinum derivatives, such as cisplatin or carboplatin; fluorouracil; paclitaxel, docetaxel and radiotherapy.

In a further preferred embodiment of the method of the invention, in particular when one or both of the antibodies sued are anti-EGFR antibodies, the method further comprises administration one or more tyrosine kinase inhibitors, such as gefitinib, erlotinib, XL-647, JNJ-26483327, vandetanib, BMS-599626, AZD-9935, AEE-788, BIBW-2992, ISU-101, HMPL-010, ON-012380, EKI-785, TX-2036, EHT-102, KI-6783, KI-6896 and LFM-A12.

Further Aspects and Embodiments of the Invention

1. A method for the treatment of a tumor comprising combined administration, to a human being in need thereof, of a first antibody and a second antibody, wherein
said first antibody binds EGFR,
said second antibody binds EGFR, and
said first and second antibody are non-cross-blocking.

2. The method of embodiment 1, wherein the dosage regimen is such that substantial CDC is obtained at the tumor site.

3. The method of any of the preceding embodiments, wherein said first antibody is an antibody which is capable of binding an EGFR epitope which is found on all wild-type-EGFR-expressing cells.

4. The method of any of the preceding embodiments, wherein said first antibody binds to human EGFR with an equilibrium dissociation constant ($K_D$) of at most $10^{-8}$ M, preferably at most $10^{-10}$ M.

5. The method of any of the preceding embodiments, wherein said first antibody is an antibody which is capable of inducing ADCC at the tumor site in the absence of said second antibody.

6. The method of any of the preceding embodiments, wherein said first antibody is selected from the group consisting of:
an antibody which binds the same EGFR epitope as zalutumumab,
an antibody which binds the same EGFR epitope as cetuximab,
an antibody which binds the same EGFR epitope as panitumumab,
an antibody which binds the same EGFR epitope as nimotuzumab,
an antibody which binds the same EGFR epitope as matuzumab, and
an antibody which binds the same EGFR epitope as 528.

7. The method of any of the preceding embodiments, wherein said first antibody is selected from the group consisting of:
an antibody which comprises the same heavy chain CDR3 sequence as zalutumumab and binds the same EGFR epitope as zalutumumab,
an antibody which comprises the same heavy chain CDR3 sequence as cetuximab and binds the same EGFR epitope as cetuximab,
an antibody which comprises the same heavy chain CDR3 sequence as panitumumab and binds the same EGFR epitope as panitumumab,
an antibody which comprises the same heavy chain CDR3 sequence as nimotuzumab and binds the same EGFR epitope as nimotuzumab,
an antibody which comprises the same heavy chain CDR3 sequence as matuzumab and binds the same EGFR epitope as matuzumab, and
an antibody which comprises the same heavy chain CDR3 sequence as 528 and binds the same EGFR epitope as 528.

8. The method of any of the preceding embodiments, wherein said first antibody is selected from the group consisting of:
an antibody which comprises the same 6 CDR sequences as zalutumumab,
an antibody which comprises the same 6 CDR sequences as cetuximab,
an antibody which comprises the same 6 CDR sequences as panitumumab,
an antibody which comprises the same 6 CDR sequences as nimotuzumab,
an antibody which comprises the same 6 CDR sequences as matuzumab, and
an antibody which comprises the same 6 CDR sequences as 528.

9. The method of any of the preceding embodiments, wherein said first antibody is selected from the group consisting of: zalutumumab, cetuximab, panitumumab, nimotuzumab, matuzumab and 528.

10. The method of embodiment 6, wherein said first antibody is an antibody which binds the same EGFR epitope as zalutumumab and said second antibody is selected from the group consisting of:
   an antibody which binds the same EGFR epitope as nimotuzumab, and
   an antibody which binds the same EGFR epitope as matuzumab.

11. The method of embodiment 6, wherein said first antibody is an antibody which binds the same EGFR epitope as cetuximab and said second antibody is an antibody which binds the same EGFR epitope as matuzumab.

12. The method of embodiment 6, wherein said first antibody is an antibody which binds the same EGFR epitope as panitumumab and said second antibody is an antibody which binds the same EGFR epitope as matuzumab.

13. The method of embodiment 6, wherein said first antibody is an antibody which binds the same EGFR epitope as nimotuzumab and said second antibody is an antibody which binds the same EGFR epitope as matuzumab.

14. The method of embodiment 13, wherein said second antibody is capable of binding an EGFR epitope which is found in tumor cells, but is not detectable in normal cells.

15. The method of embodiment 14, wherein said EGFR epitope does not demonstrate any amino acid sequence alterations or substitutions as compared to wild-type EGFR.

16. The method of embodiment 14 or 15, wherein said second antibody binds an EGFR epitope which is located within the region comprising residues 273-501 of EGFR.

17. The method of embodiments 14 to 16, wherein said second antibody binds an EGFR epitope, which is located within the region comprising residues 287-302 of EGFR.

18. The method of any of embodiments 14 to 17, wherein said second antibody is cross-blocking with ch806.

19. The method of any of embodiments 14 to 18, wherein said second antibody binds the same EGFR epitope as ch806.

20. The method of embodiment 19, wherein the second antibody comprises SEQ ID NO:3 and optionally one or more or all of SEQ ID NO:1, 2, 4, 5 and 6.

21. The method of embodiment 19, wherein the second antibody is ch806.

22. The method of embodiment 13, wherein the second antibody is MR1-1.

23. The method of any of embodiments 1 to 9, wherein said second antibody is specific for EGFR-vIII.

24. The method of any of the preceding embodiments, wherein the first and/or the second antibody is a human antibody.

25. The method of any of the preceding embodiments, wherein the dosage regimen of said first antibody comprises administration, at least once per 14 days, of a dosage of antibody of at least 0.1 mg/kg, such as at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg.

26. The method of any of the preceding embodiments, wherein the dosage regimen of said second antibody comprises administration, at least once per 14 days, of a dosage of antibody of at least 0.1 mg/kg, such as at least 0.25 mg/kg, e.g. at least 0.5 mg/kg, such as at least 1 mg/kg, e.g. at least 1.5 mg/kg, such as at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg.

27. The method of any of embodiments 25 or 26, wherein the administration of said first and second antibody is at least once per week.

28. The method of any of embodiments 1 to 24, wherein the dosage regimen for said first antibody is lower than a standard dosage regimen for said first antibody.

29. The method of any of embodiments 1 to 24, wherein the dosage regimen of said first antibody comprises administration of a total dosage per 14 days of between 0.01 mg/kg and 2 mg/kg, such as between 0.01 mg/kg and 1 mg/kg, e.g. between 0.01 mg/kg and 0.5 mg/kg, such as between 0.01 mg/kg and 0.25 mg/kg, e.g. between 0.01 mg/kg and 0.1 mg/kg, such as between 0.01 mg/kg and 0.05 mg/kg.

30. The method of any of embodiments 1 to 24 or 28 or 29, wherein the dosage regimen for said second antibody is lower than a standard dosage regimen for said second antibody.

31. The method of any of embodiments 1 to 24 or 28 or 29, wherein the dosage regimen of said second antibody comprises administration of a total dosage per 14 days of between 0.01 mg/kg and 2 mg/kg, such as between 0.01 mg/kg and 1 mg/kg, e.g. between 0.01 mg/kg and 0.5 mg/kg, such as between 0.01 mg/kg and 0.25 mg/kg, e.g. between 0.01 mg/kg and 0.1 mg/kg, such as between 0.01 mg/kg and 0.05 mg/kg.

32. The method of any of the preceding embodiments, wherein the dosage regimen is such that substantially no CDC is obtained at non-tumor sites.

33. The method of any of the preceding embodiments, wherein the dosage regimen ensures efficient inhibition of ligand binding at tumor sites.

34. The method of any of embodiments 13 to 23 or 30 to 34, wherein the dosage regimen for said first antibody is a dosage regimen which comprises an equal or a higher dosage than a standard dosage regimen for said first antibody.

35. The method of any of embodiments 13 to 23 or 30 to 34, wherein said first antibody is administered at an at least 2 times higher dose than said second antibody, such as an at least 4 times higher dose, e.g. an at least 10 times higher dose, such as an at least 25 times higher dose, e.g. an at least 50 times higher dose than said second antibody.

36. The method of embodiment 35, wherein said first antibody is administered at a between 2 and 50 times higher dose than said second antibody, such as a between 5 and 20 times higher dose than said second antibody.

37. The method of any of embodiments 13 to 23 or 30 to 34, wherein:
   the dosage regimen of the first antibody comprises administration, at least once per 14 days, of a dose of antibody of at least 2 mg/kg, e.g. at least 3 mg/kg, such as at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg, and
   the dosage regimen of the second antibody comprises administration of a total dosage per 14 days of between 0.1 mg/kg and 1 mg/kg, such as a dose of antibody of between 0.2 mg/kg and 1 mg/kg, e.g. such as a dose of antibody of between 0.1 mg/kg and 0.5 mg/kg, such as a dose of antibody of between 0.2 mg/kg and 0.5 mg/kg.

38. The method of any of embodiments 13 to 23 or 30 to 34, wherein:
the dosage regimen of the first antibody comprises administration, at least once per 14 days, of a dose of antibody of at least 4 mg/kg, e.g. at least 5 mg/kg, such as at least 6 mg/kg, e.g. at least 7 mg/kg, such as at least 8 mg/kg, e.g. at least 9 mg/kg, such as at least 10 mg/kg, e.g. at least 12 mg/kg, such as at least 15 mg/kg, e.g. at least 20 mg/kg, and the dosage regimen of the second antibody comprises administration of a total dosage per 14 days of between 0.1 mg/kg and 2 mg/kg, such as a dose of antibody of between 0.2 mg/kg and 1 mg/kg, e.g. such as a dose of antibody of between 0.1 mg/kg and 2 mg/kg, such as a dose of antibody of between 0.1 mg/kg and 0.5 mg/kg.

39. The method of any of the preceding embodiments, wherein said second antibody is administered at least 15 minutes, such as at least one hour, e.g. at least two hours, such as at least eight hours before the first antibody, preferably between 15 minutes and 6 hours, such as between 1 hour and 4 hours before said first antibody.

40. The method of any of the preceding embodiments, wherein the total duration of the treatment is at least one month, such as at least two months, e.g. at least four months, such as at least six months.

41. The method of any of the preceding embodiments, wherein said first and/or second antibody is administered parenterally, preferably intravenously.

42. The method of any of the preceding embodiments, further comprising administration of a third antibody, wherein said third antibody is not cross-blocking with either of said first and second antibody.

43. The method of any of the preceding embodiments, wherein said tumor is selected from the group consisting of: breast cancer tumor, bladder cancer tumor, uterine/cervical cancer tumor, esophageal cancer tumor, pancreatic cancer tumor, colorectal cancer tumor, kidney cancer tumor, ovarian cancer tumor, prostate cancer tumor, head and neck cancer tumor, non-small cell lung cancer tumor, stomach tumor, glioblastoma and other EGFR-expressing tumors.

44. The method of any of the preceding embodiments, wherein the EGFR levels in the tumor cells to be treated are not below threshold for obtaining ADCC when treated with the first antibody without co-administration of the second antibody.

45. The method of any of the preceding embodiments, comprising administration of one or more further therapies selected from chemotherapeutic agents, immunosuppressive agents, anti-inflammatory agents, anti-psoriasis agents, radiation therapy, hyperthermia, transplantation, surgery, sunlight therapy, and phototherapy.

46. The method of any of the preceding embodiments, comprising administration of one or more further therapies selected from the group consisting of nitrogen mustards, aziridines, alkyl sulfonates, nitrosoureas, platinum complexes, non-classical alkylating agents, folate analogs, purine analogs, adenosine analogs, pyrimidine analogs, substituted ureas, antitumor antibiotics, epipodophyllotoxins, microtubule agents, camptothecin analogs, enzymes, cytokines, monoclonal antibodies, recombinant toxins and immunotoxins, cancer gene therapies, and cancer vaccines.

47. The method of any of the preceding embodiments, comprising administration of one or more further therapies selected from the group consisting of immunosuppressive anti-bodies against MHC, CD2, CD3, CD4, CD7, CD28, B7, CD40, CD45, IFN-gamma, TNF-alpha, IL-4, IL-5, IL-6R, IL-7, IL-10, CD11a, CD20, and CD58 or antibodies against their ligands, soluble IL-15R, and IL-10.

48. The method of any of the preceding embodiments, comprising administration of one or more further therapies selected from the group consisting of cyclosporine, azathioprine, mycophenolic acid, mycophenolate mofetil, corticosteroids, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, transplantation, and surgery.

49. The method of any of the preceding embodiments, comprising administration of one or more further therapies selected from the group consisting of aspirin, other salicylates, steroidal drugs, NSAIDs (nonsteroidal anti-inflammatory drugs), Cox-2 inhibitors, and DMARDs (disease modifying antirheumatic drugs).

50. The method of any of the preceding embodiments, comprising administration of one or more further therapies selected from the group consisting of coal tar, A vitamin, anthralin, calcipotrien, tarazotene, corticosteroids, methotrexate, retinoids, cyclosporine, etanercept, alefacept, efaluzimab, 6-thioguanine, mycophenolate mofetil, tacrolimus (FK-506), hydroxyurea, sunlight therapy, and phototherapy.

51. The method of any of the preceding embodiments, comprising administration of one or more tyrosine kinase inhibitors, such as gefitinib, erlotinib, XL-647, JNJ-26483327, vandetanib, BMS-599626, AZD-9935, AEE-788, BIBW-2992, ISU-101, HMPL-010, ON-012380, EKI-785, TX-2036, EHT-102, KI-6783, KI-6896 and LFM-A12.

52. The method of any of the preceding embodiments, wherein said tumor is an EGFRvIII-expressing tumor.

53. The method of any of the preceding embodiments, wherein the human being in need of the treatment is a human being who has been diagnosed to have tumors that exhibit EGFRvIII expression.

54. A first antibody for use in the treatment of a tumor in combination with a second antibody, wherein
said first antibody binds EGFR,
said second antibody binds EGFR, and
said first and second antibody are non-cross-blocking.

55. The first antibody of embodiment 54, wherein the first antibody, the second antibody and/or the treatment comprises one or more of the further features of any one of embodiment 2 to 53.

56. A second antibody for use in the treatment of a tumor in combination with a first antibody, wherein
said first antibody binds EGFR,
said second antibody binds EGFR, and
said first and second antibody are non-cross-blocking.

57. The second antibody of embodiment 56, wherein the first antibody, the second antibody and/or the treatment comprises one or more of the further features of any one of embodiment 2 to 53.

58. Use of a first antibody and a second antibody for the preparation of a medicament for the treatment of a tumor, wherein
said first antibody binds EGFR,
said second antibody binds EGFR, and
said first and second antibody are non-cross-blocking.

59. The use of embodiment 58, comprising one or more of the further features of any one of embodiment 2 to 53.

60. A bispecific antibody comprising a first binding specificity which binds an EGFR epitope which is found on all wild-type-EGFR-expressing cells and a second binding specificity which binds an EGFR epitope which is found in tumor cells, but is not detectable in normal cells.

61. The bispecific antibody of embodiment 60, wherein the second binding specificity binds an EGFR epitope is located within the region comprising residues 273-501 of EGFR, preferably the same EGFR epitope as bound by ch806, wherein said first and second binding specificity are non-cross-blocking.

62. The bispecific antibody of embodiment 61, wherein the second binding specificity is specific for EGFR-vIII.

63. The bispecific antibody of any one of embodiments 60 to 62, wherein the antibody comprises a first binding specificity which binds an epitope selected from the group consisting of:
the EGFR epitope bound by zalutumumab,
the EGFR epitope bound by cetuximab,
the EGFR epitope bound by panitumumab,
the EGFR epitope bound by nimotuzumab,
the EGFR epitope bound by matuzumab, and
the EGFR epitope bound by 528.

64. A bispecific antibody as defined in any one of embodiments 60 to 63 for use as a medicament.

65. A bispecific antibody as defined any one of embodiments 60 to 63 for use as a medicament for the treatment of cancer.

66. Use of a bispecific antibody as defined any one of embodiments 60 to 63 for the preparation of a medicament for the treatment of cancer.

67. A method for the treatment of cancer comprising administration of a bispecific antibody as defined in embodiment 60 or 61.

68. The bispecific antibody of embodiment 60 or 61, the use of embodiment 66 or the method of embodiment 67, wherein said tumor is selected from the group consisting of: breast cancer tumor, bladder cancer tumor, uterine/cervical cancer tumor, esophageal cancer tumor, pancreatic cancer tumor, colorectal cancer tumor, kidney cancer tumor, ovarian cancer tumor, prostate cancer tumor, head and neck cancer tumor, non-small cell lung cancer tumor, stomach cancer tumor, glioblastoma and other EGFR-expressing tumors.

The present invention is further illustrated by the following examples which should not be construed as further limiting.

EXAMPLES

Example 1

Generation and Source of Antibodies

Fully human IgG1,κ antibody 2F8 (HuMax-EGFR, zalutumumab) was generated as described previously (WO 02/100348). 2F8 F(ab)$_2$ fragments were produced by trypsin digestion of parental antibody 2F8. An IgG4 isotype variant of 2F8 was generated by genetic engineering, and produced in CHO cells as described previously (Danish patent application PA 2007 00491 (Genmab)).

Fully human IgG1,κ antibodies 003 (P- or LC1006-003), 005 (P- or LC1006-005), 008 (P- or LC1006-008), 011 (P- or LC1006-011) and 018 (P- or LC1006-018) were generated by immunizing HuMab mice (Medarex, Milpitas, Calif.) with alternating A431 cells and purified EGFR (Sigma-Aldrich, St. Louis, Mo. cat E-3641). Mouse spleens were fused with Sp2/0 mouse myeloma cells using Peg fusion or electrofusion. In some instances hybridomas derived directly from expansion of the fused cells were used in experiments. These hybridomas were named P1006-003, P1006-005, P1006-005, P1006-008, P1006-011 and P1006-018. The hybridomas were also cloned by limiting dilution, and subsequently named LC1006-003, -005, -008, -011 and -018. Culture supernatant was harvested and antibodies were purified at Genmab BV. using protein A affinity chromatography, followed by size exclusion chromatography on an HR200 column (Pharmacia, Peapack, N.J.) and formulation in PBS.

DNA constructs expressing antibody ch806 (described in WO02092771) were generated and expressed in HEK293 cells using standard procedures. Purification was performed using protein A affinity chromatography as described above.

DNA constructs expressing antibody MR1-1 (described in Beers et al. (2000) Clin. Cancer Res. 6:2835) were generated using standard procedures. Expression CHO cells and antibody purification was performed using protein A affinity chromatography as described above.

A human IgG1,κ antibody specific for keyhole limpet hemocyanin (Humab-KLH) developed using the same mouse strain, served as isotype control IgG in most experiments.

Apart from these, also the commercially available antibodies 225 (HB-8508, murine IgG1) and 528 (HB-8509, murine IgG2a; both from ATCC, Manassas, Va.), C225 (chimeric IgG1; cetuximab, Merck, Dietikon, Switzerland), E7.6.3 (fully human IgG2; panitumumab, Amgen, Thousand Oaks, Calif.) and matuzumab (h425, humanized IgG1, Merck, Darmstadt, Germany) were used.

For direct immunfluorescence studies, EGFR antibodies were fluorescein isothiocyanate (FITC)-conjugated using the EZ-label-kit (Pierce, Rockford, Ill.) according to the manufacturer's instructions.

Example 2

Sequencing of VH and VL Regions

Total RNA was prepared from $5\times10^6$ cells of hybridoma cell lines LC1006-003, -005, -008, -011 and -018 with the RNeasy kit (Qiagen, The Netherlands) according to the manufacturer's protocol. 5'-RACE-Complementary DNA (cDNA) of RNA was prepared from 100 ng total RNA, using the SMART RACE cDNA Amplification kit (Clontech), following the manufacturer's protocol. Oligonucleotide primers were synthesized and quantified by Isogen Bioscience (Maarssen, The Netherlands). Primers were dissolved in H$_2$O to 100 pmol/µl and stored at −20° C. A summary of all PCR and sequencing primers is tabulated in the table below. For PCR, PfuTurbo® Hotstart DNA polymerase (Stratagene, Amsterdam, The Netherlands) was used according to the manufacturer's instructions. Each reaction mix contained 200 µM mixed dNTPs (Roche Diagnostics, Almere, The Netherlands), 12 pmol of the reverse primer (RACEG1A1 for the VH and RACEKA1 for the VL), 7.2 pmol UPM-Mix (UPM-Mix: 2 µM ShortUPMH3 and 0.4 µM LongUPMH3), 0.6 µl of the 5'RACE cDNA template, and 1.5 unit of PfuTurbo® Hotstart DNA polymerase in PCR reaction buffer (supplied with polymerase) in a total volume of 30 µl. PCR reactions were carried out with a TGradient Thermocycler 96 (Whatman Biometra, Goettingen, Germany) using a 35-cycle program: denaturing at 95° C. for 2 min; 35 cycles of 95° C. for 30 sec, a 50° C. for 30 sec, and 72° C. for 1 min; final extension at 72° C. for 10 min. If appropriate, the PCR mixes were stored at 4° C. until further analysis or processing. The reaction products were separated by electrophoresis on a 1% TAE agarose gel and stained with ethidium bromide. Bands of the correct size were cut from the gels and the DNA was isolated from the agarose using the MiniElute Reaction Cleanup kit (Qiagen). Gel isolated PCR fragments were cloned into the pCR4Blunt-Topo vector (Invitrogen) using the Zero Blunt® TOPO® PCR Cloning Kit for Sequencing (Invitrogen) and protocol. 5 µl of the ligation mixture was transformed into OneShot DH5αT1R competent *E. coli* (Invitrogen) and plated on LB/Ampicillin plates. The V-regions of the antibodies were sequenced by AGOWA (Berlin, Germany) after picking more than 20 colonies of each specificity, isolating plasmid and sequencing with the M13 reverse primer. Analysis revealed a close similarity between the VHs of LC1006-003 and 008 and between LC1006-005 and 011 (see alignment in FIG. 17). All VLs were closely related. LC1006-003 and 008 had an identical VL and LC1006-005 and 011 both had an identical pair of two VLs, differing in a single amino acid. All sequences were in accordance with the results of the molecular weights of the antibodies as determined by ESI-MS.

Primers

| SEQ ID NO | Name | Length | Oligo Sequence |
| --- | --- | --- | --- |
| 19 | ShortUPMH3 | 31 | TGAAAGCTTCTAATACGACTCACTATAGGGC |
| 20 | RACEKA1 | 22 | TATCCACCTTCCACTGTACTTT |
| 21 | RACEG1A1 | 22 | GGGAGTAGAGTCCTGAGGACTG |
| 22 | M13reverse | 20 | GGATAACAATTTCACACAGG |
| 23 | LongUPMH3 | 54 | TGAAAGCTTCTAATACGACTCACTATAGGGCAAGCAGTGGTATCAACGCAGAGT |

Example 3

Functional Characterization of EGFR Antibodies 1006-003, -005, -008, -011 and -018

Binding to Purified EGFR:

ELISA plates (Greiner Bioscience, Frickenhausen, Germany, cat no: 655092) were coated with purified EGFR (Sigma-Aldrich, cat no. E3641) 0.4 µg/ml diluted in PBS 100 µl/well. The plates were incubated over night at 4° C.

After incubation the plates were emptied, and PBSC (PBS, 2% chicken serum) block solution was added 100 µl/well for 1 hour at room temperature (RT). The anti-EGFR clones were five fold serial diluted (40 µg/ml to 0.003 µg/ml) in PBSTC (PBS, 2% chicken serum, 0.05% tween-20) and incubated for 1 h at RT.

Subsequently, the plates were incubated with peroxidase-labeled goat anti-human IgG Fc-specific antibodies (Jackson Immunoresearch Laboratories, West Grove, Pa., cat no: 109-035-098). Next, the plates were incubated with ABTS (Roche, Mannheim, Germany, ABTS tablets cat no: 1112422, ABTS buffer cat no: 1112597). Absorbance was measured using a microplate reader (Bio-Tek Instruments, Winooski, Vt. cat no: EL808) at 405 nm. The binding was analysed using Graphpad Prism for fitting the data to a four parameter logistic curve.

| | EC50 (µg/ml) |
| --- | --- |
| 2F8 | 0.019 |
| P1006-003 | 0.117 |
| P1006-005 | 0.089 |
| P1006-008 | 2.459 |
| P1006-011 | 0.053 |
| P1006-018 | 0.081 |

The above table shows the concentrations of half-maximal binding (EC50) of clones P1006-003, -005, -008, -011, -018 and 2F8 to purified EGFR as observed in ELISA. The EC50 values were determined from a four-parameter logistic curve fit and are expressed in µg/ml. All antibodies bound to purified EGFR.

Binding to EGFR expressing cells of LC1006-003, -005, -008, -011 and -018 is shown in example 4.

Inhibition of EGFR Signalling:

Inhibition of EGFR signaling was tested by a ligand binding inhibition assay, an assay measuring inhibition of ligand-induced EGFR phosphorylation, and a cell proliferation assay.

A431 cells, an EGFR overexpressing epidermoid cancer cell line, were from the Deutsche Sammlung von Mikroorganismen und Zellkulturen (Braunschweig, Germany; cell line number ACC 91). Cells were cultured in RPMI 1640 medium (BioWhittaker, Verviers, Belgium, cat no: BE12-115F), supplemented with 10% heat-inactivated CCS (Hyclone Perbio. Logan, Utah, cat no: SH30087.03) and 50 IU/ml penicillin, 50 µg/ml streptomycin (BioWhittaker, cat no: DE17-603E). Cells were detached by using trypsin-EDTA (10× stock Gibco BRL, cat no: 35400-027) in PBS.

For comparison of EGFR antibodies' capacity to block ligand binding, $1.5 \times 10^5$ A431 cells were co-incubated with 2.5 µg/ml FITC-conjugated EGF (Invitrogen) and 200 µg/ml antibodies for 30 minutes. After washing, cells were analyzed by flow cytometry. Blockade of ligand binding was calculated by the formula: % inhibition of EGF-binding= (RFI without−RFI with antibody)/(RFI without antibody)× 100. All experimental steps were performed at 4° C. Data are presented as mean±SEM of three independent experiments. FIG. 1 shows that C225, E7.6.3 2F8, and 528 are strong inhibitors of EGF binding to A431 cells, that LC1006-003, LC1006-005, LC1006-008, and LC1006-011 are week inhibitors, and that LC1006-018 has no blocking activity.

To confirm that EGF binding inhibition resulted in inhibition of receptor auto-phosphorylation, we evaluated the potency of the different clones to inhibit ligand-induced EGFR phosphorylation in vitro. This was measured in a two-step assay using the epidermoid cell line, A431 (ATCC, American Type Culture Collection, Manassas, USA). The cells were cultured overnight in 96-wells plates in serum-free medium containing 0.5% human albumin (human albumin 20%, Sanquin, the Netherlands). Next, mAb were added in serial dilution. After 60 minutes incubation at 37° C., 50 ng/ml recombinant human EGF (Biosource) was added to induce activation of non-blocked EGFR. Following an additional 30 minutes incubation, cells were solubilized with lysis buffer (Cell Signaling Technology, Beverly, Mass.), and the lysates were transferred to ELISA plates coated with 1 µg/ml of mouse anti-EGFR antibodies (mAb EGFR1, BD Pharmingen, San Diego, Calif.). After 2 hours incubation at RT, the plates were washed and binding of phosphorylated EGFR was detected using a europium-labelled mouse mAb, specific for phosphorylated tyrosines (mAb Eu-N1 P-Tyr-100, PerkinElmer). Finally, DELFIA enhancement solution was added, and time-resolved fluorescence was measured by exciting at 315 nm and measuring emission at 615 nm on an EnVision plate reader (PerkinElmer). Sigmoidal dose-response curves were calculated using non-linear regression (GraphPad Prism 4).

Figure 2:
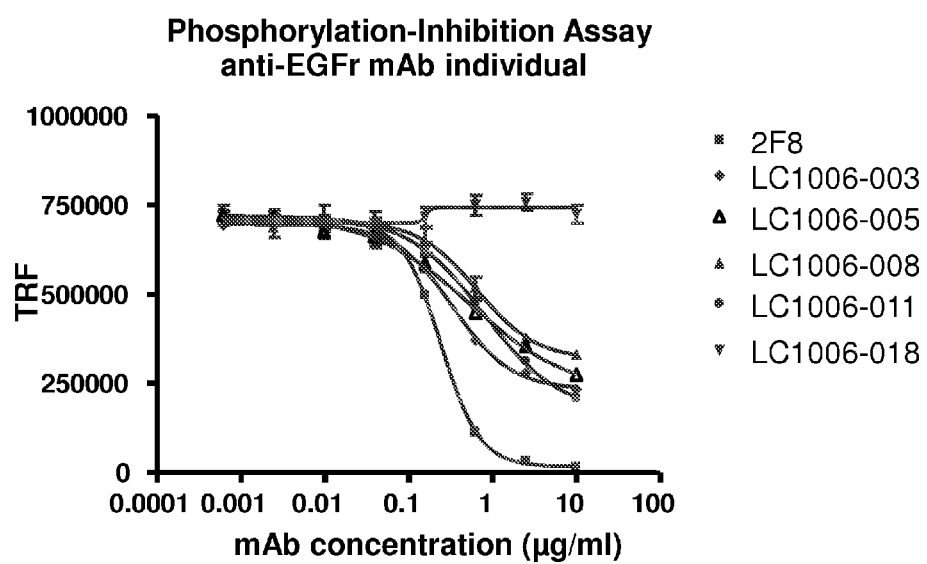
FIG. 2: Inhibition of ligand-induced EGFR phosphorylation by EGFR-antibodies. EGF-induced receptor phosphorylation of A431 cells was measured in the absence or presence of EGFR-antibodies.

FIG. 2 shows that LC1006-003, -005, -008, and -011 partially inhibited EGF-induced EGFR auto-phosphorylation, while clone 2F8 (HuMax-EGFR) gave complete inhibition and LC1006-018 did not.

The ability of EGFR antibodies to inhibit tumor cell proliferation was tested in an A431 proliferation assay. A431 cells were seeded at a density of 500 cells per well in a 96 wells culture plate (White, 96-well, TC, sterile, with lid, PerkinElmer, Boston, Mass., cat no: 6005680). A 3 fold serial dilution (100 µg/ml to 0.005 µg/ml) of each anti-EGFR clone in culture medium (RPMI 1640, 3% fetal clone II (Hyclone, cat no: SH30066.03), 1% penicillin/streptomycin) was added. Next, cells were incubated in a humidified incubator at 37° C./5% $CO_2$ for five days. Subsequently, 20 µl AlamarBlue (BioSource, Camarillo Calif. cat no: DAL1100) was added to each well and incubated at 37° C./5% $CO_2$ for 4 hours. Next, the fluorescence of the wells was measured at excitation wavelength of 528 nm and an emission wavelength of 590 nm using an ELISA plate reader, (BIO-Tek Synergy HT, Beun de Ronde, cat no: 7091000).

Figure 3:
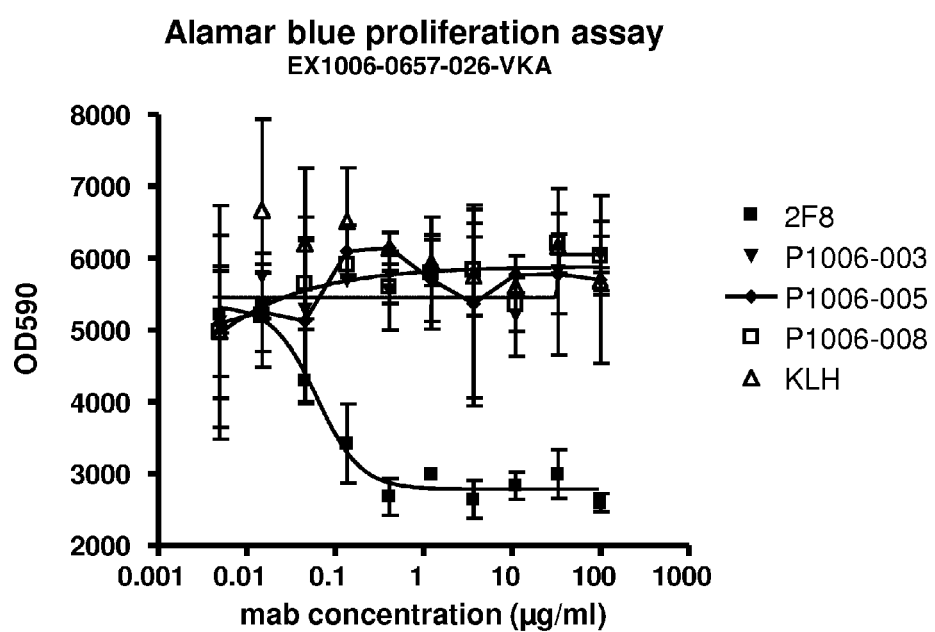
FIGS. 3 and 4: Inhibition of A431 cell proliferation by EGFR-antibodies.
Figure 4:
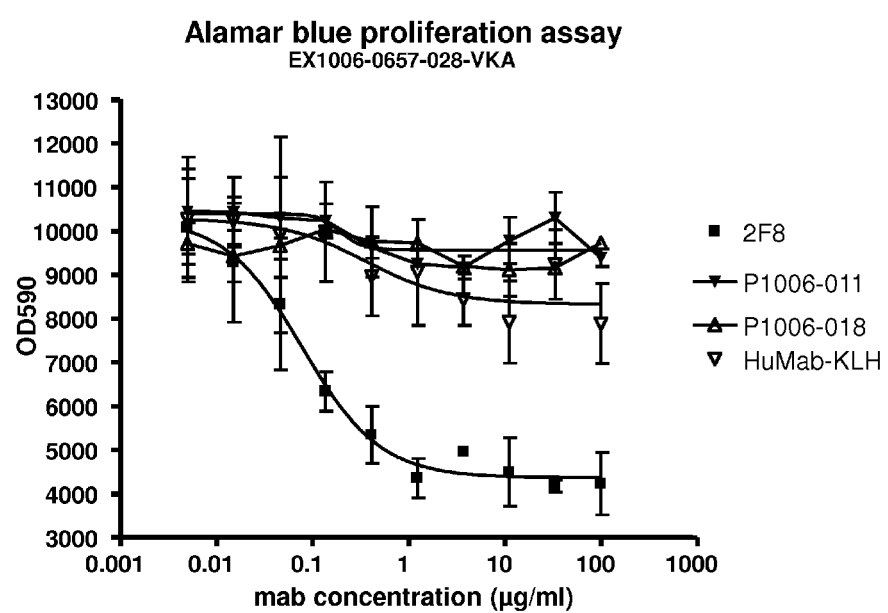

FIGS. 3 and 4 show that only clone 2F8 inhibited A431 proliferation.

Antibody-Dependent Cell-Mediated Cytotoxicity:

Peripheral blood mononuclear cells (PBMC) were isolated from standard blood donations (Sanquin Blood Bank, Utrecht, The Netherlands). Buffy coats were diluted by adding PBS and transferred to 50 ml tubes. 10 ml Lymfocyte Separation Medium (Bio Whittaker, cat no: US17-829E) was carefully placed under the diluted buffy coats. Tubes were centrifuged at 800×g for 20 min at RT. Thereafter, the PBMC were recovered from the plasma-medium interface and were washed several times with culture medium until the supernatant was clear. A431 target cells (2-5×10$^6$ cells) were labelled with 100 µCi $Na_2{}^{51}CrO_4$ (Amersham Biosciences, Uppsala, Sweden, cat no: CSJ11) under shaking conditions at 37° C. for 1 hour. After incubation cells were washed thrice with PBS and resuspended in culture medium (1×10$^5$ cells/ml). Labelled cells were pipetted in 96 well plates (5×10$^3$, in 50 µl/well) and preincubated with a 5 fold serial dilution (20 µg/ml to 0.0003 µg/ml) of anti-EGFR clones for 30 min at RT. Culture medium was added instead of mAb to determine the spontaneous $^{51}Cr$ release, Triton X-100 (1% final concentration, Riedel de Haen, cat no: 56029) was added to determine the maximal $^{51}Cr$ release. Subsequently, PBMC's were dispensed into the plate (5×10$^5$/well) and the cells were incubated at 37° C. over night. The next day, supernatants were collected for measurement of $^{51}Cr$ release by determination of the cpm in a gamma counter. Specific lysis is calculated with formula below:

% specific lysis=(experimental release (cpm)−spontaneous release (cpm))/(maximal release (cpm)−spontaneous release (cpm))×100

Figure 5:
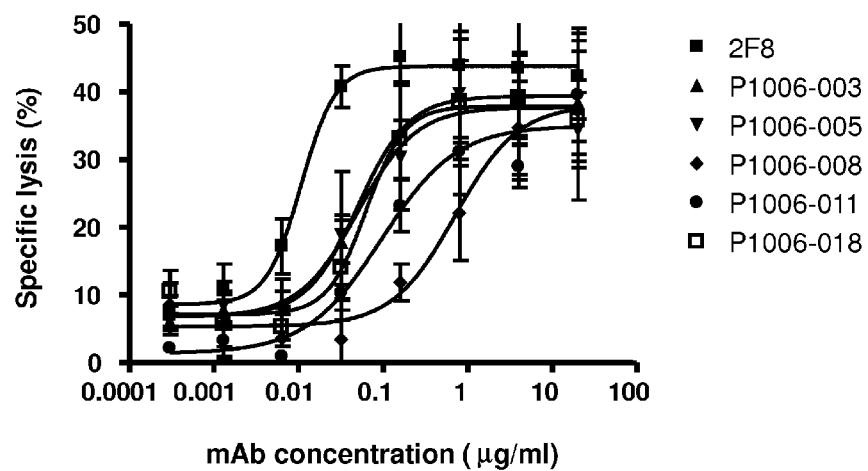
FIG. 5: Stimulation of PBMC-induced ADCC of A431 target cells by EGFR-antibodies.

FIG. 5 shows that P1006-003, -005, -008, -011 and -018 stimulated PBMC-induced ADCC of A431 target cells. The ability of LC1006-003, -005, -008, -011 and -018 to induce complement-dependent cytotoxicity is described below.

Example 4

Binding of EGFR Antibodies to EGFR-Expressing Cells

The human epidermoid carcinoma cell line A431 (DSMZ, Braunschweig, Germany) and human glioblastoma cell line A1207 (originally established by Dr. Aaronson, National Cancer Institute, National Institutes of Health, Bethesda, Md.) were kept in RPMI 1640 or DMEM, respectively. Both media were supplemented with 10% heat-inactivated fetal calf serum (FCS), 100 U/ml penicillin, 100 U/ml streptomycin, and 4 mM L-glutamine (all from Invitrogen, Carlsbad, Calif.). Viability of cells was tested by trypan blue exclusion.

Cell lines were characterised for quantitative surface expression of EGFR and complement regulatory proteins CD46, CD55 and CD59 by indirect immunofluorescence. 1×10$^5$ target cells were incubated with murine monoclonal antibodies 225 (EGFR), J4-48 (CD46, Immunotech, Marseille, France), IA10 (CD55) or p282 (CD59, both from BD Pharmingen, Franklin Lakes, N.J.), respectively, at saturating concentrations for 30 minutes at 4° C. After washing, cells were stained with FITC-conjugated polyclonal goat anti-mouse Ig (DAKO, Glostrup, Denmark) for 30 minutes at 4° C., washed and analysed by flow cytometry. For calculation of antigens' surface expression, the Qifikit (DAKO) was used according to the manufacturer's instructions.

The table below shows the characterization of the cell lines:

| Cell line | Antigen | Calculated molecules/cell |
|---|---|---|
| A431 | EGFR | 1,782,006 ± 196,146 |
| | CD46 | 220,087 ± 17,811 |
| | CD55 | 175,691 ± 25,906 |
| | CD59 | 708,530 ± 81,880 |
| A1207 | EGFR | 1,673,737 ± 87,269 |
| | CD46 | 179,972 ± 15,654 |
| | CD55 | 66,077 ± 5,063 |
| | CD59 | 355,082 ± 46,611 |

Figure 6:
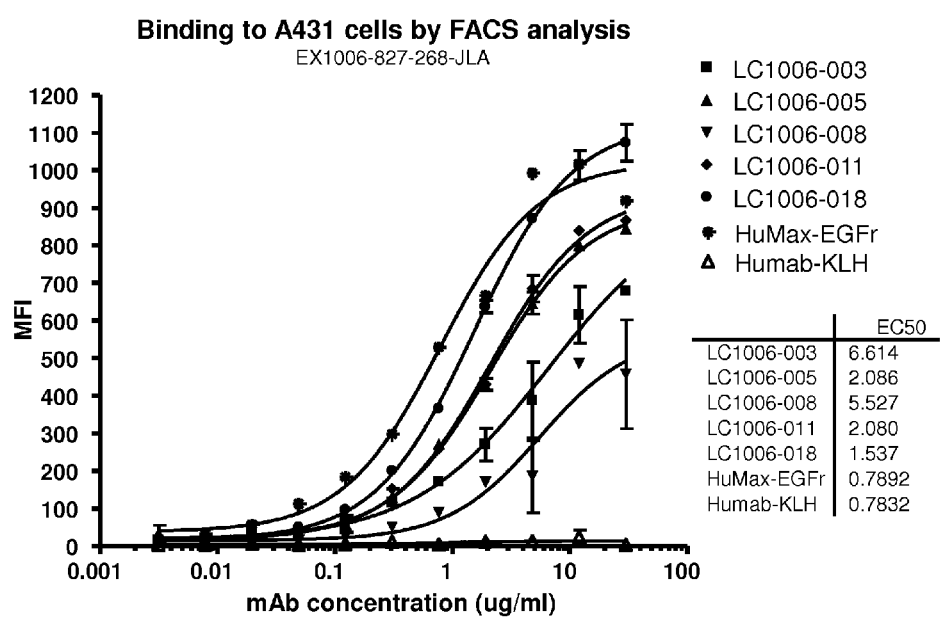
FIG. 6: FACS analyses of EGFR-antibody binding to A431 cells. Data are presented as mean±SEM of two independent observations. The concentrations of half-maximal binding (EC50) are determined from a four-parameter logistic curve fit and expressed in µg/ml.
Figure 7A:
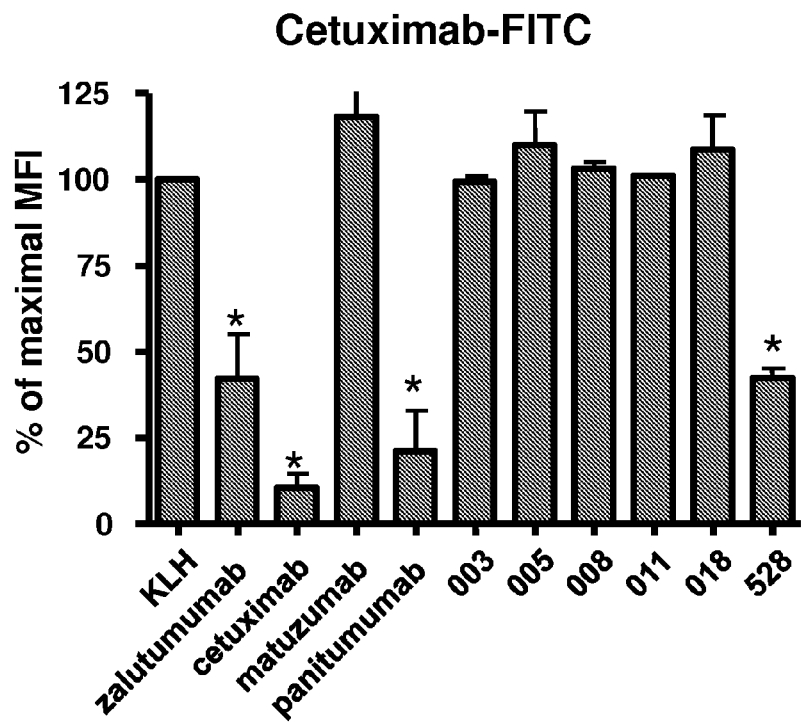
FIGS. 7A-7I: Epitope analyses by competitive immunofluorescence. Non-saturating concentrations of indicated FITC-conjugated EGFR antibodies (FIG. 7A: cetuximab-FITC.
Figure 7B:
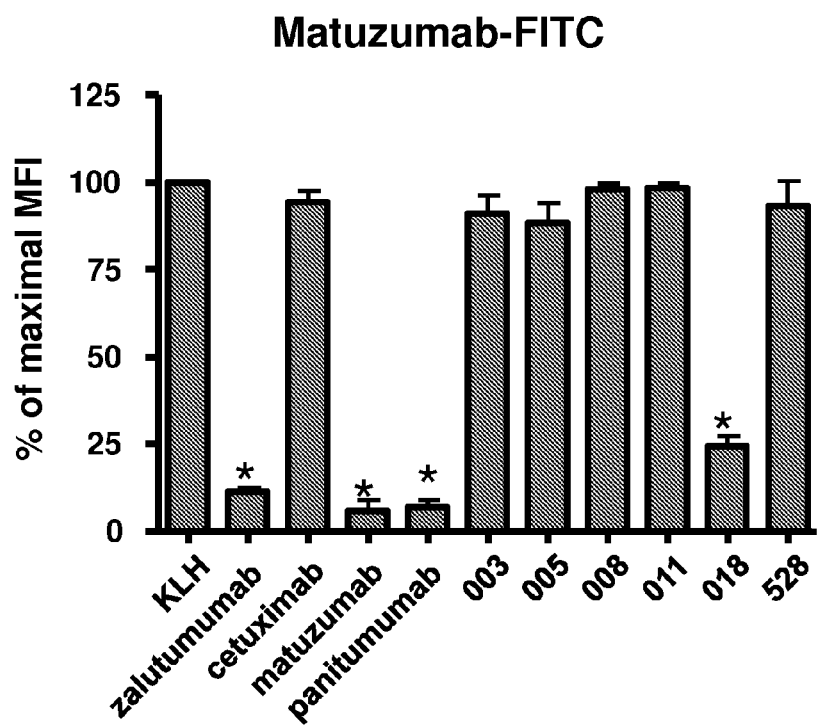
Figure 7C:
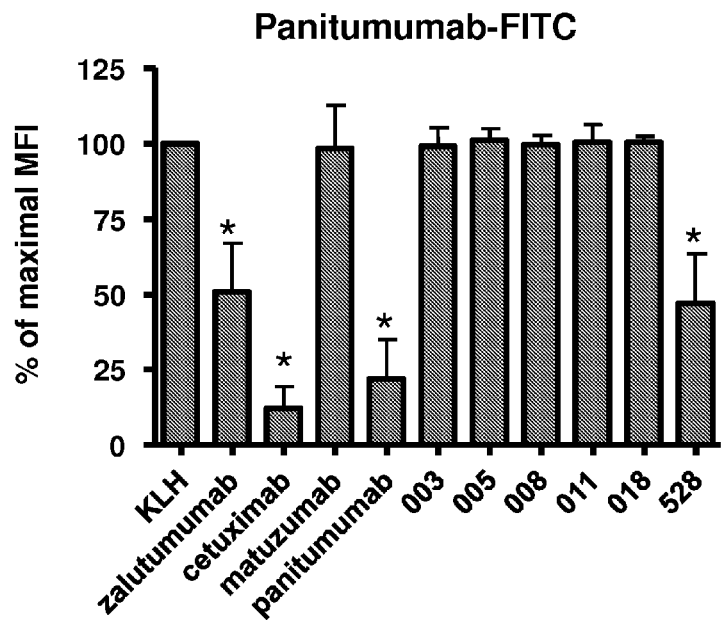
Figure 7D:
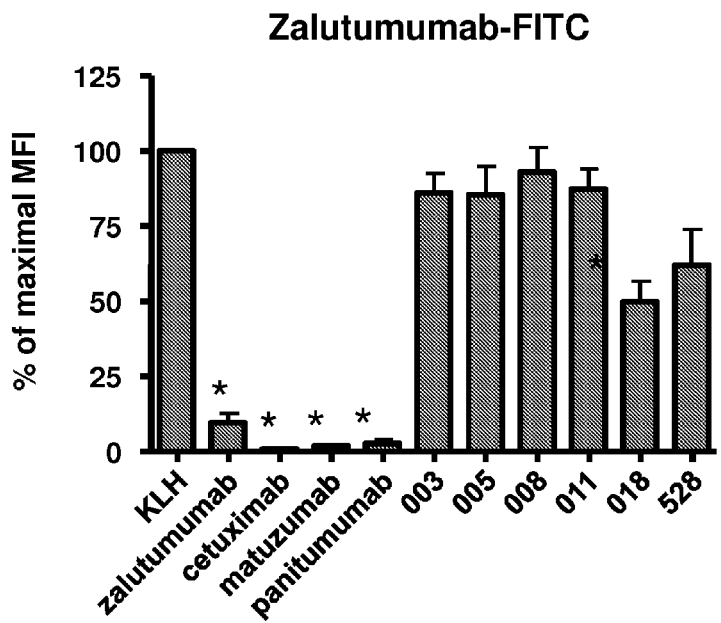
Figure 7E:
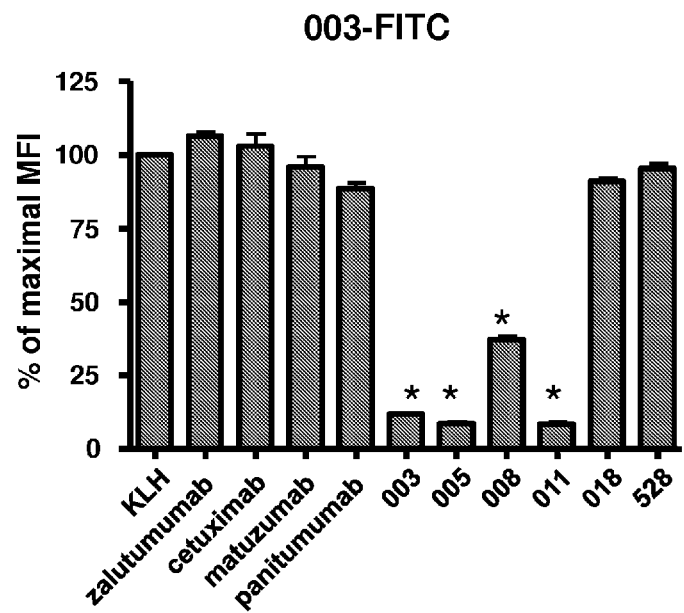
Figure 7F:
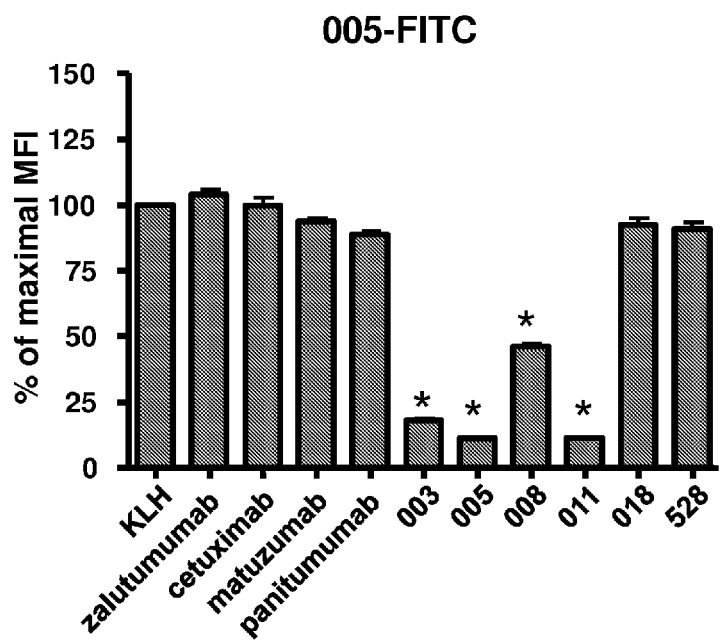
Figure 7G:
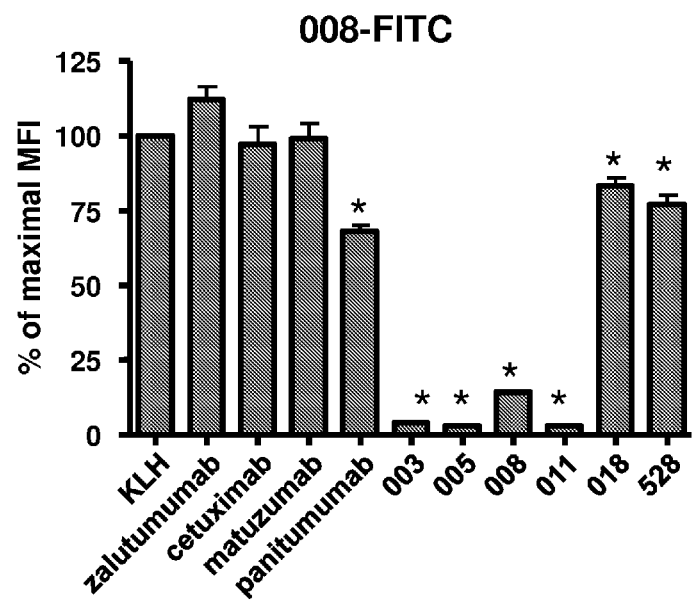
Figure 7H:
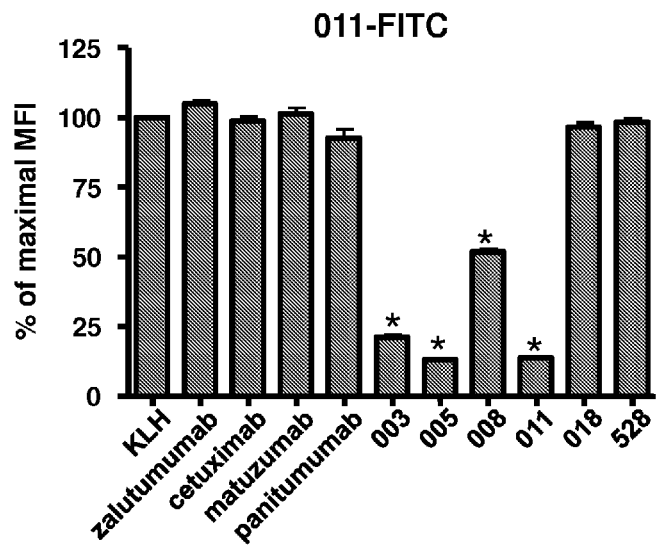
Figure 7I:
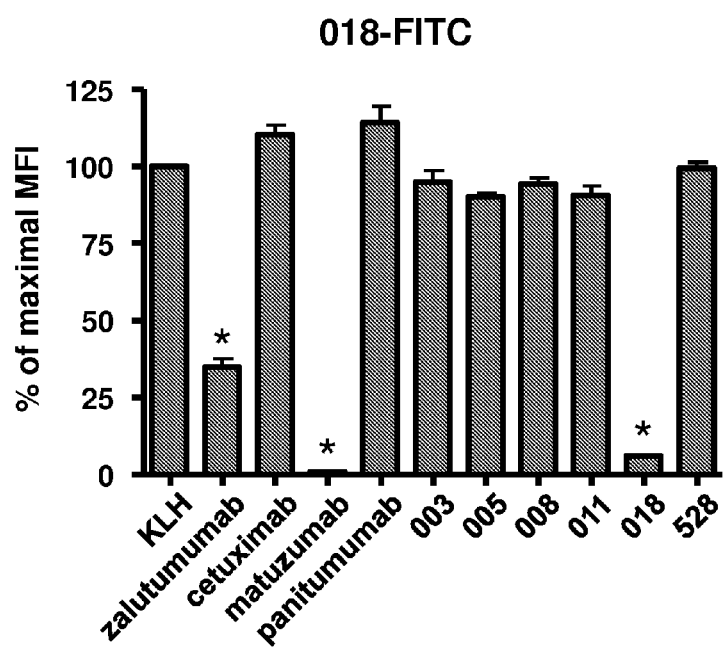

Binding of the panel of EGFR-antibodies to A431 cells, as measured by FACS analysis is shown in FIG. 6.

Example 5

Cross-Blocking of EGFR Antibodies

The EGFR binding epitopes of different EGFR antibodies were analyzed by competitive immunofluorescence binding assays. 2×10$^5$ EGFR expressing target cells were incubated for 30 minutes at 4° C. with FITC-conjugated EGFR antibodies at non-saturating concentrations in combination with 200-fold excess of different unconjugated antibodies. After washing, samples were analysed by flow cytometry. Level of competition was calculated with the following formula: % competition=(experimental MFI−background MFI)/(maximal MFI−background MFI)×100, with maximal MFI defined by the combination of FITC-conjugated EGFR antibody with isotype control antibody KLH.

Figure 8:
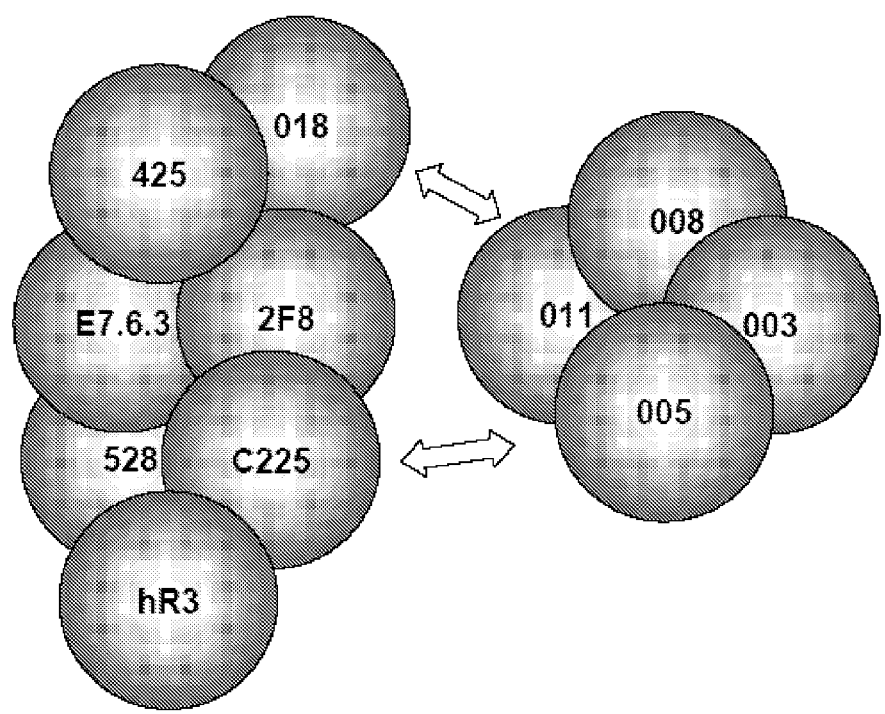
FIG. 8: Cartoon of EGFR epitopes recognized by different antibodies. Significant inhibition in competitive immunofluorescence experiments is indicated by overlapping circles, while non-overlapping circles indicate that the respective antibodies did not significantly cross-block each other.
Figure 9:
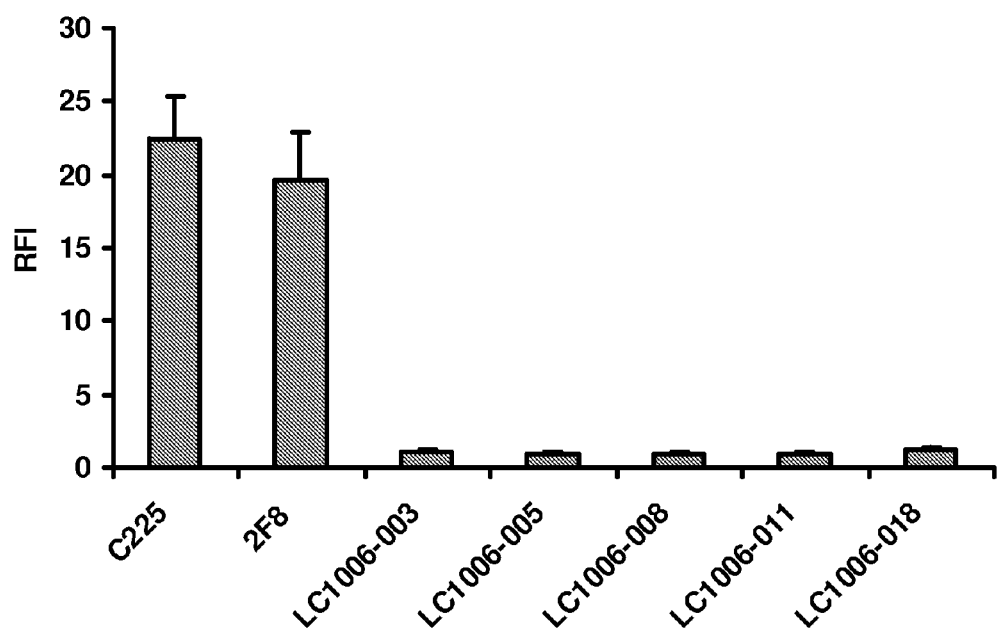
FIG. 9: Binding of EGFR-antibodies to Ba/F3 cells expressing EGFR-vIII deletion mutant, which lacks AA 6-273, the major portion of domains I and II.

FIG. 7 shows the results of competitive immunofluorescence studies. FIG. 8 exemplifies the cross-blocking of the different antibodies graphically. To further investigate epitope differences, the antibodies were also compared in their ability to bind to Ba/F3 cells transfected with EGFR-vIII. EGFR-vIII is characterized by deletion of exons 2 to 7, involving nucleotides 275 to 1075. Thus, EGFR-vIII lacks a major portion of the Cys-rich ligand-binding domain, near the NH2 terminus of the extracellular portion of the molecule. In this experiment, $2 \times 10^5$ EGFR-vIII transfected cells were incubated with EGFR antibodies at saturating concentrations for 30 minutes, washed and stained with FITC-conjugated F(ab')$_2$-fragments of polyclonal anti-human IgG antibodies (DAKO) for 30 minutes. After washing again, cells were analyzed by flow cytometry. All experimental steps were performed at 4° C. Data are presented as mean±SEM of four independent experiments. FIG. 9 shows that C225 and 2F8 bound to EGFR-vIII, whereas LC1006-003, 005, 008, 011 and 018 did not.

Example 6

Figure 10A:
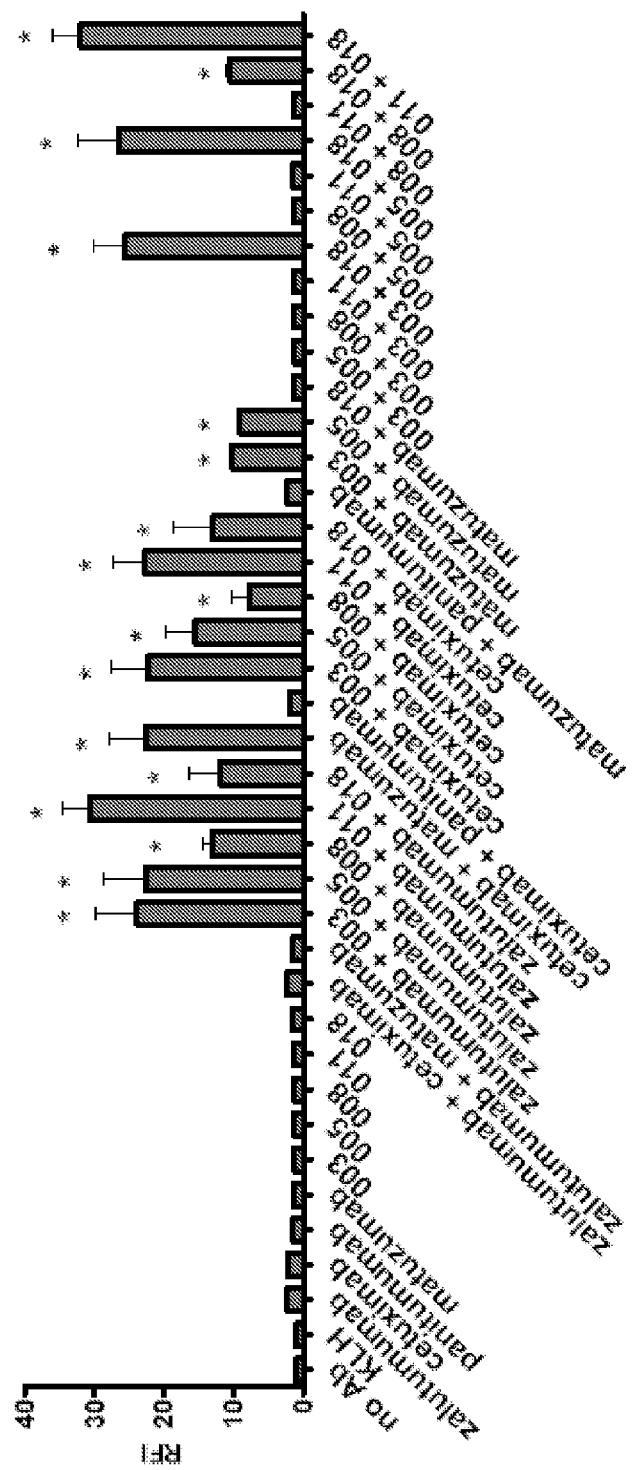
FIGS. 10A, 10B, and 11: C1q deposition by EGFR antibody combinations. C1q deposition on A431 cells was analyzed in the presence of individual EGFR antibodies, or in the presence of antibody combinations (final antibody concentration 10 µg/mL).
Figure 10B:
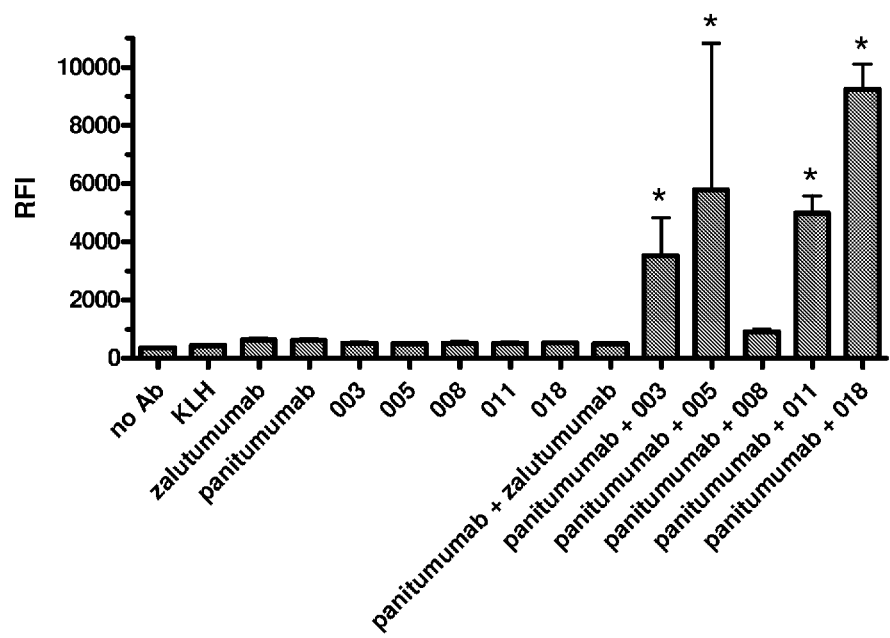

Complement Deposition $1 \times 10^5$ target cells were incubated for 15 minutes at room temperature either with individual EGFR antibodies, or with antibody combinations at additive antibody concentrations of 10 μg/ml/well, followed by addition of 1% (vol/vol) NHS and incubation at 37° C. for 10 minutes. After washing, samples were stained with polyclonal FITC-conjugated C1q or C4c antibodies (both from DAKO) for 30 minutes at 4° C., and analyzed by flow cytometry (FIG. 10a: Coulter EPICS XL-MCL, Beckman Coulter, Fullerton, Calif., FIG. 10b: FACSCanto II, Becton Dickinson, Aalst, Belgium).

Figure 11:
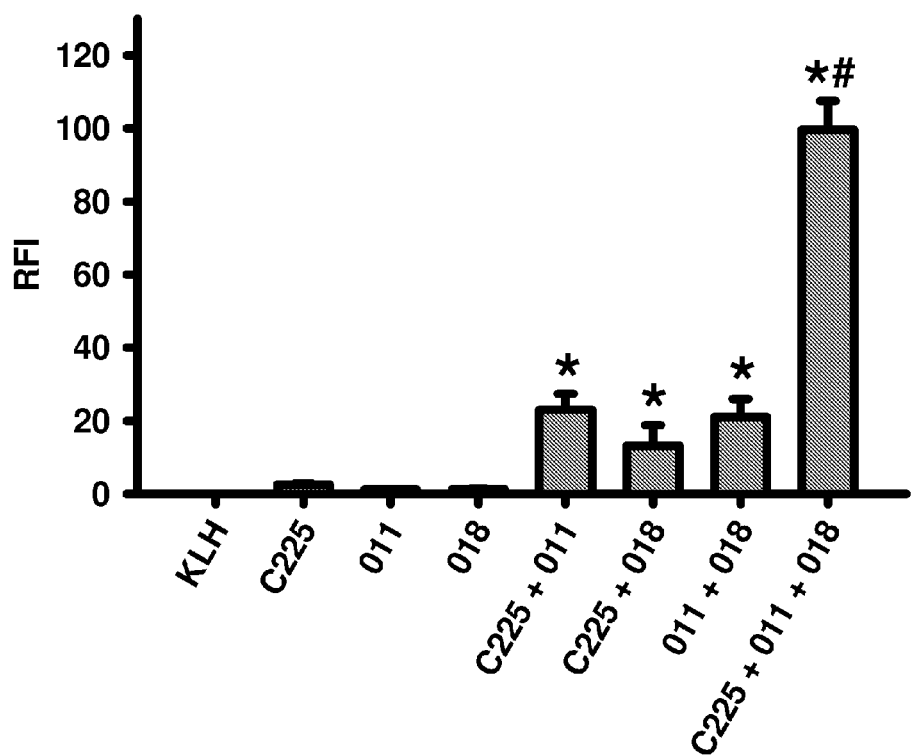

FIG. 10 shows that while individual EGFR antibodies did not trigger C1q deposition, all examined non cross-blocking combinations led to C1q deposition (except for certain combinations that include 008, which is presumably due to the low affinity of 008 (see FIG. 6)). As shown in FIG. 11, the combination of three non-blocking antibodies is superior to individual dual combinations in C1q deposition.

Example 7

Complement Dependent Cytotoxicity (CDC)

Target cells were labeled with 200 μCi (7.4 MBq) $^{51}$Cr for 2 hours. After washing three times with RPMI 1640 medium, cells were adjusted to $10^5$/ml. 50 μl freshly drawn human serum, sensitizing antibodies and RPMI 1640 (10% FCS) were added to round-bottomed microtiter plates (Nunc, Rochester, N.Y.). Assays were started by adding target cells (50 μl), resulting in a final volume of 200 μl/well and a final concentration of 25% serum (unless otherwise indicated). After 3 hours at 37° C., assays were centrifuged, and $^{51}$Cr release from the supernatants was measured in triplicates as counts per minute (cpm). Percentage of cytotoxicity was calculated with the following formula: % specific lysis=(experimental cpm−asal cpm)/(maximal cpm−basal cpm)×100, with maximal $^{51}$Cr release determined by adding perchloric acid (3% final concentration) to target cells and basal release measured in the absence of sensitizing antibodies and serum. Antibody-independent cytotoxicity (serum without target antibodies) was not observed.

Figure 12A:
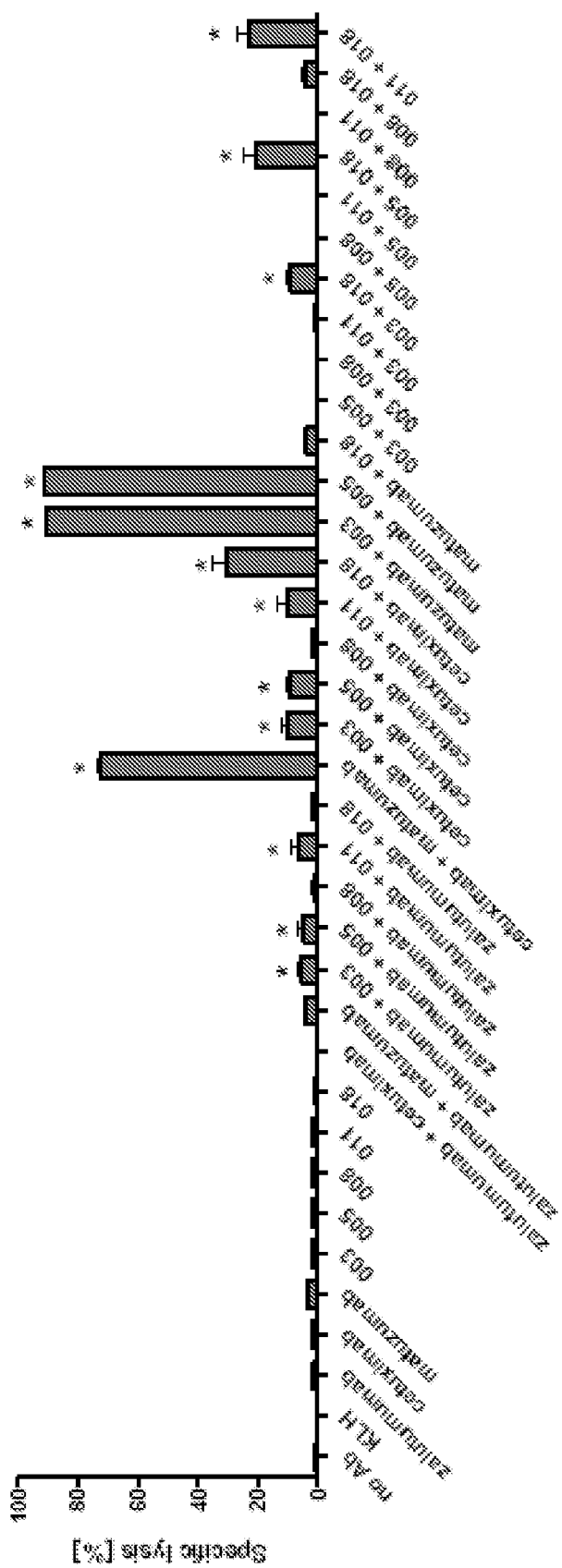
FIGS. 12A and 12B: Complement dependent killing by individual EGFR antibodies and by antibody combinations. Individual EGFR antibodies, cross-blocking and non cross-blocking combinations were analyzed for their capacity to trigger CDC of A431 cells (FIG. 12A) and A1207 cells (FIG. 12B). While none of the individual EGFR antibodies and none of the cross-blocking combinations triggered CDC, most of the non cross-blocking combinations led to significant CDC (p<0.05, indicated by *). Data are presented as mean±SEM of "% specific lysis" from at least three independent experiments.
Figure 12B:
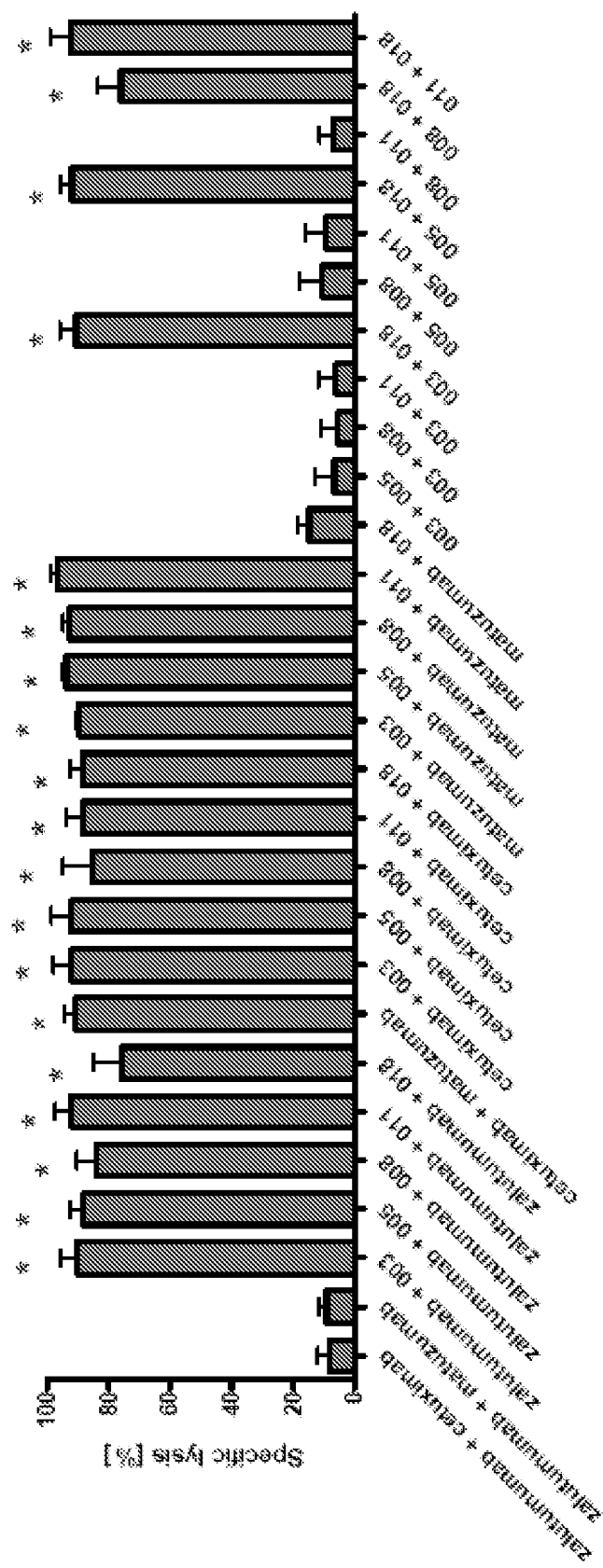

FIG. 12 shows that while none of the individual EGFR antibodies and none of the cross-blocking combinations triggered CDC, most of the non cross-blocking combinations led to significant CDC on A431 cells (12a) and all non cross-blocking combinations led to significant CDC on A1207 cells (12b).

Figure 13A:
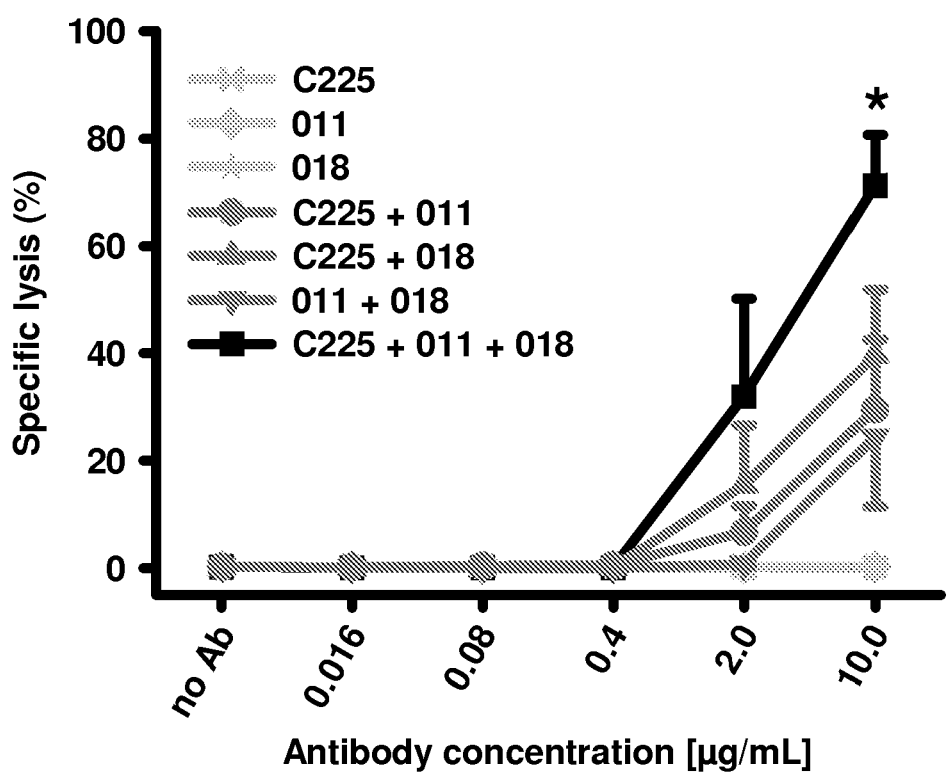
FIGS. 13A and 13B: CDC in correlation to antibody concentrations. CDC of A431 (FIG. 13A) and A1207 (FIG. 13B) cells by individual EGFR antibodies and by antibody combinations was analyzed at various antibody concentrations. Indicated antibody concentrations refer to each individual antibody. Results are presented as mean±SEM of "% specific lysis" of three independent experiments, significant CDC (p<0.05) is indicated by *.
Figure 13B:
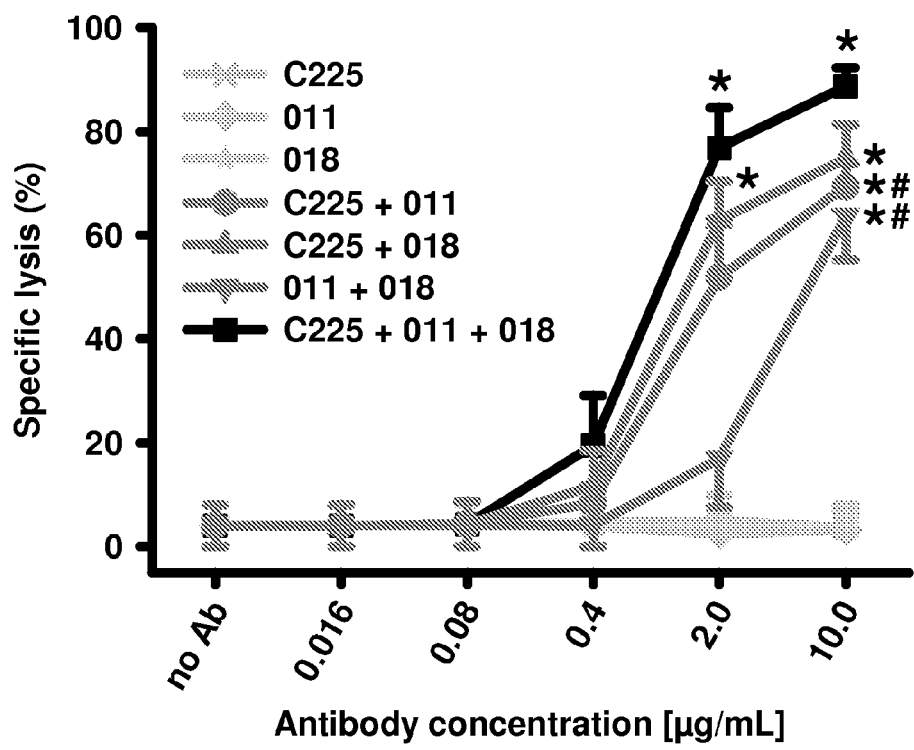

FIG. 13 shows CDC of A431 (13a) and A1207 (13b) cells in correlation to EGFR antibody concentration.

Example 8

Contribution of the Alternative and Classical Pathway of Complement Activation in EGFR Antibody Mediated CDC To determine the contribution of different complement activation pathways in EGFR antibody mediated CDC, final concentrations of 5 mM $MgCl_2$ and 10 mM ethylene-glycol-bis(β-aminoethylether)-tetraacetic-acid (Mg-EGTA) were added to selectively inhibit the classical pathway, or 10 mM ethylenediamine tetraacetic acid (EDTA; both from Roth, Karlsruhe, Germany) for complete blockade of complement activation, respectively. Furthermore, for some experiments serum was heated to 50° C. for 15 minutes to selectively inactivate the alternative pathway, or to 56° C. for 30 minutes for complete heat-inactivation of the complement system. A431 cells were used as target cells, antibodies at a concentration of 2 μg/ml.

Figure 14:
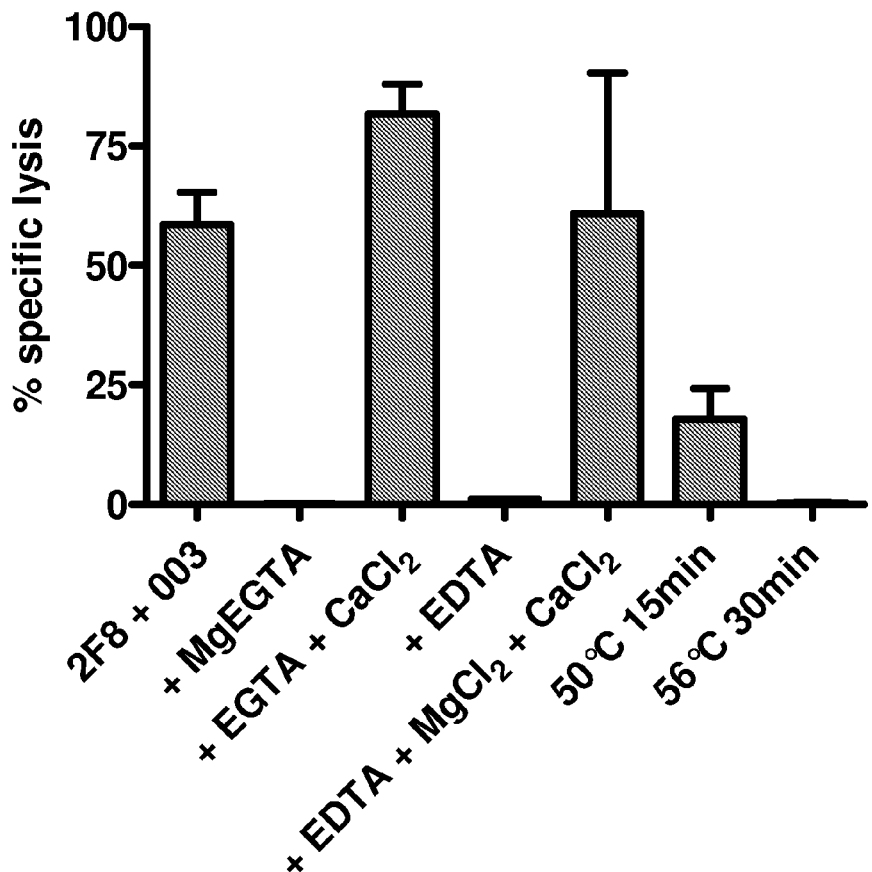
FIG. 14: CDC by EGFR antibody combinations is mediated by the classical complement pathway. To identify the respective contribution of the alternative and the classical complement pathways in CDC by EGFR antibody combinations, CDC assays were performed in the presence of Mg-EGTA (inactivation of the classical pathway) or EDTA (inactivation of both pathways), and after inactivation of the alternative (50° C. for 15 min) or both (56° C. for 30 min) pathways. Data are presented as mean±SEM of two independent experiments.

FIG. 14 shows that CDC by EGFR antibody combinations is mediated by the classical complement pathway.

Example 9

Requirement of IgG1 Fc Regions for EGFR Antibody Mediated CDC

Figure 15:
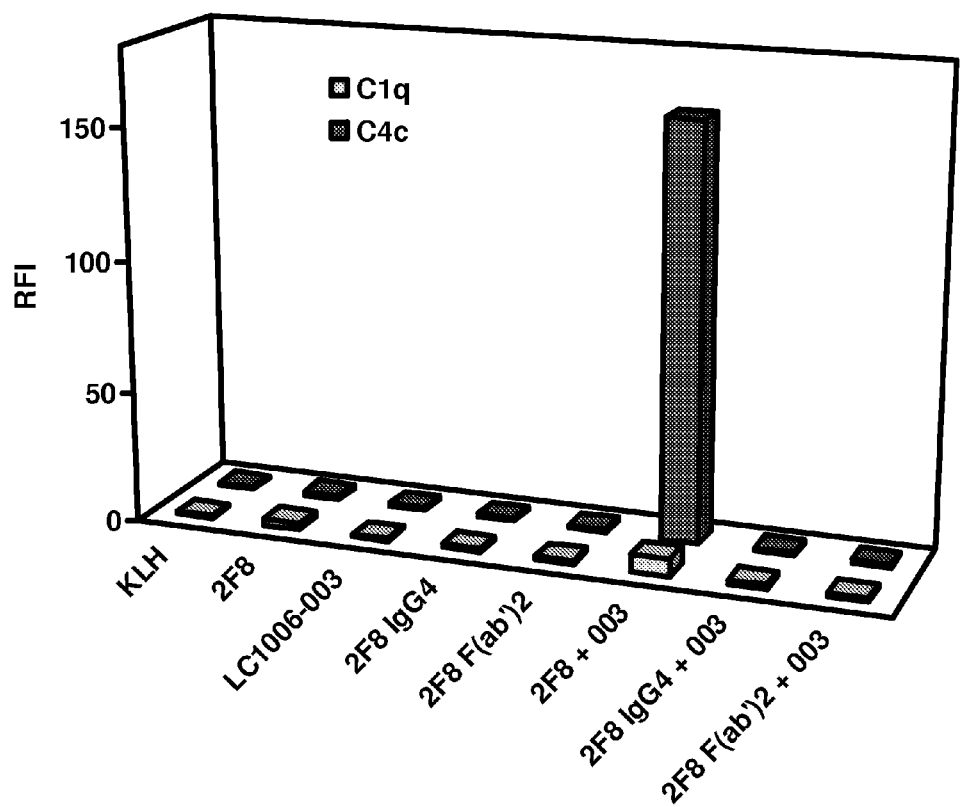
FIGS. 15 and 16: C1q and C4c binding (FIG. 15, n=1) and CDC (FIG. 16, n=2) by EGFR antibody combinations. Combinations of EGFR antibody LC1006-003 with 2F8-IgG1, 2F8-IgG4 or 2F8-F(ab)$_2$ were tested.
Figure 16:
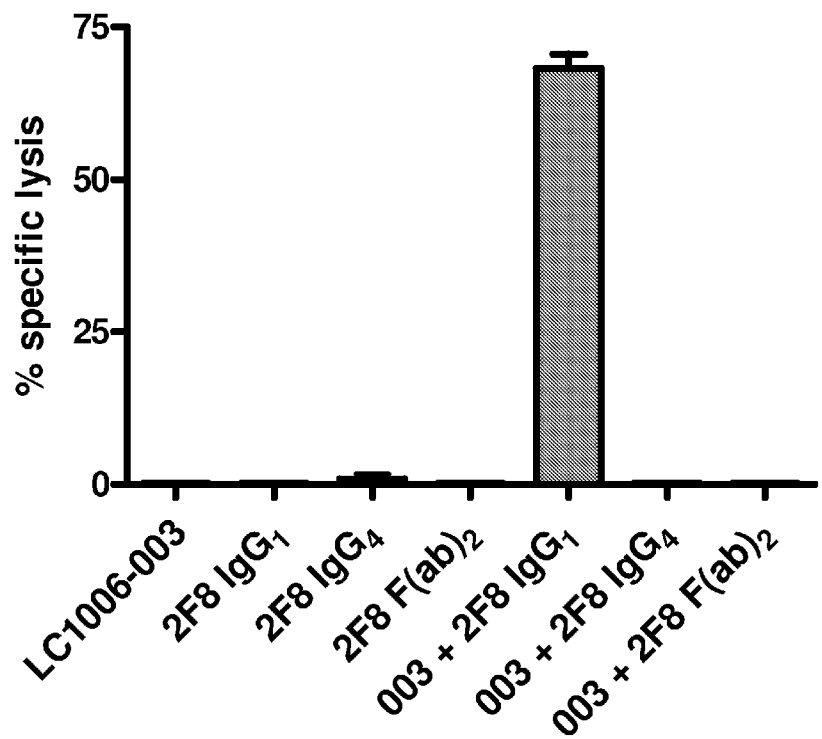

Combinations of EGFR antibody LC1006-003 with 2F8-IgG1, 2F8-IgG4 or 2F8-F(ab)$_2$ were tested in their ability to bind C1q and C4c, and to induce CDC. A431 cell line was used as target. It was found that relevant complement-deposition and -lysis was only observed in the presence of two human IgG1 Fc fragments (FIGS. 15 and 16).

Example 10

Specific Lysis of EGFR-vIII Expressing A431 Cells

The human epidermoid carcinoma cell lines A431 and Ba/F3 cells (DSMZ, The German Resource Centre for Biological Material, Braunschweig, Germany) were cultured in RPMI 1640-Glutamax-I medium (Invitrogen Life Technologies) containing 10% heat-inactivated fetal calf serum (FCS), 100 U/ml penicillin, and 100 U/ml streptomycin (R10+). For the Ba/F3 cell line, murine (m) IL-3 was either added as recombinant mIL-3 (R&D Systems) at 10 ng/ml or as supernatant from WEHI-3B cells (DSMZ; concentration 10% v/v). Medium for transfected cells additionally contained 1 mg/ml geneticin (Invitrogen Life Technologies). Viability of cells was tested by trypan blue exclusion.

The extracellular EGFR-vIII mutation was generated by splicing by overlapping extension PCR (SOE-PCR) of the plasmid vector pUSE-EGFR (Upstate Biotechnology) harboring wt EGFR. EGFR-vIII coding DNA was amplified by PCR using pUse-EGFR as a template with the following primers: exon 1; 5'ACCCACTGCTTACTGGCTTATCG-3' (SEQ ID NO: 24) and 5'-CCGTGATCTGTCACCA-CATAATTACCTTTCTTTTCCTCCAGAGCCCGACTC-3' (SEQ ID NO: 25), Exon 8; 5'-GAGTCGGGCTCTGGAG-GAAAAGAAAGGTAATT ATGTGGTGACAGAT-CACGG-3'(SEQ ID NO: 26) and 5'-CCTGTGCAGG TGATGTTCATGG-3' (SEQ ID NO: 27). Introduction of the respective mutation and the correctness of the EGFRvIII coding region was confirmed by complete sequencing.

Ba/F3 cells were stably transfected by nucleofection of 2 μg of plasmid DNA and $2 \times 10^6$ cells using the Amaxa transfection system according to the manufacturer's instructions. Forty-eight hours after transfection, cells were put under selection by adding 1 mg/ml geneticin.

A431 cells ($3.5 \times 10^5$) were transfected with Lipofectamine2000 (Invitrogen Life Technologies) according to the manufacturer's instructions. Transfected cells were selected with 0.8 mg/ml geneticin.

Twenty million transfected Ba/F3 cells were incubated with 4 ml of EGFR mAb m225 (mIgG1) at 20 μg/ml in PBS containing 0.5% BSA and 25% rabbit serum (to block nonspecific binding of the primary Ab). After 15 min on ice, cells were washed twice with PBS containing 0.5% BSA. The cell pellet was resuspended in 200 µl of PBS containing 0.5% BSA and 50% rabbit serum. Fifty microliters of anti-mouse IgG1 magnetic beads (Miltenyi Biotec) was added, and cells were incubated for another 10 min on ice. Cells were washed twice and separated on LD depletion columns according to the manufacturer's instructions (Miltenyi Biotec).

Transfected A431 cells ($5\times10^6$) were labeled with MR1-1 IgG1 antibody and rabbit anti human IgG fluorescein conjugated secondary antibody. Labeled cells were sorted with a ARIA flow cytometer (Becton Dickinson) into 96 well plates and cloned by limited dilution. Expression of EGFRvIII of individual clones was detected by flow cytometry. High expression clones were used for further analysis.

Target cells were labeled with 200 µCi (7.4 MBq) $^{51}$Cr for 2 hours. After washing three times with RPMI 1640 medium, cells were adjusted to $10^5$/ml. 50 µl freshly drawn human serum, sensitizing antibodies and RPMI 1640 (10% FCS) were added to round-bottomed microtiter plates (Nunc, Rochester, N.Y.). Assays were started by adding target cells (50 µl), resulting in a final volume of 200 µl/well and a final concentration of 25% serum (unless otherwise indicated). After 3 hours at 37° C., assays were centrifuged, and $^{51}$Cr release from the supernatants was measured in triplicates as counts per minute (cpm). Percentage of cytotoxicity was calculated with the following formula: % specific lysis=(experimental cpm−basal cpm)/(maximal cpm−basal cpm)×100, with maximal $^{51}$Cr release determined by adding perchloric acid (3% final concentration) to target cells and basal release measured in the absence of sensitizing antibodies and serum.

Figure 18:
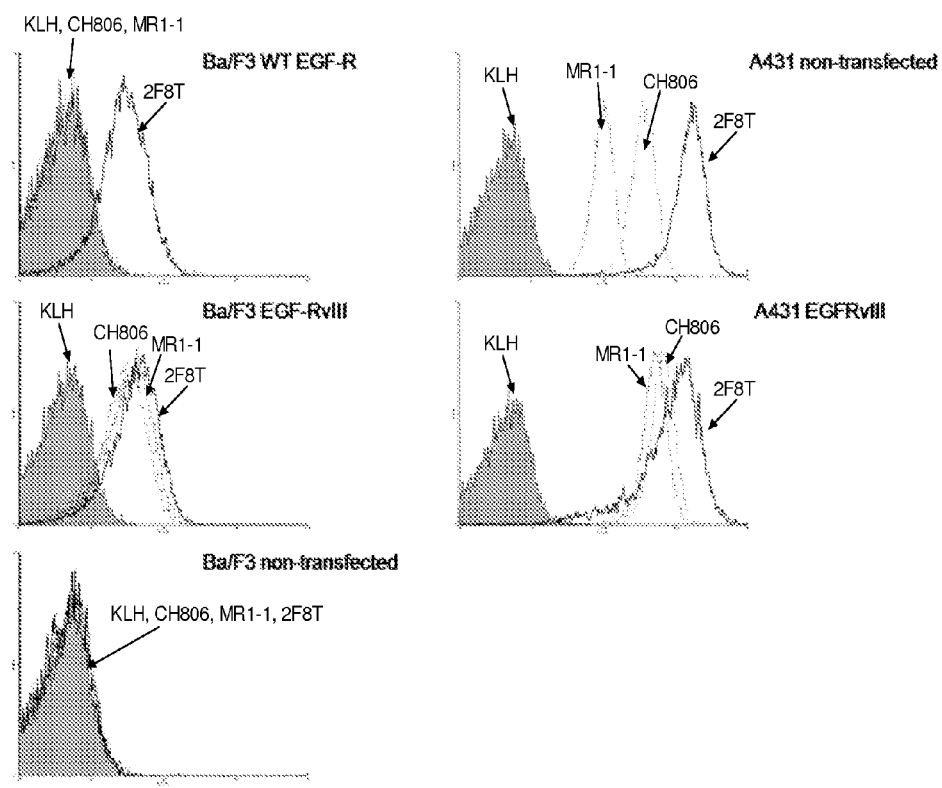
FIG. 18: Comparison of ch806, MR1-1 and zalutumumab binding properties to untransfected or EGFR-vIII transfected A431 cells, and wild type or EGFR-vIII transfected Ba/F3 cells.

FIG. 18 shows that antibodies ch806, MR1-1 and zalutumumab all bound to wild-type EGFR on A431 cells as well as to EGFR-vIII expressed on Ba/F3 and A431 cells.

Figure 19A:
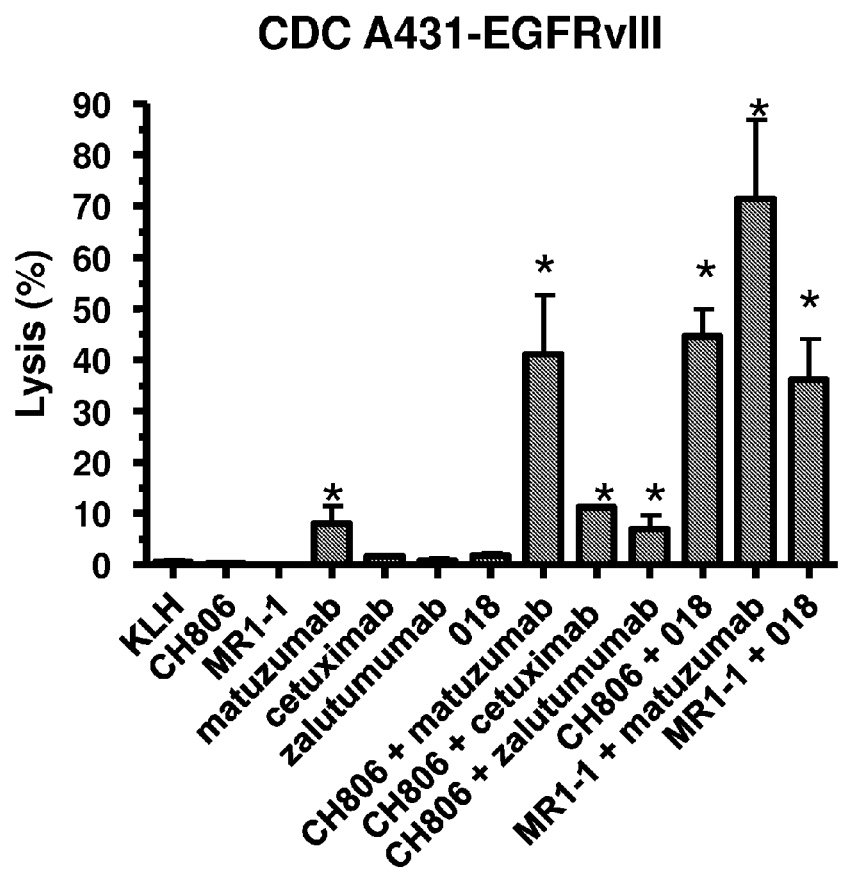
FIGS. 19A and 19B: CDC of untransfected (FIG. 19B) and EGFR-vIII transfected (FIG. 19A) A431 cells by combinations of EGFR antibodies with ch806 or MR1-1. Cells were incubated with individual antibodies, or with antibody combinations at additive antibody concentrations of 10 μg/ml/well.
Figure 19B:
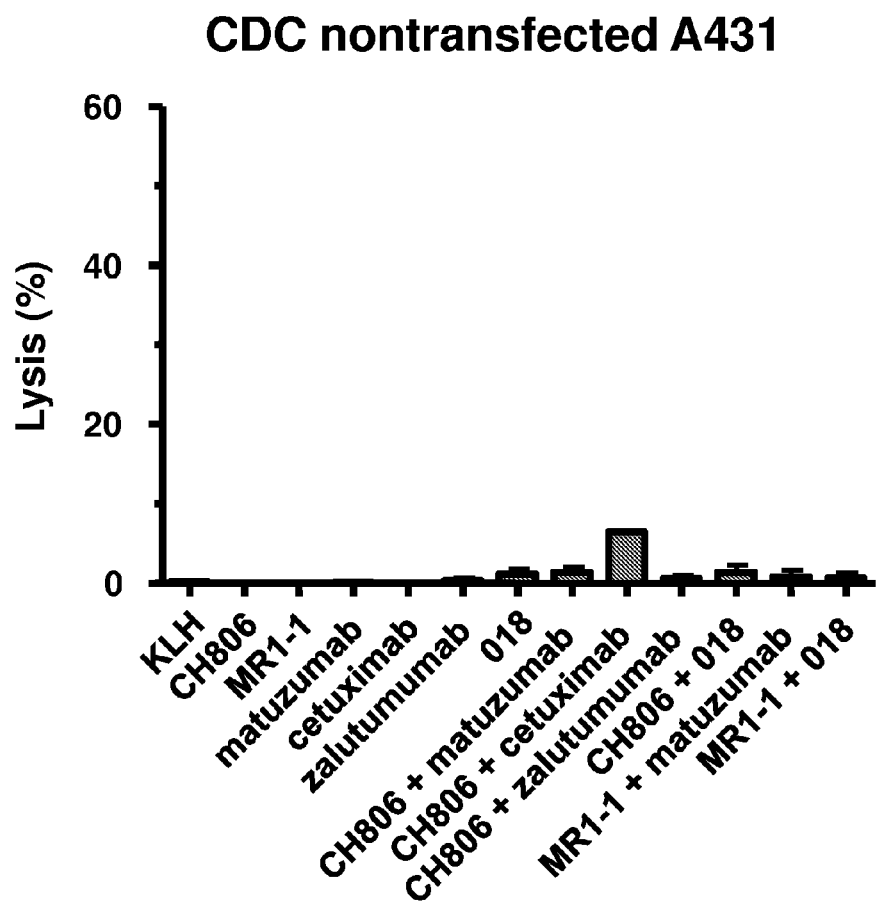

FIG. 19 shows that neither the individual EGFR antibodies tested nor combinations of these with ch806 or MR1-1 induced CDC on untransfected A431 cells, expressing only wild-type EGFR. In contrast, all combinations with ch806 or MR1-1 tested induced significant CDC in EGFR-vIII expressing A431 cells.

Figure 20:
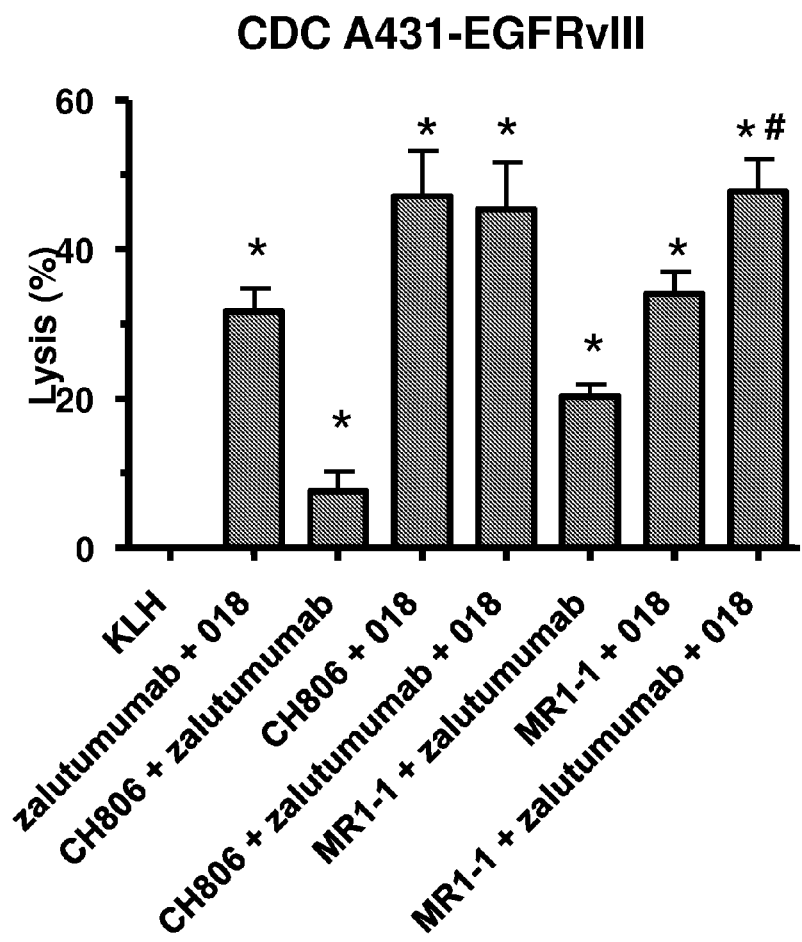
FIG. 20: CDC induction by double and triple combinations with ch806 or MR1-1. Cells were incubated with individual antibodies, or with antibody combinations at additive antibody concentrations of 20 μg/ml/well. * marks significant CDC, a significant difference between double and triple combinations (p<0.05) is indicated by #.

FIG. 20 shows CDC induction by double and triple combinations with ch806 or MR1-1. The triple combination of ch806, zalutumumab and 018 induced even more lysis of EGFR-vIII expressing cells than the double combinations of MR1-1 and zalutumumab or MR1-1 and antibody 018.

SEQUENCE LISTING

SEQ ID NO: 1 the heavy chain CDR1 sequence of antibody 806:
GYSITSDFAWN

SEQ ID NO: 2 the heavy chain CDR2 sequence of antibody 806:
GYISYSGNTRYNPSLK

SEQ ID NO: 3 the heavy chain CDR3 sequence of antibody 806:
VTAGRGFPY

SEQ ID NO: 4 the light chain CDR1 sequence of antibody 806:
HSSQDINSNIG

SEQ ID NO: 5 the light chain CDR2 sequence of antibody 806:
HGTNLDD

SEQ ID NO: 6 the light chain CDR3 sequence of antibody 806:
VQYAQFPWT

SEQUENCE LISTING -continued

VH 1006-003
SEQ ID NO: 7
EVQLVESGGGLVQPGGSLRLSCAASGFTFSSYWMTWVRQAPGKGLE
WVANIQQDGSEKNYLDSVKGRFTISRDNAKNSLSLQMNSLRAEDTA
VYYCARTYSGFEDFWGQGTLVTVSS

VL 1006-003
SEQ ID NO: 8
EIVLTQSPATLSLSPGERATLSCRASQSVSSYLAWYQQKPGQAPRL
LIFDASNRATGIPARFSGSGSGTDFTLTISSLEPEDFAVYYCQQRS
NWPPWTFGQGTKVEIK

VH 1006-005
SEQ ID NO: 9
EVQLVESGGGLVQPGGSLRLSCAASRFTFSDYWMTWVRQAPGKGLE
WVAHIKQDGSEKYYVDSVKGRFTISRDNAKNSLYLQMNSLRAEDTA
LYYCARGFLIYFDYWGQGTLVTVSS

VL1 1006-005
SEQ ID NO: 10
EIVLTQSPATLSLSPGERATLSCRASQSVSSYLAWYQQKPGQAPRL
LIYDASNRATGIPARFSGSGSGTDFTLTISSLEPEDFAVYYCQQRS
NWPWTFGQGTKVEIK

VL2 1006-005
SEQ ID NO: 11
EIVLTQSPATLSLSPGERATLSCRASQSVSSYLAWYQQKPGQAPRL
LIYDASNRATGIPARFSGSGSGTDFTLTISSLEPEDFAVYYCQQRS
NWWTFGQGTKVEIK

VH 1006-008
SEQ ID NO: 12
EVQLVESGGGLVQPGGSLRLSCAASGFTFSSYWMSWVRQAPGKGLE
WVANIKQDGSEENYVDSVKGRFTVSRDNAKNSLYLQMNSLRAEDTA
VYYCARTYSGFEDYWGQGTLVTVSS

VL 1006-008
SEQ ID NO: 13
EIVLTQSPATLSLSPGERATLSCRASQSVSSYLAWYQQKPGQAPRL
LIFDASNRATGIPARFSGSGSGTDFTLTISSLEPEDFAVYYCQQRS
NWPPWTFGQGTKVEIK

VH 1006-011
SEQ ID NO: 14
EVQLVESGGGLVQPGGSLRLSCAASGFTFSDYWMSWVRQAPGRGLE
WVAHINQDGSEKYYVDSVKGRFTLSRDTAKNSLYLQMNSLRAEDTA
VYYCARGFLIYFDYWGQGTLVTVSS

VL1 1006-011
SEQ ID NO: 15
EIVLTQSPATLSLSPGERATLSCRASQSVSSYLAWYQQKPGQAPR
LLIYDASNRATGIPARFSGSGSGTDFTLTISSLEPEDFAVYYCQQR
SNWWTFGQGTKVEIK

VL2 1006-011
SEQ ID NO: 16
EIVLTQSPATLSLSPGERATLSCRASQSVSSYLAWYQQKPGQAPRL
LIYDASNRATGIPARFSGSGSGTDFTLTISSLEPEDFAVYYCQQRS
NWPWTFGQGTKVEIK

VH 1006-018
SEQ ID NO: 17
EVQLVESGGGLVQPGGSLRLSCAASGFTFSSYWMNWVRQAPGKGLE
WVANIKKDGSEKYYVDSVKGRFTISRDNAKNSLYLQMNSLRAEDTA
VYYCARDLGWGWGWYFDLWGRGTLVTVSS

VL 1006-018
SEQ ID NO: 18
EIVLTQSPATLSLSPGERATLSCRASQSVSSYLAWYQQKPGQAPRLL
IYDASNRATGIPARFSGSGSGTDFTLTISSLEPEDFAVYYCQQRSNW
PPTFGQGTKVEIK

SEQUENCE LISTING

<160> NUMBER OF SEQ ID NOS: 27

<210> SEQ ID NO 1
<211> LENGTH: 11
<212> TYPE: PRT
<213> ORGANISM: Artificial Sequence
<220> FEATURE:
<223> OTHER INFORMATION: antibody variable region sequence

<400> SEQUENCE: 1

Gly Tyr Ser Ile Thr Ser Asp Phe Ala Trp Asn
1               5                   10

<210> SEQ ID NO 2
<211> LENGTH: 16
<212> TYPE: PRT
<213> ORGANISM: Artificial Sequence
<220> FEATURE:
<223> OTHER INFORMATION: antibody variable region sequence

<400> SEQUENCE: 2

Gly Tyr Ile Ser Tyr Ser Gly Asn Thr Arg Tyr Asn Pro Ser Leu Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: antibody variable region sequence

<400> SEQUENCE: 3

Val Thr Ala Gly Arg Gly Phe Pro Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: antibody variable region sequence

<400> SEQUENCE: 4

His Ser Ser Gln Asp Ile Asn Ser Asn Ile Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: antibody variable region sequence

<400> SEQUENCE: 5

His Gly Thr Asn Leu Asp Asp
1               5

<210> SEQ ID NO 6
<211> LENGTH: 9
<212> TYPE: PRT
<213> ORGANISM: Artificial Sequence
<220> FEATURE:
<223> OTHER INFORMATION: antibody variable region sequence

<400> SEQUENCE: 6

Val Gln Tyr Ala Gln Phe Pro Trp Thr
1               5

<210> SEQ ID NO 7
<211> LENGTH: 117
<212> TYPE: PRT
<213> ORGANISM: Artificial Sequence
<220> FEATURE:
<223> OTHER INFORMATION: antibody variable region sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Gln Gln Asp Gly Ser Glu Lys Asn Tyr Leu Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
                85                  90                  95

Ala Arg Thr Tyr Ser Gly Phe Glu Asp Phe Trp Gly Gln Gly Thr Leu
            100                 105                 110

Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: antibody variable region sequence

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Trp Thr Phe Gly Gln Gly Thr Lys Val Glu Ile Lys
            100                 105

<210> SEQ ID NO 9
<211> LENGTH: 117
<212> TYPE: PRT
<213> ORGANISM: Artificial Sequence
<220> FEATURE:
<223> OTHER INFORMATION: antibody variable region sequence

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Thr Phe Ser Asp Tyr
            20                  25                  30

```
Trp Met Thr Trp Val Arg Gln Ala Pro Gly Lys Gly Leu Glu Trp Val
            35                  40                  45

Ala His Ile Lys Gln Asp Gly Ser Glu Lys Tyr Tyr Val Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Gly Phe Leu Ile Tyr Phe Asp Tyr Trp Gly Gln Gly Thr Leu
                100                 105                 110

Val Thr Val Ser Ser
            115

<210> SEQ ID NO 10
<211> LENGTH: 107
<212> TYPE: PRT
<213> ORGANISM: Artificial Sequence
<220> FEATURE:
<223> OTHER INFORMATION: antibody variable region sequence

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                      55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
                100                 105

<210> SEQ ID NO 11
<211> LENGTH: 106
<212> TYPE: PRT
<213> ORGANISM: Artificial Sequence
<220> FEATURE:
<223> OTHER INFORMATION: antibody variable region sequence

<400> SEQUENCE: 11

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                      55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
                100                 105
```

```
<210> SEQ ID NO 12
<211> LENGTH: 117
<212> TYPE: PRT
<213> ORGANISM: Artificial Sequence
<220> FEATURE:
<223> OTHER INFORMATION: antibody variable region sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Glu Asn Tyr Val Asp Ser Val
    50                  55                  60

Lys Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Tyr Ser Gly Phe Glu Asp Tyr Trp Gly Gln Gly Thr Leu
            100                 105                 110

Val Thr Val Ser Ser
        115

<210> SEQ ID NO 13
<211> LENGTH: 108
<212> TYPE: PRT
<213> ORGANISM: Artificial Sequence
<220> FEATURE:
<223> OTHER INFORMATION: antibody variable region sequence

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Trp Thr Phe Gly Gln Gly Thr Lys Val Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: antibody variable region sequence

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

```
Trp Met Ser Trp Val Arg Gln Ala Pro Gly Arg Gly Leu Glu Trp Val
             35                  40                  45

Ala His Ile Asn Gln Asp Gly Ser Glu Lys Tyr Tyr Val Asp Ser Val
 50                  55                  60

Lys Gly Arg Phe Thr Leu Ser Arg Asp Thr Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Phe Leu Ile Tyr Phe Asp Tyr Trp Gly Gln Gly Thr Leu
             100                 105                 110

Val Thr Val Ser Ser
            115

<210> SEQ ID NO 15
<211> LENGTH: 106
<212> TYPE: PRT
<213> ORGANISM: Artificial Sequence
<220> FEATURE:
<223> OTHER INFORMATION: antibody variable region sequence

<400> SEQUENCE: 15

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Trp Thr
                 85                  90                  95

Phe Gly Gln Gly Thr Lys Val Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: antibody variable region sequence

<400> SEQUENCE: 16

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Trp
                 85                  90                  95

Thr Phe Gly Gln Gly Thr Lys Val Glu Ile Lys
            100                 105
```

```
<210> SEQ ID NO 17
<211> LENGTH: 121
<212> TYPE: PRT
<213> ORGANISM: Artificial Sequence
<220> FEATURE:
<223> OTHER INFORMATION: antibody variable region sequence

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Lys Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Trp Gly Trp Gly Trp Tyr Phe Asp Leu Trp Gly
            100                 105                 110

Arg Gly Thr Leu Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: antibody variable region sequence

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 19
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 19
tgaaagcttc taatacgact cactataggg c                              31
```

```
<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
tatccacctt ccactgtact tt                                              22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
gggagtagag tcctgaggac tg                                              22

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ggataacaat ttcacacagg                                                 20

<210> SEQ ID NO 23
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 23
tgaaagcttc taatacgact cactataggg caagcagtgg tatcaacgca gagt           54

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
acccactgct tactggctta tcg                                             23

<210> SEQ ID NO 25
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 25
ccgtgatctg tcaccacata attacctttc ttttcctcca gagcccgact c              51

<210> SEQ ID NO 26
<211> LENGTH: 51
<212> TYPE: DNA
<213> ORGANISM: Artificial Sequence
<220> FEATURE:
<223> OTHER INFORMATION: Synthetic oligonucleotide
```

```
<400> SEQUENCE: 26
gagtcgggct ctggaggaaa agaaaggtaa ttatgtggtg acagatcacg g          51

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
cctgtgcagg tgatgttcat gg                                          22
```

The invention claimed is:

1. An isolated monoclonal antibody, or an antigen binding portion thereof, which binds to EGFR and comprising the CDR1, CDR2, and CDR3 sequences of the heavy and light chain variable region sequences set forth in SEQ ID NOs: 17 and 18, respectively.

2. An isolated monoclonal antibody, or an antigen binding portion thereof, which binds to EGFR and comprising the heavy and light chain variable region sequences set forth in SEQ ID NOs: 17 and 18, respectively.

3. The antibody, or antigen binding portion thereof, of claim 1, wherein the antibody induces ADCC of tumor cells.

4. The antibody, or antigen binding portion thereof, of claim 1, which is a human, humanized, or chimeric antibody.

5. The antibody, or antigen binding portion thereof, of claim 1, which is an IgG1, IgA, IgE, IgM, IgG4, or IgD antibody.

6. An immunoconjugate comprising the antibody of claim 1 linked to an agent.

7. A composition comprising the antibody of claim 1 and a carrier.

8. A nucleic acid encoding the heavy or light chain variable region sequence of the antibody of claim 1.

9. A vector comprising the nucleic acid of claim 8.

10. An isolated cell comprising the nucleic acid of claim 8.

11. A method for inducing antibody-dependent cytotoxicity (ADCC) of a tumor cell comprising administering, to a subject in need thereof, a therapeutically effective amount of the antibody of claim 1.

12. A method of detecting the presence of EGFR in a sample comprising contacting the sample with antibody of claim 1, or an antigen binding portion thereof, under conditions that allow for formation of a complex between the antibody and EGFR, and detecting the formation of a complex.

13. A bispecific antibody comprising the antibody of claim 1 and a second binding specificity.

14. The antibody, or antigen binding portion thereof, of claim 5, which is an IgG1 antibody.

* * * * *